United States Patent
Ohri et al.

(10) Patent No.: US 10,413,566 B2
(45) Date of Patent: *Sep. 17, 2019

(54) THIXOTROPIC OXIDIZED CELLULOSE SOLUTIONS AND MEDICAL APPLICATIONS THEREOF

(71) Applicant: Covidien LP, Mansfield, MA (US)

(72) Inventors: Rachit Ohri, Framingham, MA (US); Phillip D. Blaskovich, Salem, MA (US)

(73) Assignee: Covidien LP, Mansfield, MA (US)

( * ) Notice: Subject to any disclaimer, the term of this patent is extended or adjusted under 35 U.S.C. 154(b) by 175 days.

This patent is subject to a terminal disclaimer.

(21) Appl. No.: 15/235,261

(22) Filed: Aug. 12, 2016

(65) Prior Publication Data

US 2016/0346316 A1    Dec. 1, 2016

Related U.S. Application Data

(63) Continuation-in-part of application No. 14/694,112, filed on Apr. 23, 2015, now Pat. No. 9,782,430, which is a continuation-in-part of application No. 14/210,873, filed on Mar. 14, 2014.

(60) Provisional application No. 61/952,164, filed on Mar. 13, 2014, provisional application No. 61/857,332, filed on Jul. 23, 2013, provisional application No. 61/791,475, filed on Mar. 15, 2013.

(51) Int. Cl.
| | | |
|---|---|---|
| *A61K 31/717* | (2006.01) | |
| *A61K 31/445* | (2006.01) | |
| *A61K 31/714* | (2006.01) | |
| *A61K 33/24* | (2019.01) | |
| *A61K 31/295* | (2006.01) | |
| *A61K 49/04* | (2006.01) | |
| *A61L 26/00* | (2006.01) | |

(52) U.S. Cl.
CPC .......... *A61K 31/717* (2013.01); *A61K 31/295* (2013.01); *A61K 31/445* (2013.01); *A61K 31/714* (2013.01); *A61K 33/24* (2013.01); *A61K 49/048* (2013.01); *A61L 26/0023* (2013.01); *A61L 26/0061* (2013.01); *A61L 26/0066* (2013.01); *A61L 2400/06* (2013.01)

(58) Field of Classification Search
CPC .............................. A61K 31/717; C08B 15/04
USPC .......................................................... 514/57
See application file for complete search history.

(56) References Cited

U.S. PATENT DOCUMENTS

| | | | |
|---|---|---|---|
| 1,456,781 A | 5/1923 | Kessler et al. | |
| 3,364,200 A | 1/1968 | Ashton et al. | |
| 3,939,068 A | 2/1976 | Wendt et al. | |
| 3,948,666 A | 4/1976 | Kitanishi et al. | |
| 4,064,062 A | 12/1977 | Yurko | |
| 4,142,913 A | 3/1979 | McCorsley, III et al. | |
| 4,166,800 A | 9/1979 | Fong | |
| 4,196,282 A | 4/1980 | Franks et al. | |
| 4,211,574 A | 7/1980 | McCorsley, III et al. | |
| 4,246,221 A | 1/1981 | McCorsley, III | |
| 4,278,790 A | 7/1981 | McCormick | |
| 4,282,236 A | 8/1981 | Broom | |
| 4,302,252 A | 11/1981 | Turbak et al. | |
| 4,324,593 A | 4/1982 | Varga | |
| 4,352,770 A | 10/1982 | Turbak et al. | |
| 4,416,698 A | 11/1983 | McCorsley, III | |
| 4,626,253 A | 12/1986 | Broadnax, Jr. | |
| 5,008,385 A | 4/1991 | Diamantoglou | |
| 5,057,334 A | 10/1991 | Vail | |
| 5,134,229 A | 7/1992 | Saferstein et al. | |
| 5,162,430 A | 11/1992 | Rhee et al. | |
| 5,324,775 A | 6/1994 | Rhee et al. | |
| 5,410,016 A | 4/1995 | Hubbell et al. | |
| 5,484,913 A | 1/1996 | Stilwell et al. | |
| 5,498,705 A | 3/1996 | Oin | |
| 5,514,379 A | 5/1996 | Weissleder et al. | |
| 5,540,874 A | 7/1996 | Yamada et al. | |
| 5,543,441 A | 8/1996 | Rhee et al. | |
| 5,550,187 A | 8/1996 | Rhee et al. | |
| 5,696,101 A | 12/1997 | Wu et al. | |
| 5,725,601 A | 3/1998 | Tajiri et al. | |
| 5,747,060 A | 5/1998 | Sackler et al. | |
| 5,752,974 A | 5/1998 | Rhee et al. | |
| 5,780,618 A * | 7/1998 | Banker ................. | A61K 8/04 536/120 |
| 5,819,350 A | 10/1998 | Wang | |
| 5,874,500 A | 2/1999 | Rhee et al. | |
| 5,914,003 A | 6/1999 | Kosowski et al. | |
| 5,922,340 A | 7/1999 | Berde et al. | |

(Continued)

FOREIGN PATENT DOCUMENTS

| | | |
|---|---|---|
| EP | 0905144 A1 | 3/1999 |
| EP | 1953174 A1 | 8/2008 |

(Continued)

OTHER PUBLICATIONS

Saito, et al., "TEMPO-mediated oxidation of native cellulose: SEC-MALLS analysis of water-soluble and insoluble fractions in the oxidized products", Cellulose, Dec. 31, 2005, vol. 12, pp. 305-315.

Chinese Office Action for Appln. No. 201310369316.3 dated Sep. 12, 2016.

Chinese Office Action for Chinese appln. No. 201310367279.2 dated Aug. 31, 2016.

Extended European Search Report for EP 16179199 dated Sep. 12, 2016.

(Continued)

*Primary Examiner* — Shaojia A Jiang

(57) ABSTRACT

A method of treatment includes agitating a thixotropic oxidized cellulose solution; administering the agitated thixotropic oxidized cellulose solution to a target tissue site; and allowing the agitated thixotropic oxidized cellulose solution to gel at the target tissue site.

12 Claims, 25 Drawing Sheets

(56) References Cited

U.S. PATENT DOCUMENTS

| | | |
|---|---|---|
| 6,093,557 A | 7/2000 | Pui et al. |
| 6,152,943 A | 11/2000 | Sawhney |
| 6,156,677 A | 12/2000 | Brown Reed et al. |
| 6,165,201 A | 12/2000 | Sawhney et al. |
| 6,179,862 B1 | 1/2001 | Sawhney |
| 6,217,911 B1 | 4/2001 | Vaugn et al. |
| 6,309,569 B1 | 10/2001 | Farrar et al. |
| 6,399,362 B1 | 6/2002 | Pui et al. |
| 6,500,777 B1 | 12/2002 | Wiseman et al. |
| 6,514,534 B1 | 2/2003 | Sawhney |
| 6,566,406 B1 | 5/2003 | Pathak et al. |
| 6,590,095 B1 | 7/2003 | Schleicher et al. |
| 6,605,294 B2 | 8/2003 | Sawhney |
| 6,627,749 B1 | 9/2003 | Kumar |
| 6,656,200 B2 | 12/2003 | Li et al. |
| 6,673,093 B1 | 1/2004 | Sawhney |
| 6,699,908 B2 | 3/2004 | Sackler et al. |
| 6,703,047 B2 | 3/2004 | Sawhney et al. |
| 6,746,869 B2 | 6/2004 | Pui et al. |
| 6,764,720 B2 | 7/2004 | Pui et al. |
| 6,818,018 B1 | 11/2004 | Sawhney |
| 7,009,034 B2 | 3/2006 | Pathak et al. |
| 7,214,727 B2 | 5/2007 | Kwon et al. |
| 7,247,338 B2 | 7/2007 | Pui et al. |
| 7,279,322 B2 | 10/2007 | Pui et al. |
| 7,347,850 B2 | 3/2008 | Sawhney |
| 7,498,063 B2 | 3/2009 | Pui et al. |
| 7,514,097 B1 | 4/2009 | Himeda et al. |
| 7,592,418 B2 | 9/2009 | Pathak et al. |
| 7,595,392 B2 | 9/2009 | Kumar et al. |
| 7,611,494 B2 | 11/2009 | Campbell et al. |
| 7,616,397 B2 | 11/2009 | Hayakawa et al. |
| 7,645,874 B2 | 1/2010 | Saferstein et al. |
| 7,649,089 B2 | 1/2010 | Kumar et al. |
| 7,662,801 B2 | 2/2010 | Kumar et al. |
| 7,709,631 B2 | 5/2010 | Harris et al. |
| 7,754,002 B2 | 7/2010 | Maase et al. |
| 7,828,936 B2 | 11/2010 | Luo et al. |
| 7,951,248 B1 | 5/2011 | Fallis et al. |
| 8,033,483 B2 | 10/2011 | Fortier et al. |
| 8,062,673 B2 | 11/2011 | Figuly et al. |
| 8,152,777 B2 | 4/2012 | Campbell et al. |
| 8,210,453 B2 | 7/2012 | Hull et al. |
| 8,252,339 B2 | 8/2012 | Figuly et al. |
| 8,252,921 B2 | 8/2012 | Vignon et al. |
| 8,367,089 B2 | 2/2013 | Wan et al. |
| 8,408,480 B2 | 4/2013 | Hull et al. |
| 8,470,360 B2 | 6/2013 | McKay |
| 8,518,440 B2 | 8/2013 | Blaskovich et al. |
| 8,617,132 B2 | 12/2013 | Golzarian et al. |
| 8,629,187 B2 | 1/2014 | Shiomi et al. |
| 8,663,703 B2 | 3/2014 | Lerner et al. |
| 8,741,098 B2 | 6/2014 | Koshiishi et al. |
| 8,865,432 B2 | 10/2014 | Hayakawa et al. |
| 9,155,707 B2 | 10/2015 | Ying et al. |
| 9,168,227 B2 | 10/2015 | Blaskovich et al. |
| 9,782,430 B2 * | 10/2017 | Ohri .................. A61K 31/717 |
| 2002/0072598 A1 | 6/2002 | Besemer et al. |
| 2003/0073663 A1 | 4/2003 | Wiseman et al. |
| 2003/0078209 A1 | 4/2003 | Schmidt |
| 2003/0152637 A1 | 8/2003 | Chasin et al. |
| 2005/0131225 A1 | 6/2005 | Kumar et al. |
| 2005/0145258 A1 * | 7/2005 | Dong .................. A61J 1/10 |
| | | 128/898 |
| 2005/0272697 A1 | 12/2005 | Herzberg et al. |
| 2006/0008505 A1 | 1/2006 | Brandon |
| 2006/0121266 A1 | 6/2006 | Fandel et al. |
| 2009/0163936 A1 | 6/2009 | Yang et al. |
| 2010/0100123 A1 | 4/2010 | Bennett |
| 2010/0203151 A1 | 8/2010 | Hiraoka |
| 2011/0089375 A1 | 4/2011 | Chan et al. |
| 2011/0293690 A1 | 12/2011 | Griffin et al. |
| 2013/0244523 A1 | 9/2013 | Schmitz et al. |
| 2014/0171907 A1 | 6/2014 | Golzarian et al. |
| 2014/0274945 A1 | 9/2014 | Blaskovich et al. |
| 2015/0224133 A1 | 8/2015 | Ohri et al. |

FOREIGN PATENT DOCUMENTS

| | | |
|---|---|---|
| EP | 2022802 A1 | 2/2009 |
| EP | 2465548 A2 | 6/2012 |
| EP | 2614843 A2 | 7/2013 |
| GB | 2055107 A | 2/1981 |
| JP | 60214728 A | 10/1985 |
| WO | 9856894 A1 | 12/1998 |
| WO | 2002053599 A2 | 7/2002 |
| WO | 2003068245 A1 | 8/2003 |
| WO | 2005047339 A1 | 5/2005 |
| WO | 2005058198 A1 | 6/2005 |
| WO | 2006006140 A1 | 1/2006 |
| WO | 2007106251 A1 | 9/2007 |
| WO | 2007140573 A1 | 12/2007 |
| WO | 2009021688 A1 | 2/2009 |
| WO | 2009067462 A1 | 5/2009 |
| WO | 2010/118285 A1 | 10/2010 |
| WO | 2010120269 A1 | 10/2010 |
| WO | 2012034049 A2 | 3/2012 |
| WO | 2012045094 A1 | 4/2012 |
| WO | 2013/003619 A1 | 1/2013 |

OTHER PUBLICATIONS

European communication from EP Appl. No. 12805198.4 dated Jul. 29, 2016.

Extended European Search Report for appln. No. 16166569.0 dated Jul. 20, 2016.

European Office Action for appln. No. 13 174 412.0 dated Aug. 17, 2016.

S.P. Sanghvi, et al., "A method to control particle size of cellulose acetate trimellitate microspheres", J. Microencapsulation, vol. 10, No. 2, pp. 181-194 (1993).

Charles L. McCormick, et al., "Solution Studies of Cellulose in Lithium Chloride and N,N-Dimethylacetamide", Macromolecules, vol. 18, pp. 2394-2401 (1985).

Judy D. Timpa, "Application of Universal Calibration in Gel Permeation Chromatography for Molecular Weigh Determinations of Plant Cell Wall Polymers: CottonFiber", J. Agric. Food Chem., vol. 39, pp. 270-275 (1991).

Jürgen Röhrling, et al., "A Novel Method for the Determination of Carbonyl Groups in Cellulosics by Fluorescence Labeling. 2. Validation and Applications", Biomacromolecules, vol. 3, pp. 969-975 (2002).

Matija Strlic, et al., "Size exclusion chromatography of cellulose in LiCl/N,N-dimethylacetamide", J. Biochem. Biophys. Methods, vol. 56, pp. 265-279 (2003).

Tatyana Ecrmeeva, "Size-exclusion chromatography of enzymatically treated cellulose and related polysaccharides: a review", J. Biochem. Biophys. Methods, vol. 56, pp. 253-264 (2003).

Yen T. Bao, et al., "New Approach to Aqueous Gel Permeation Chromatography of Nonderivatizated Cellulose", Journal of Applied Polymer Science, vol. 25, pp. 263-275 (1980).

Matija Strlic, et al., "Evaluation of size-exclusion chromatography and viscometry for the determination of molecular masses of oxidised cellulose", Journal of Chromatography A, vol. 805, pp. 93-99 (1998).

Ute Henniges, et al., "Studies into the Early Degradation Stages of Cellulose by Different Iron Gall Ink Components," Macromol. Symp., vol. 262, pp. 150-162 (2008).

Akira Isogai, et al., "Preparation of polyuronic acid from cellulose by TEMPO-mediated oxidation", Cellulose, vol. 5, pp. 153-164 (1998).

Tsuguyuki Saito, et al., "TEMPO-mediated oxidation of native celulose: SEC-MALLS analysis of water-soluble and -insoluble fractions in the oxidized products", Cellulose, vol. 12, pp. 305-315 (2005).

(56) References Cited

OTHER PUBLICATIONS

Arne Lund Kvernheim, et al., "Size-Exclusion Chromatography and Methylation Analysis of Cellulose in N,N-Dimethylacetamide/LiCl", Acta Chem. Scand., vol. 43, pp. 209-211 (1989).

Izumi Shibata, et al., "Nitroxide-mediated oxidation of cellulose using TEMPO derivatives: HPSEC and NMR analyses of the oxidized products", Cellulose, vol. 10, pp. 335-341 (2003).

Yoshihiro Shigemasa, et al., "Ruthenium Catalyzed Oxidation of Polysaccharide", Polymer Journal, vol. 23, No. 10, pp. 1279-1281 (1991).

M. Singh, et al., "An insulin delivery system from oxidized cellulose", Journal of Biomedical Materials Research, vol. 15, pp. 655-661 (1981).

Soroor Sharifpoor, et al., "In vitro release of a water-soluble agent from low viscosity biodegradable, injectable oligomers", European Journal of Pharmaceutics and Biopharmaceutics, vol. 65, pp. 336-345 (2007).

R. van Dijkhuizen-Radersma, et al., "Control of vitamin B12 release from poly(ethylene glycol)/poly(butylene terephthalate) multiblock copolymers", Biomaterials, vol. 23, pp. 1527-1536 (2002).

Akihiro Matsumoto, et al., "A novel preparation method for PLGA microspheres using non-halogenated solvents", Journal of Controlled Release, vol. 129, pp. 223-227 (2008).

Sergio Freitas, "Microencapsulation by solvent extraction/evaporation: reviewing the state of the art of microsphere preparation process technology", Journal of Controlled Release, vol. 102, pp. 313-332 (2005).

Christian Wischke, et al., "Principles of encapsulating hydrophobic drugs in PLA/PLGA microparticles", International Journal of Pharmaceutics, vol. 364, pp. 298-327 (2008).

P. J. Watts, et al., "Microencapsulation Using Emulsification/Solvent Evaporation: An Overview of Techniques and Applications", Critical Reviews in Therapeutic Drug Carrier Systems, vol. 7, Issue 3, pp. 235-259 (1990).

Andreas S. Lübbe, M.D., Ph.D., et al., "Clinical Applications of Magnetic Drug Targeting", Journal of Surgical Research, vol. 95, pp. 200-206 (2001).

Brian Dennis Plouffe, "Magnetic particle based microfluidic separation of cancer cells from whole blood for applications in diagnostic medicine", Chemical Engineering Dissertations, Northeastern University (2011).

R.V. Ramanujan, et al., "Magnetic Particles for Hyperthermia Treatment of Cancer", Proc. First Intl. Bioengg. Conf., 69-72 (2004).

Barbara D. Raynal, "Nano-Magnetic Particles for Cancer Diagnostics", Biological Applications, The 2009 NNIN REU Research Accomplshments, pp. 32-33 (2009).

Margarethe Hofmann-Amtenbrink, et al., "Superparagmagnetic nanoparticles for biomedical applications", Transworld Research Network, vol. 37/661, No. 2, pp. 119-149 (2009).

J.F.W. Nijsen, et al., "General introduction: Advances in nuclear oncology, microspheres for internal radionuclide therapy of liver tumours", Current Medicinal Chemistry, vol. 9, No. 1, pp. 73-82 (2002).

Extended European Search Report from Appl. No. EP 13174412.0 dated Nov. 6, 2013.

International Search Report from Application No. PCT/US2012/044692 dated Jan. 7, 2014.

International Search Report from PCT Appl. No. PCT/US13/60123 dated Apr. 28, 2014.

Extended European Search Report from Appl. No. 13174415.3 dated Oct. 8, 2015.

Extended European Search Report for application No. 15186802.3 dated Feb. 1, 2016.

Le Corre P et al: "Preparation and characterization of bupivacaine-loaded polylactide and polylactide-co-glycolide microspheres", International Journal of Pharmaceutics, Elsevier BV, NL, vol. 107, No. 1, Jun. 20, 1994 (Jun. 20, 1994), pp. 41-49.

Mccormick et al., Solution studies of cellulose in lithium chloride and N, N-dimethylacetamide, Macromolecules, vol. 18, No. 12, Dec. 1, 1985, pp. 2394-2401.

Kim et al., "Structural studies of electrospun cellulose nanofibers", Polymer, Elsevier Science Publishers B.V. BG, vol. 47, No. 14, Jun. 28, 2006, pp. 5097-5107.

Australian Patent Examination Report from Appln. No. AU 2012275265 dated Apr. 22, 2016.

European Search Report No. 12805198.4 dated Apr. 13, 2015, 11 pp.

International Search Report for PCT/US2012/44692 date of completion is Nov. 6, 201 (5 pgs).

S. Ho, et al., "Clinical evaluation of the partition model for estimating radiation doses from yttrium-90 microspheres in the treatment of hepatic cancer", European Journal of Nuclear Medicine, vol. 24, No. 3, pp. 293-298 (1997).

Russell J. Mumper, et. al., "Neutron-Activated Holmium-166-poly (L-Lactic Acid) Microspheres: A Potential Agent for the Internal Radiation Therapy of Hepatic Tumors", The Journal of Nuclear Medicine, vol. 32, No. 11, pp. 2139-2143 (1991).

S. Ho, et al., "Internal Radiation Therapy for Patients with Primary or Metastatic Hepatic Cancer", Cancer, vol. 83, No. 9, pp. 1894-1907 (1998).

J.H. Turner, et al., "Ho-microsphere liver radiotheraphy: a preclinical SPECT dosimetry study in the pig", Nuclear Medicine Communications, vol. 15, pp. 545-553 (1994).

A. Jaworek, "Electrospray droplet sources for thin film deposition", J Mater Sci, vol. 42, pp. 266-297 (2007).

A. Jaworek, et al., "Trajectories of charged aerosol particles near a spherical collector", Journal of Electrostatics, vol. 51-52, pp. 603-609 (2001).

James C. Andrews, et al., "Hepatic Radioembolization with Yttrium-90 Containing Glass Microspheres: Preliminary Results and Clinical Follow-Up", The Journal of Nuclear Medicine, vol. 35, No. 10, pp. 1637-1644 (1994).

International Search Report from European Application No. EP 13170166.6 dated Aug. 6, 2013.

International Search Report from European Application No. 13174367.6 dated Sep. 16, 2013.

International Search Report from European Application No. 13174376.7 dated Sep. 25, 2013.

Maekawa et al., "Properties of 2, 3-Dicarboxy Cellulose Combined with Various Metallic Ions", Journal of Applied Polymer Science, Dec. 31, 1984, vol. 29, pp. 2289-2297.

European Examination Report dated Jan. 14, 2019 issued in corresponding EP Appln. No. 16166569.0.

European Search Report dated Dec. 20, 2017 issed in corresponding EP 17186044.

* cited by examiner

THIXOTROPIC OXIDIZED CELLULOSE SOLUTIONS AND MEDICAL APPLICATIONS THEREOF

CROSS-REFERENCE TO RELATED APPLICATIONS

The present application is a continuation in part of U.S. application Ser. No. 14/694,112 filed Apr. 23, 2015, which is a continuation in part of U.S. application Ser. No. 14/210,873 filed Mar. 14, 2014, which claims the benefit of and priority to U.S. Provisional Patent Application No. 61/791,475, filed Mar. 15, 2013, U.S. Provisional Patent Application No. 61/857,332, filed Jul. 23, 2013, and U.S. Provisional Patent Application No. 61/952,164, filed Mar. 13, 2014. The entire disclosures of each of the foregoing applications are incorporated by reference herein.

BACKGROUND

Technical Field

The present disclosure relates to systems and methods for dissolving cellulose. In particular, the present disclosure provides processes for dissolving modified cellulose to provide solutions having thixotropic properties. The thixotropic solutions are useful in embolization and other medical procedures.

Background of Related Art

Cellulose is the most abundant biorenewable material, and cellulose-derived products have been used in multiple industries, including manufacturing of textiles and medical devices. Apart from the use of unmodified cellulose-containing materials (for example wood, cotton), modern cellulose technology requires extraction and processing of cellulose from primary sources using techniques that have changed very little since the inception of the modern chemical industry.

The full potential of cellulose and cellulose products has not been fully exploited, partially due to the historical shift towards petroleum-based polymers, and also by the limited number of common solvents in which cellulose is readily soluble. Traditional cellulose dissolution processes, including the cuprammonium and xanthate processes, are often cumbersome or expensive and require the use of unusual solvents, typically with a high ionic strength, under relatively harsh conditions.

Various processes for dissolving cellulose have been previously disclosed. See, for example, McCormick, et al. "Solution Studies of Cellulose in Lithium Chloride and N,N-Dimethylacetamide," Macromolecules, 1985, Vol. 18, No. 12, 1985, pp. 2394-2401; Timpa, "Application of Universal Calibration in Gel Permeation Chromatography for Molecular Weight Determination of Plant Cell Wall Polymers: Cotton Fiber," J. Agric. Food Chem., 1991, 39, 270-275; and Strlič et al., "Size Exclusion Chromatograhy of Cellulose in LiCl/N,N-Dimethylacetamide," J. Biochem. Biophys. Methods, 2003, 56, pp. 265-279.

Improved processes for dissolving cellulose, that overcome the need for high thermal treatment, excessive physical manipulation (e.g., stirring), and/or lengthy treatment periods, all of which contribute to the degradation of the cellulose and removal of oxidized groups from oxidized cellulose, remain desirable.

SUMMARY

According to an embodiment of the present disclosure, a method of treatment is disclosed. The method includes: applying a shear force to a thixotropic oxidized cellulose solution to form a reduced viscosity thixotropic oxidized cellulose solution; and delivering the reduced viscosity thixotropic oxidized cellulose solution to a target tissue site, wherein the viscosity of the thixotropic oxidized cellulose solution increases at the target tissue site after delivery.

According to one aspect of the above embodiment, the method further includes contacting the thixotropic oxidized cellulose solution with a bioactive agent.

According to another embodiment of the present disclosure, a method of treatment is disclosed. The method includes: forming a thixotropic oxidized cellulose solution; contacting the thixotropic oxidized cellulose solution with a bioactive agent to form a thixotropic formulation; loading the thixotropic formulation into a delivery device; applying a shear force to the thixotropic formulation within the delivery device to form a reduced viscosity thixotropic formulation; and delivering the reduced viscosity thixotropic formulation to a target tissue site from the delivery device, wherein the viscosity of the thixotropic oxidized cellulose solution increases at the target tissue site after delivery.

According to one aspect of any of the above embodiments, delivering the reduced viscosity thixotropic oxidized cellulose solution includes injecting the reduced viscosity thixotropic oxidized cellulose solution into the target tissue to form a tissue scaffold therein.

According to one aspect of any of the above embodiments, delivering the reduced viscosity thixotropic oxidized cellulose solution includes injecting the reduced viscosity thixotropic oxidized cellulose solution into a synovial joint.

According to one aspect of any of the above embodiments, delivering the reduced viscosity thixotropic oxidized cellulose solution includes delivering the reduced viscosity thixotropic oxidized cellulose solution to an organ having a fistula such that the viscosity of the thixotropic oxidized cellulose solution increases after delivery to seal the fistula.

According to one aspect of any of the above embodiments, delivering the reduced viscosity thixotropic oxidized cellulose solution further includes placing a tissue implant at the fistula and securing the tissue implant to the fistula with the thixotropic oxidized cellulose solution.

According to another aspect of any of the above embodiments, the delivery device is selected from the group consisting of a syringe, a catheter, and an endoscope.

According to another aspect of any of the above embodiments, administering the reduced viscosity thixotropic oxidized cellulose solution/formulation to the target tissue site includes injecting the reduced viscosity thixotropic oxidized cellulose solution/formulation into the target tissue site.

According to another aspect of any of the above embodiments, the target tissue site is disposed within an eye, a vagina, a nose, a throat, a mouth, an esophagus, a stomach, a penis, intestines, or an anus.

According to another aspect of any of the above embodiments, the reduced viscosity thixotropic oxidized cellulose solution/formulation to the target tissue site includes applying the reduced viscosity thixotropic oxidized cellulose solution/formulation topically.

According to another aspect of any of the above embodiments, the thixotropic oxidized cellulose solution includes oxidized cellulose having a degree of oxidation from about 0.5 to about 0.8 and is present from about 5% by weight to 20% by weight of the thixotropic oxidized cellulose solution.

BRIEF DESCRIPTION OF DRAWINGS

Various embodiments of the present disclosure will be described herein below with reference to the figures wherein.

DETAILED DESCRIPTION OF THE EMBODIMENTS

The present disclosure provides a system and method for dissolving cellulose. In embodiments, the present disclosure provides a process using a polar aprotic solvent and a salt, which is added in a step-wise manner to dissolve oxidized or non-modified cellulose. The dissolution process according to the present disclosure minimizes degradation of the oxidized cellulose, by conducting the process in an inert and dry atmosphere, introducing the salt in a specific sequence, heating the solution at a predetermined temperature and time, and minimizing shearing forces on the solution.

As described herein, cellulose includes natural (e.g., non-modified) or modified (e.g., treated) celluloses including, but not limited to, oxidized cellulose, alkyl celluloses, hydroxyalkyl celluloses, cellulose ethers, cellulose esters, nitrocelluloses, combinations thereof, and the like. Additional examples of suitable modified cellulose derivatives include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

As used herein, oxidized cellulose denotes cellulose having at least a portion of hydroxyl groups replaced by carboxyl, aldehyde, and/or ketone groups by oxidation. Oxidized cellulose may be formed using any technique within the purview of those skilled in the art. For example, cellulose may be oxidized by exposing it to an oxidation medium, such as a densified or supercritical fluid including, but not limited to, nitrogen dioxide, carbon dioxide, combinations thereof, and the like. In embodiments, the oxidation medium may include a combination of densified or supercritical fluids, such as nitrogen dioxide dissolved in carbon dioxide. The cellulose material may be exposed to the oxidizing medium for a period of time of from about 20 minutes to about 24 hours, in embodiments from about 1 hour to about 5 hours, at a temperature from about 20° C. to about 60° C., in embodiments from about 30° C. to about 45° C., and at a pressure of from about 20 bars to about 250 bars, in embodiments from about 30 bars to about 90 bars. Methods for oxidizing cellulose materials using densified fluids are disclosed, for example, in U.S. Patent Application Publication No. 2008/0194805, the entire disclosure which is incorporated by reference herein. Other methods for preparing oxidized cellulose materials are also disclosed, for example, in U.S. Pat. Nos. 3,364,200; 4,626,253; 5,484,913; and 6,500,777, the entire disclosures of each of which are incorporated by reference herein.

Figure 1:
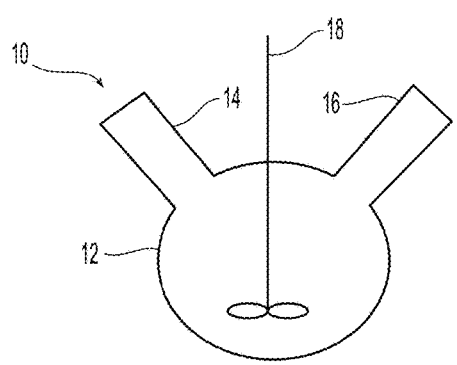
FIG. 1 is a schematic diagram of a system for dissolving cellulose in accordance with the present disclosure.

Turning now to FIG. 1, a system for dissolving cellulose, including oxidized cellulose, in accordance with the present disclosure is provided. System 10 includes a reactor vessel 12, which may be a three-neck round-bottom flask. The reactor vessel 12 includes a gas inlet 14 and a gas outlet 16, both of which are coupled to a source of inert gas (not shown). The reactor vessel 12 may also include any number of inlets, spigots, and other connectors to provide for convenient addition of reactants and/or removal of products to or from the vessel 12, respectively. Dissolution of the oxidized cellulose may be carried out either as a continuous process or a batch process.

The dissolution process is performed in an inert, i.e., oxygen free, and dry atmosphere. In embodiments, the reactor vessel 12 may be purged with an inert gas prior to commencing the dissolution process by circulating an inert gas through the reactor vessel 12 via the inlet 14 and outlet 16. The gas may also be circulated through the reactor vessel 12 during the dissolution process. Suitable inert gases include, but are not limited to, nitrogen and noble gases such as helium, neon, argon, and combinations thereof.

Initially, a solvent is added to the reactor vessel 12 through any suitable inlet. In embodiments, the solvent for dissolving oxidized cellulose may be any polar aprotic organic solvent having a boiling point from about 175° C. to about 205° C., in embodiments from about 180° C. to about 202° C. Suitable solvents include, but are not limited to, N,N-Dimethylacetamide, N-methyl-2-pyrrolidinone (NMP), and combinations thereof.

The solvent may also be sparged (e.g., gas bubbled therethrough) by the inert gas to exclude moisture and dissolved oxygen therefrom. Cellulose is then added to the solvent and may be agitated by a mixer 18 to swell the cellulose. Mixing is performed at a relatively low rate to prevent degradation of the cellulose. The stirring may be from about 100 revolutions per minute (rpm) to about 500 rpm, in embodiments from about 150 rpm to about 250 rpm. As described above, the reactor vessel 12 may be a round-bottomed container, which further minimizes the shearing forces imparted on the cellulose by the mixer 18.

The mixture of the solvent and oxidized cellulose may be heated to a temperature from about 115° C. to about 145° C., in embodiments from about 120° C. to about 140° C., in further embodiments from about 130° C. to about 135° C. In embodiments, the degree of oxidation of oxidized cellulose dissolved using the processes in accordance with the present disclosure may be from about 0.2 to about 1.0, in embodiments from about 0.3 to about 0.9, in further embodiments from about 0.5 to about 0.7. As used herein, the term "degree of oxidation" refers to a ratio of carboxyl groups to hydroxyl groups of the cellulose. The "degree of oxidation" is also used as an average degree of oxidation of the entire cellulose sample. Without being bound by any particular theory, it is believed that the temperature of the mixture of the solvent and oxidized cellulose depends on the degree of oxidation of the oxidized cellulose. As the degree of oxidation increases, the temperature required to swell oxidized cellulose decreases. Conversely, as the degree of oxidation decreases, the temperature required to swell oxidized cellulose increases. Heating of the cellulose during the dissolution process is minimized. Heating of the cellulose may lead to degradation thereof, including destruction of reactive groups of oxidized cellulose and decrease in molecular weight.

The mixture of the solvent and oxidized cellulose having a degree of oxidation of about 0.5 or above may be heated to a temperature from about 115° C. to about 135° C., in embodiments from about 125° C. to about 130° C. The mixture of the solvent and oxidized cellulose having a degree of oxidation of from about 0.25 to about 0.5 may be heated to a temperature from about 130° C. to about 145° C., in embodiments from about 135° C. to about 140° C.

The solvent initially swells the cellulose due to its relatively high polarity. Swelling of oxidized cellulose may continue from about 1 hour to about 4 hours, in embodiments from about 1.5 hours to about 2.5 hours. After the oxidized cellulose has swelled, the temperature of the mixture is reduced. In embodiments, the mixture of oxidized cellulose may be cooled prior to addition of the salt to a temperature from about 90° C. to about 120° C., in embodiments from about 100° C. to about 110° C.

Without being bound by any particular theory, it is believed that introduction of the salt into the mixture provides intercalation of the salt into the cellulose. The swelling of the cellulose with the solvent enhances the introduction of the salt into the cellulose, which in turn, affects final dissolution of the cellulose. In embodiments, the salt may be any alkali halide salt. Suitable salts include, but are not limited to, lithium halides, such as lithium fluoride, lithium chloride, lithium bromide, and lithium iodide; sodium halides, such as sodium fluoride, sodium chloride, sodium bromide, and sodium iodide; potassium halides, such as potassium fluoride, potassium chloride, potassium bromide, and potassium iodide; and any combinations of the foregoing. The salt may be present in an amount of from about 0.1% by weight to 3% by weight of the oxidized cellulose, in embodiments from about 0.25% by weight to about 2% by weight of the oxidized cellulose. Conventional dissolution processes rely on higher salt concentration to dissolve non-modified cellulose, which are unsuitable for dissolving oxidized cellulose. Lower concentration of salt prevents or lessens degradation of oxidized cellulose including destruction of reactive groups of oxidized cellulose and decrease in molecular weight as described above. As used herein, designation of "by weight" may be used interchangeably with "by volume" and denotes "by weight/volume."

Conducting the dissolution process in a step-wise manner, namely, initial swelling of the cellulose in the solvent prior to introduction of the salt, allows for dissolution of the cellulose at lower temperatures than conventional processes, which usually require temperatures above 150° C. The step-wise dissolution process at lower temperatures also prevents or lessens degradation of oxidized cellulose including destruction of reactive groups of oxidized cellulose and decrease in molecular weight as described above. In embodiments, the degree of oxidation of the dissolved oxidized cellulose may be from about 80% to about 120% of the degree of oxidation of the pre-processed, i.e., undissolved, oxidized cellulose, in embodiments from about 90% to about 110%. In embodiments, the molecular weight of the dissolved oxidized cellulose may be from about 80% to about 100% of the molecular weight of the pre-processed, i.e., undissolved, oxidized cellulose, in embodiments from about 90% to about 95%. As used herein, the term "molecular weight" refers to weight average molecular weight (Mw) of the cellulose. This term "molecular weight" is also used as an average molecular mass of the entire cellulose sample. Undissolved (e.g., prior to dissolution) oxidized cellulose may have a molecular weight from about 50,000 Daltons to about 500,000 Daltons, in embodiments from about 100,000 Daltons to about 400,000 Daltons.

If the oxidized cellulose is not fully dissolved, the process may continue with stirring and heating at a lower temperature from about 40° C. to about 80° C., in embodiments from about 50° C. to about 60° C., for a period of time from about 1 hour to about 5 hours, in embodiments from about 2 hours to about 3 hours, until the oxidized cellulose is dissolved. The resulting solution of oxidized cellulose includes oxidized cellulose present at a concentration of from about 5 milligrams per milliliter (mg/mL) to about 25 mg/mL, in embodiments from about 10 mg/mL to about 20 mg/mL.

The system of FIG. 1 may also be used to dissolve non-modified cellulose. The process for dissolving non-modified cellulose may utilize the same solvents as described above for dissolving oxidized cellulose. Initially, the non-modified cellulose is swelled in the solvent. The mixture of the solvent and non-modified cellulose may be heated to a temperature from about 135° C. to about 165° C., in embodiments from about 145° C. to about 155° C. The solvent initially swells the cellulose due to its relatively high polarity. Swelling of non-modified cellulose may continue from about 1 hour to about 4 hours, in embodiments from about 1.5 hours to about 2.5 hours. After the non-modified cellulose has swelled, the temperature of the mixture is reduced. In embodiments, the mixture of non-modified cellulose may be cooled prior to addition of the salt to a temperature from about 140° C. to about 160° C., in embodiments from about 145° C. to about 155° C.

The salt may be present in an amount of from about 0.1% by weight to 10% by weight of the non-modified cellulose, in embodiments from about 0.5% by weight to about 9% by weight of the non-modified cellulose. If the non-modified cellulose is not fully dissolved, the process may continue with stirring and heating at a lower temperature, from about 40° C. to about 80° C., in embodiments from about 50° C. to about 60° C., for a period of time from about 12 hours to about 36 hours, in embodiments from about 16 hours to about 24 hours, until the non-modified cellulose is dissolved.

The dissolved oxidized cellulose may then be used to form macro, micro or nanoparticles. In the present application, the terms "macroparticles," "macrospheres," "macrocapsules," "microparticles," "microspheres," "microcapsules," "nanoparticles," "nanospheres," and "nanocapsules" denote any particle having any regular or irregular shape and size from about 0.001 µm to about 2 mm, in embodiments from about 0.01 µm to about 1 mm.

Particle formation may be carried out either in as a continuous process with the dissolution process (e.g., subjecting the solution to high shearing forces, adding neutralizing agents, and/or adding cations) or a batch process. In embodiments, cellulose particles may be formed by subjecting the dissolved cellulose to high shearing forces (e.g., in a high-shear apparatus such as a mixer, extruder, and the like) in the presence of a solvent or non-solvent, a neutralizing agent, an aqueous solution having multivalent cations, and combination thereof.

The term "non-solvent", as used herein, is used in its broadest sense and includes any substance or mixture of substances in which cellulose is not soluble. Suitable solvents and co-solvents include, but are not limited to, NMP, DMAc and aqueous solutions, and combinations thereof. Suitable non-solvents include, but are not limited to, alkanes, oils glycerins, glycols, and combinations thereof. The solvent or non-solvent may be present in an amount of from about 1% by weight to 45% by weight of the cellulose, in embodiments from about 5% by weight to about 30% by weight of the cellulose, in embodiments from about 10% by weight to 20% by weight of the cellulose.

In embodiments, oxidized cellulose particles may be formed by contacting the dissolved cellulose with an aqueous solution having a neutralizing agent. The dissolved cellulose and the aqueous neutralizing solution may also be subjected to high shearing forces. In embodiments, the neutralizing agent may be used to neutralize the pendant carboxyl acid groups in the cellulose to regulate the final particle size and morphology, so a neutralizing agent herein may also be referred to as a "basic neutralization agent." Any suitable basic neutralization reagent may be used in accordance with the present disclosure. In embodiments, suitable basic neutralization agents may include both inorganic basic agents and organic basic agents. Suitable basic agents may include ammonia, ammonium hydroxide, potassium hydroxide, sodium hydroxide, sodium carbonate, sodium bicarbonate, lithium hydroxide, potassium carbonate, potassium bicarbonate, combinations thereof, and the like. Suitable basic agents may also include monocyclic compounds and polycyclic compounds having at least one nitrogen atom, such as, for example, secondary amines, which include aziridines, azetidines, piperazines, piperidines, pyridines, bipyridines, terpyridines, dihydropyridines, morpholines, N-alkylmorpholines, 1,4-diazabicyclo[2.2.2]octanes, 1,8-diazabicycloundecanes, 1,8-diazabicycloundecenes, dimethylated pentylamines, trimethylated pentylamines, pyrimidines, pyrroles, pyrrolidines, pyrrolidinones, indoles, indolines, indanones, benzindazones, imidazoles, benzimidazoles, imidazolones, imidazolines, oxazoles, isoxazoles, oxazolines, oxadiazoles, thiadiazoles, carbazoles, quinolines, isoquinolines, naphthyridines, triazines, triazoles, tetrazoles, pyrazoles, pyrazolines, and combinations thereof. In embodiments, the monocyclic and polycyclic compounds may be unsubstituted or substituted at any carbon position on the ring.

The neutralizing agent may be utilized as a solid such as, for example, sodium hydroxide flakes and may be dissolved in water to form an aqueous solution. The neutralizing agent may be added to the oxidized cellulose such that the pH of the solution is from about 5 to about 9, in embodiments from about 6 to about 8. As noted above, the basic neutralization agent may be added to neutralize the cellulose possessing carboxylic acid groups (e.g., oxidized cellulose). Neutralization of the pendant carboxylic acids in the formation of cellulose particles by minimizing inter-particle repulsion from anionic charges of the carboxylic acid groups. The addition of the basic neutralization agent may thus raise the pH of an emulsion including a cellulose possessing acid groups to a pH of from about 5 to about 12, in embodiments, from about 6 to about 11.

In embodiments, oxidized cellulose particles may be formed by contacting the dissolved cellulose with an aqueous solution having multivalent cations, including divalent and trivalent cations. The dissolved cellulose and the cation solution may also be subjected to high shearing forces. In embodiments, cellulose particles may be formed by a continuous two-phase spray preparation, in which a cation solution is initially sprayed onto a subtrate followed by spraying of a dissolved cellulose solution. In further embodiments, a cationic solution may be combined with an oxidized cellulose solution to form cross-linked gels in situ as described in further detail below.

Suitable cations include, but are not limited to, those of calcium ($Ca^{+2}$), barium ($Ba^{+2}$), zinc ($Zn^{+2}$), magnesium ($Mg^{+2}$), iron ($Fe^{+2}$, $Fe^{+3}$), platinum ($Pt^{+4}$), chromium ($Cr^{+6}$), and combinations thereof. In embodiments, the cation may be introduced by dissolving a suitable salt of the cation, which include, but are not limited to, halides, sulfates, carbonates, phosphates, nitrates, nitrites, oxides, acetates, combinations thereof, and the like. The cations may be present in an amount of from about 0.01% by weight to 25% by weight of the oxidized cellulose, in embodiments from about 1% by weight to about 18% by weight of the cellulose, in embodiments from about 2% by weight to 15% by weight of the oxidized cellulose depending upon end use of the oxidized cellulose solution. Cations act as cross-linking agents by cross-linking pendant carboxylic groups disposed on oxidized cellulose thereby forming cellulose particles. A dual-compartment spraying device (e.g., micro-fluidizer) may be used which stores the aqueous cation solution and the oxidized cellulose solution, which ejects the solution contemporaneously thereby mixing the particles and forming particles that are deposited on a substrate (e.g., tissue). Applicators for mixing two components are disclosed in commonly-owned U.S. Pat. Nos. 7,611,494, 8,033,483, 8,152,777 and U.S. Patent Application Publication Nos. 2010/0065660 and 2010/0096481, the entire disclosures of all of which are incorporated by reference herein.

In embodiments, the degree of oxidation of the oxidized cellulose particles formed from the dissolved oxidized cellulose of the present disclosure may be from about 80% to about 120% of the degree of oxidation of the pre-processed, i.e., undissolved, oxidized cellulose, in embodiments from about 90% to about 110%. In embodiments, the molecular weight of the oxidized cellulose particles may be from about 80% to about 100% of the molecular weight of the pre-processed, i.e., undissolved, oxidized cellulose, in embodiments from about 90% to about 95%. Undissolved (e.g., prior to dissolution) oxidized cellulose may have a molecular weight from about 50,000 Daltons to about 500,000 Daltons, in embodiments from about 100,000 Daltons to about 400,000 Daltons.

The dissolved cellulose and/or cellulose particles may be used to form various medical devices suitable for a variety of surgical and wound applications. The medical devices according to the present disclosure may be any structure suitable for being attached to or implanted into tissue, body organs or lumens, including, but not limited to, micro and nano-particles, woven and non-woven fabrics, coatings, patches, films, foams, slit sheets, pledgets, tissue grafts, stents, scaffolds, buttresses, wound dressings, meshes, and/or tissue reinforcements.

In embodiments, as noted above, one or more bioactive agents may be added to the solvent such that the bioactive agents are incorporated into the oxidized cellulose solution, which may then be used to form various medical devices. A variety of bioactive agents, including polar and non-polar compounds, are soluble in the solvents described-above suitable for forming oxidized cellulose solutions according to the present disclosure. In embodiments, the bioactive agent may also be added after the oxidized cellulose particles have been formed. The terms "bioactive agent" and "active therapeutic agent" (ATA) are used interchangeably and in its broadest sense include any substance or mixture of substances that have clinical use. Consequently, bioactive agents may or may not have pharmacological activity per se, e.g., a dye, or fragrance. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present medical device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins, such as vitamin A, B-12, C, D, combinations thereof, and the like; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; anti-histamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include biologics and protein therapeutics, such as, viruses, bacteria, lipids, amino acids, cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, α-IFN, and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

The present disclosure also provides for compositions and methods of fabricating microspheres encapsulating one or more bioactive agents within the oxidized cellulose. Suitable bioactive agents are described in more detail above. Oxidized cellulose microspheres may have a theoretical bioactive agent loading from about 80% to about 120%, in embodiments from about 90% to about 110%, in further embodiments from about 95% to about 105%, in additional embodiments from about 98% to about 102%. Oxidized cellulose microspheres may have an actual bioactive agent loading from about 0.01% to about 99.99%, in embodiments from about 15% to about 85%, in further embodiments from about 25% to about 55%, in additional embodiments from about 40% to about 60%.

Soluble oxidized cellulose, by virtue of being dissolved in a polar solvent as described above, allows for formation of microspheres including hydrophilic bioactive agents encapsulated in the oxidized cellulose. This may be accomplished by using an oil-in-oil emulsion method followed by a solvent extraction step in extraction media. As used herein the term "emulsion" refers to a mixture of two or more liquids that are immiscible, in which one liquid form a continuous phase and the other liquid forms a discontinuous phase. As used herein the terms "discontinuous" and "disperse" phase are used interchangeably and refer to the compound being dispersed through the continuous phase and may include the bioactive agent, optional encapsulating polymer and/or corresponding solvent or solvating agent. As used herein the term "continuous" phase refers to a liquid, such as, oils, that are used to extract the solvent or solvating agent from the discontinuous phase. These liquids are usually immiscible with the solvent employed in the discontinuous phase. As used herein the terms "thinning agent" and "third" phase are used interchangeably and refer to a liquid that reduces the viscosity of the continuous phase, is miscible with the continuous phase and/or removes residual continuous phase from the surface of the microsphere. In embodiments, the thinning agent may be immiscible with the discontinuous phase. As used herein the term "oil-in-oil" emulsion denotes an emulsion in which both the continuous phase and the discontinuous phase are organic liquids.

In forming microspheres of soluble oxidized cellulose by an oil-in-oil solvent extraction method, one or more hydrophilic bioactive agents may be added to a solution of oxidized cellulose and are mixed sufficiently to ensure a uniform suspension or homogeneous solution. Oxidized cellulose may be present in the solution in an amount from about 0.01% by weight to 45% by weight of the solution, in embodiments, from about 1% by weight to about 30% by weight of the solution, in embodiments from about 5% by weight to 20% by weight of the solution.

The bioactive agent and oxidized cellulose solution forms the discontinuous phase, which is added drop-wise to a vessel including a liquid forming a continuous phase. The continuous phase liquid may be any suitable non-polar compound that is immiscible with the polar solvents used in forming the oxidized cellulose solution. Suitable continuous phase liquids include, but are not limited to, petroleum-based oils, such as light, medium or heavy mineral oils (e.g., mixtures of alkanes having from about 40 carbons to about 60 carbons), plant-based oils, such as cottonseed oil, silicone-based oils, and combinations thereof. In embodiments, the continuous phase may include two or more oils such as, for example, a heavy oil and a light oil, that compete for extraction of the discontinuous phase. In embodiments, the heavy oil and the light oil may be present at a ratio of from about 1:10 to about 10:1, in embodiments from about 1:3 to about 3:1. The discontinuous phase liquid may be present in an amount from about 1% by volume to about 50% by volume of the continuous phase liquid, in embodiments from about 5% to about 20%.

The vessel possessing the continuous phase may be fitted with a baffle. The vessel may include a mixer with an impeller configured to rotate at a rate of from about 25 rpm to about 60,000 rpm, in embodiments, from about 100 rpm to about 15,000 rpm, in further embodiments from about 250 rpm to about 5,000 rpm. The stirring may continue from about 5 seconds to about 4 hours, in embodiments, from about 15 seconds to about 1 hour. The rate of rotation may be adjusted to obtain desired particle size. Size of the microspheres may be tailored by modulating the duration and the speed of homogenization (e.g., stirring of the discontinuous and continuous phases), temperature and/or pressure, altering the ratio of continuous to discontinuous phases, the shear rate, and the molecular weight and concentrations of oxidized cellulose and bioactive agents.

Upon completing the transfer of the discontinuous phase solution into the continuous phase, a third phase liquid may be added to the emulsion to remove the solvent from the discontinuous phase liquid. Suitable third phase liquids include any compound which is miscible with both the continuous and discontinuous phase liquids. The extraction of the solvent occurs due to the solvent being immiscible in the continuous phase liquid but miscible in the third phase liquid. Suitable third phase liquids include isopropyl myristate, hexane, n-heptane, triglycerides and combinations thereof. The third phase liquid may be present in an amount from about 300% by volume to about 200% by volume of the continuous phase liquid, in embodiments from about 140% to about 150%.

Removal of the solvent from the continuous phase facilitates formation of microspheres including the bioactive agent encapsulated by the oxidized cellulose. The emulsion may be stirred from about 0.1 hour to about 24 hours, in embodiments from about 2 hours to about 5 hours, to aid in the extraction of the polar solvent from the microspheres. The microspheres may then be collected via filtration and washed (e.g., with n-heptane) to remove any trace of continuous and discontinuous phase liquids on the surface of the microspheres. The microspheres may then be collected and transferred into a glass scintillation vial under a nitrogen or argon overlay. In embodiments, microspheres may also be formed using spray dry and jet mill techniques.

The oxidized cellulose microspheres are also suitable for encapsulating hydrophilic drugs such as bupivacaine HCl as well as viruses, bacteria, amino acids, peptides, proteins, lipids, vaccines, and combinations thereof since the oil-in-oil emulsion does not react with the water barrier of these bioactive agents.

In other embodiments, the oxidized cellulose solution may also be used to form various types of fibers. In embodiments, the fibers may be solid, hollow, porous, and combinations thereof. Fibers may be formed by any suitable method, including electrospinning, solution casting, extruding, and combinations thereof. The fibers formed from the oxidized cellulose solutions may be used to form a variety of medical devices. The medical devices according to the present disclosure may be any structure suitable for being attached to or implanted into tissue. Suitable structures formed from the fibers include, for example, films, foams, slit sheets, pledgets, tissue grafts, stents, scaffolds, buttresses, wound dressings, meshes, and/or tissue reinforcements. In embodiments, the fibers may be used to form non-woven meshes or tapes, which may be used as passive hemostats. The non-woven structure of a fibrous mesh formed from an oxidized cellulose solution lends itself to use as a wound dressing, due to its ability to filter liquids and/or gases.

The oxidized cellulose solution may also be used to form films and/or coatings. Coatings or films may be formed by depositing the solution by itself or on a substrate, solution-casting, dipping, layering, calendaring, spraying, and combinations thereof. The solvent evaporates, thereby forming the film or coating on a substrate. The films may be incorporated onto other medical devices by applying the solution to the surface of the device, or portion thereof, utilizing any suitable method within the purview of those skilled in the art.

In embodiments, the oxidized cellulose solution may be used to form a sprayable delivery vehicle. In further embodiments, the oxidized cellulose solution may be combined with a second composition that forms a gel or effects precipitation of the oxidized cellulose as described in further detail below.

The viscosity of the solution for forming fibers, films, and other medical devices may be adjusted to achieve a desired viscosity. This may be accomplished by adding one or more plasticizers. Examples of suitable plasticizers include any biocompatible plasticizer, such as lecithin, dibutyl sebacate, citric acid, alcohol esters, polyethylene glycol, polypropylene glycol, and combinations thereof.

Uses for medical devices formed from the dissolved oxidized cellulose include closing and healing visceral wall defects and incisions, including incisions due to the removal of tumors, wounds, anastomoses, and fistulae. The medical devices can improve the healing of a gastro-intestinal anastomosis and may provide an effective approach for the management and prevention of fistula. The medical devices may also prevent complications of polypectomy (e.g., bleeding and perforation). In embodiments, the medical devices may be reinforced with a mesh (e.g., formed on a substrate mesh) for the treatment of inguinal hernia and/or incisional hernia.

The rate of in vitro and in vivo biodegradation of medical devices formed from oxidized cellulose may be regulated by controlling the initial degree of oxidation of the resultant (e.g., dissolved and processed) oxidized cellulose. The greater the degree of oxidation of the oxidized cellulose, the faster the rate of biodegradation in vitro and in vivo. The present disclosure provides for processes that minimize the degradation of the oxidized cellulose during the dissolution process, thereby providing for cellulose having a desired degree of oxidation. Further, biodegradability of cellulose may be controlled by adjusting the molecular weight and degree of oxidation during the dissolution to provide for predictably degrading oxidized cellulose having a predictable degradation profile. Dissolving and processing without materially affecting the degree of oxidation allows for predictable biodegradability of the final products (e.g., medical devices). Thus, control of the rate of degradation of the oxidized cellulose matrix may be accomplished by varying the degree of oxidation, thereby controlling the rate of bioactive agent elution. The degree of oxidation of the oxidized cellulose may also be adjusted during the dissolution process to achieve a desired degree of oxidation.

Dissolved oxidized cellulose may also be utilized to form in situ gels. Oxidized cellulose solution may be prepared using the methods, e.g., solvents, conditions, etc., outlined above. The oxidized cellulose solution may have a pH from about from about 7.0 to about 10.0, in embodiments from about 8.0 to about 9.5. The oxidized cellulose solution may be combined with a gelation composition that, upon contacting the oxidized cellulose solution, forms a gel. The gel may be used as an adhesive to seal tissue and/or to provide for delivery of bioactive agents as described in further detail below.

In embodiments, the oxidized cellulose solution may be combined with a cationic material, such as a cationic polysaccharide. In embodiments, the cationic polysaccharide may be chitosan, carboxymethyl chitin, guar gum, and combinations, optionally in solution. Chitosan is a natural linear co-polymer of N-acetyl D-glucosamine (acetylated unit) and D-glucosamine (non-acetylated unit). Chitosan may be produced by partial or full deacetylation of chitin. Chitin may be extracted from natural sources, e.g., squid, exoskeletons of crustaceans such as shrimp, or vegetable sources such as mushrooms. Chitosan may also be synthetically produced or synthesized by modified microorganisms such as bacteria.

The adhesion of chitosan with other polysaccharides, such as cellulose, includes different kinds of interactions, such as electrostatic interactions, hydrogen bonds, and hydrophobic interactions, resulting in ionic cross-linking with the oxidized cellulose. Chitosan, under certain circumstances, is a cationic polymer containing —$NH_3^+$ groups. The positively charged primary amino groups of chitosan attract anionic groups of other polymers. Thus, chitosan and anionic polymers are able to form polyelectrolyte complexes. Polyelectrolyte complex formation may improve the mechanical properties of the polymers and lead to new structures, such as precipitates, films, fibers, and gels.

Adhesion of chitosan with other polymers may also be promoted by enhancing the mechanical properties of the formulation by creating covalent bonds between both the components of the adhesive formulation. Chitosan has —$NH_2$ groups which can react covalently with carboxyl groups. Thus, chitosan may be mixed with functionalized polymers having carboxyl groups, such as oxidized cellulose.

The chitosan may have a molecular weight from about 1,000 g/mol to about 5,000,000 g/mol, in embodiments from about 5,000 g/mol to about 220,000 g/mol. In embodiments, chitosan has a high molecular weight (HMVV) of from about 450,000 g/mol to about 550,000 g/mol. In other embodiments, chitosan has a low molecular weight (LMVV) of from about 50,000 g/mol to about 150,000 g/mol.

A solution of chitosan may be prepared, in embodiments, by dissolving chitosan in distilled water with a stoichiometric amount of acid, such as HCl or acetic acid, to ensure the complete protonation of all —$NH_2$ groups. The final solution may contain from about 0.5% (w/w) to about 5% (w/w) chitosan, in embodiments from about 2% (w/w) to about 4% (w/w) chitosan. The chitosan solution may have a pH from about from about 1.0 to about 7.0, in embodiments from about 2.0 to about 6.0. The lower pH of the chitosan solution allows for suspension of pH sensitive bioactive agents in one of the solutions, either oxidized cellulose or chitosan, without compromising the bioactivity of the pH sensitive bioactive agents.

In embodiments, bioactive agents, whose bioactivity is reduced or destroyed by high pH, such as chemotherapeutic encapsulated polypeptides, may be suspended in a chitosan solution and incorporated into an in-situ forming gel upon contact with an oxidized cellulose solution. This gel can be fixed onto a targeted site, such as organs, tissue, etc. and anchor the encapsulated peptide, which then can be released. The resulting gel may be either neutral pH upon formation, or the pH can be adjusted, using the pH of the chitosan solution or the oxidized cellulose solution, to provide a friendly pH environment for the bioactivity of the peptide to be maintained.

Another suitable composition for gelation with the oxidized cellulose solution includes an aqueous solution of multi-valent cations, which forms a gel by ionic cross-linking of the oxidized cellulose and cations. Suitable cations include, but are not limited to, those of calcium ($Ca^{+2}$), barium ($Ba^{+2}$), zinc ($Zn^{+2}$), magnesium ($Mg^{+2}$), iron ($Fe^{+2}$, $Fe^{+3}$), platinum ($Pt^{+4}$), chromium ($Cr^{+6}$), and combinations thereof. In embodiments, the cations may be introduced by dissolving a suitable salt of the cations, which include, but are not limited to, halides, sulfates, carbonates, phosphates, nitrates, nitrites, oxides, combinations thereof, and the like in a suitable solvent such as water, methanol, ethanol, and combinations thereof. The cations may be present in an amount of from about 0.01% by weight to 25% by weight of the solution, in embodiments from about 1% by weight to about 18% by weight of the solution, in embodiments from about 2% by weight to 15% by weight of the solution, to achieve a desired mix ratio with the oxidized cellulose solution. The oxidized cellulose solution and the cationic solution form a reversible, ionically cross-linked gel. In embodiments, the gel can be made reversible by the addition of anionic solutions including aqueous solutions having a pH of greater than 7.0, such as solutions of urea, ammonia, amino acids such as, lysine and glycine, anionic polysaccharides such as, alginate, dextran, carboxymethyl cellulose ("CMC"), and combinations thereof.

A solution of oxidized cellulose may also be contacted with a precipitation and/or gelation composition that forms a gel by dilution and/or precipitation of the oxidized cellulose. Precipitation may be accomplished by contacting the oxidized cellulose solution with a composition including a solvent or a non-solvent. Suitable gelation compositions include, but are not limited to, water, saline, phosphate buffered saline, and combinations thereof. In embodiments, an aqueous solution of carboxymethyl cellulose may also be used. Carboxymethyl cellulose may be present in the solution from about 0.5% by weight or volume to about 5% by weight or volume, in embodiments, from about 1% by weight or volume to about 2% by weight or volume.

In embodiments, an aqueous solution of any cross-linker having one or more primary amines including, but not limited to, trilysine, albumin, polyethylene glycol amine, and combinations thereof may be used as a precipitating gelation composition. In further embodiments, an aqueous solution of any suitable Schiff-base compound may also be used as a precipitating gelation composition. As used herein, the term "Schiff-base" compound denotes any compound having a functional group including a carbon-nitrogen double bond with the nitrogen atom connected to an aryl or an alkyl group having a general formula $R_1R_2C=NR_3$, where $R_3$ and at least one of $R_1$ or $R_2$ is an aryl or an alkyl group. Suitable Schiff-base compounds include, but are not limited to, amoxicillin, cephalexin, 2,2-dimethyl benzimidazoline, 2-methyl-2-ethyl benzimidazoline, 2-methyl-2-propyl benzimidazoline, 2-methyl-2-butyl benzimidazoline, 2-methyl-2-hexyl benzimidazoline, 2-methyl-2-decyl benzimidazoline, 2,2-dimethyl-5-methylbenzimidazoline, 2-methyl-2-butyl-6-methyl benzimidazoline, 2,2-diethyl benzimidazoline, 2,2-diethyl benzimidazoline, 2-ethyl-2-hexyl benzimidazoline, 2-methyl-2-isoamyl-5-methyl benzimidazoline, 2,2-dioctyl benzimidazoline, 2,2-didecyl benzimidazoline, 2-propyl-2-pentyl benzimidazoline, 2,2-diethyl-6-ethylbenzimidazoline, 2,2-dipropyl-5-isopropylbenzimidazoline, 2,2-dipropyl-5-methylbenzimidazoline, 2,2-dibutyl-6-methylbenzimidazoline, 2,2-dibutyl-6-dodecylbenzimidazoline, 2-methyl-2-propenyl benzimidazoline, 2-ethyl-2-propenyl-5-methylbenzimidazoline, 2-methyl-2-butenyl benzimidazoline, 2-ethyl-2-butenyl-6-methylbenzimidazoline, 2,2-dihexyl benzimidazoline, 2,2-dihexyl-5-methylbenzimidazoline, and combinations thereof. Contacting of Schiff-base compound and/or small molecule cross-linker solutions with the oxidized cellulose solution results in covalent cross-linking of the oxidized cellulose, which, in turn, produces the gel. In embodiments, the aqueous solution may include CMC as well as the Schiff-base compounds.

In embodiments, a solution of one or more acrylic polymers may also be used to precipitate oxidized cellulose to form gels according to the present disclosure. Suitable acrylic polymers include, but are not limited to, those based on methyl methacrylate, hydroxyethyl acrylate, hydroxyethyl methacrylate, glyceryl acrylate, glyceryl methacrylate, acrylic acid, methacrylic acid, acrylamide, methacrylamide, and combinations thereof. Suitable solvents include acetone, ethyl acetate, dimethyl ether, and combinations thereof.

Upon contact of the oxidized cellulose solution with the precipitating composition, the gel is formed in situ by the dilution of the solvent used to form the oxidized cellulose solution and the subsequent precipitation of the oxidized cellulose. Since the polar solvent of the oxidized cellulose solution is miscible with water and/or organic solvents described above, oxidized cellulose precipitates out in the form of a gel due to the dilution of the solvent.

In embodiments, the precipitating composition may include a bioactive agent, which may be suspended in the precipitating composition. In embodiments, the bioactive agent may be initially suspended in the precipitating composition as a plurality of microspheres as described above. The microspheres may then be re-suspended in either the oxidized cellulose composition and/or the gelation composition. The resulting oxidized cellulose gel prevents the migration of the microspheres from the target site.

As noted above, the gels formed by the solutions of oxidized cellulose and gelation compositions can be used to deliver bioactive agents to tissue or the gels may be used to form articles or coatings thereon containing bioactive agents. The gels anchor the bioactive agents, microspheres, microparticles, and combinations thereof, to target sites, e.g., organs, tissues, etc. Microspheres and microparticles containing bioactive agents may be formed using the methods described above by suspending desired bioactive agents in the oxidized cellulose solution prior to microsphere or microparticle formation. The resulting particles may be suspended in the oxidized cellulose solution, which then may be combined with the cationic and/or chitosan solutions. This may be utilized to secure bioactive agents at the desired sites, including chemotherapeutic agents (e.g., cis-diamminedichloroplatinum(II)) at tumor excision sites, to provide for sustained release of chemotherapeutic agents from the gel and/or the microparticles secured thereby.

The gelation compositions and/or oxidized cellulose solution may be in a liquid form and placed in a syringe or any other suitable delivery vehicle, such as a sprayer, for immediate or later use. The solutions may be placed in delivery vehicles of different volumes so as to reach a specific ratio of each component.

The solutions may be applied convergently to a desired tissue site to form a gel thereon. As used herein, the term "convergently" denotes at least partial overlap of the compositions being applied to the substrate (e.g., tissue, medical device, etc.) either during the application process (e.g., mid-stream) or on a surface of the substrate.

The solutions used to form the gel may also be directly coated on a substrate, such as a mesh. The substrate may be prepared by soaking it in the desired solutions and drying (e.g., in an oven or in a laminar flow hood). In embodiments, the process may be repeated several times to ensure a proper coating displaying the required adhesive properties for the selected indication of use, e.g., fixation of extraperitoneal or retroperitoneal meshes, skin flap closure, etc.

The ratio of each component may be adjusted to provide a desired formulation. Each formulation is characterized by its mix ratio (MR). As used herein, the term "mix ratio" means the amount of the compound and/or reactive groups responsible for gelation (e.g., free amine groups of chitosan and/or amount of cations) versus the amount of free carboxyl groups present on the oxidized cellulose. The mix ratio may be at least about 1, in embodiments from about 1 to about 40, in further embodiments from about 10 to about 30. In embodiments, each component of the gel may be diluted with a buffer prior to use for pH adjustment.

Figure 2:
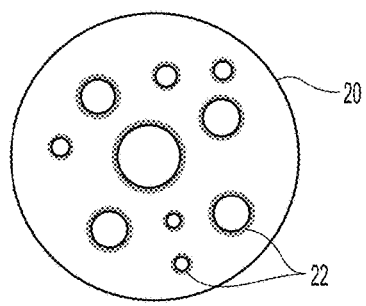
FIG. 2 is a schematic diagram of a doubly-encapsulated microsphere in accordance with the present disclosure.

The present disclosure also provides for compositions and methods of fabricating microspheres having additional microspheres therein encapsulating one or more APIs or bioactive agents. FIG. 2 shows a microsphere 20 having one or more microspheres 22 encapsulated therein. As used herein, "multi-encapsulated microspheres" denote the encapsulation of one or more smaller microspheres 22, e.g., particles, spheres, capsules, and combinations thereof in a single larger microsphere 20. In embodiments, multi-encapsulated microspheres may encapsulate one or more bioactive agents at same or different loading levels.

In a so-called "primary encapsulation," soluble oxidized cellulose may be used to encapsulate a bioactive agent, a water-soluble compound, a water-sensitive chemotherapeutic agent and/or active pharmaceutical ingredient, thereby forming oxidized cellulose microspheres, e.g., microspheres 22, as described above. Primary encapsulation with soluble oxidized cellulose may be carried out using emulsion-based solvent evaporation and/or extraction methods including, but not limited to, single-emulsion methods such as oil-in-water (o/w) and water-in-oil (w/o), double-emulsion methods such as water-in-oil-in-water (w/o/w) and solid-in-oil-in-water (s/o/w), and non-emulsion based methods, such as fluidized-bed, spray-drying, and casting/grinding methods. The primary oxidized cellulose microspheres may then be further encapsulated in a second layer of oxidized cellulose encapsulation, or in another biodegradable polymer, other than oxidized cellulose, in a so-called "secondary encapsulation" forming the microsphere 20 encapsulating the microspheres 22.

As used herein, the term "biodegradable" in reference to a material shall refer to the property of the material being able to be absorbed by the body. In the present application, the terms "biodegradable," "bioresorbable," "bioerodable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body, such that the degradation products are excretable or absorbable by the body after a given period of time. The time period may vary, from about one hour to about several months or more, depending on the chemical nature of the material. In embodiments, the material may not be completely absorbed, provided the non-absorbed material is acceptable for medical use.

Oxidized cellulose microspheres may be formed using oil-in-oil emulsification processes described above. The oxidized cellulose microspheres may then be further micro-encapsulated by using emulsion-based solvent evaporation methods, in which the oxidized cellulose microspheres are suspended in a solution of a biodegradable polymer or cross-linked and further encapsulated in another oxidized cellulose microencapsulation process. The solution may include any suitable biodegradable polymer, a solvent, and an optional emulsifier and/or a surfactant. In embodiments, additional bioactive agents may be added to the biodegradable polymer solution, which may be the same or different from the bioactive agent included in the oxidized cellulose microspheres. In further embodiments, some rounds of encapsulation may include no bioactive agents based on the desired use and/or performance characteristics of multi-encapsulated microspheres (e.g., altered release rate).

Suitable biodegradable polymers used to form microspheres according to the present disclosure include, but are not limited to, aliphatic polyesters, polyamides, polyamines, polyalkylene oxalates, poly(anhydrides), polyamidoesters, copoly(ether-esters), poly(carbonates) including tyrosine derived carbonates, poly(hydroxyalkanoates) such as poly (hydroxybutyric acid), poly(hydroxyvaleric acid), and poly (hydroxybutyrate), polyimide carbonates, poly(imino carbonates) such as such as poly (bisphenol A-iminocarbonate and the like), polyorthoesters, polyoxaesters including those containing amine groups, polyphosphazenes, poly (propylene fumarates), polyurethanes, polymer drugs such as polydiflunisol, polyaspirin, and protein therapeutics, biologically modified (e.g., protein, peptide) bioabsorbable polymers, and copolymers, block copolymers, homopolymers, blends, and combinations thereof.

More specifically, aliphatic polyesters include, but are not limited to, polylactide, polylactide-co-glycolide, polylactide-polycaprolactone, homopolymers and copolymers of lactide (including lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, Δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, α,α diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and polymer blends and copolymers thereof.

Suitable solvents for forming the biodegradable polymer solution of the discontinuous phase for secondary encapsulation include, but are not limited to, ethyl acetate, methylene chloride, perchloroethane, trichloroethylene, hexafluoroisopropanol (HFIP), chloroform, tetrahydrofuran, dimethyl formamide, as well as those pharmaceutical solvents listed in the ICH Q3C (International Conference on Harmonization—residual solvents used in pharmaceutical processing) and combinations thereof.

The emulsifier may be present in an amount from about 0.01% by weight and/or volume to about 25% by weight and/or volume of the solvent, in embodiments from about 0.1% by weight and/or volume to about 10% by weight and/or volume of the solvent, in further embodiments from about 0.5% by weight and/or volume to about 5% by weight and/or volume of the solvent. For oil-in-oil processes, the use of an emulsifier is optional. Suitable emulsifiers include, but are not limited to, water-soluble polymers, such as polyvinyl alcohol ("PVA"), polyvinyl pyrrolidone (PVP), polyethylene glycol (PEG), polypropylene glycol (PPG), PLURONICS™, TWEENS™, polysaccharides, phospholipids, and combinations thereof.

The continuous phase for the secondary encapsulation may also include a surfactant to stabilize the microspheres and adjust the bioactive agent loading efficiency. One, two, or more surfactants may be utilized. Examples surfactants that can be utilized include, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, polyoxamers, combinations thereof, and the like.

Secondary encapsulation of oxidized cellulose microspheres may include cross-linking the microspheres to stabilize subsequent encapsulation and then forming a suspension of the microspheres in the biodegradable polymer solution described above. Oxidized cellulose microspheres may be cross-linked using any of the cationic species described above. The suspension may then be vortexed or intimately stirred to form an emulsion. In embodiments, the oxidized cellulose microspheres may be immediately suspended in the biodegradable polymer solution without cross-linking.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres, or the multi-encased microspheres, i.e., the multi-encapsulated formulation.

For the second round of encapsulation, the solvent may be evaporated and/or extracted. After the solvent is evaporated and/or extracted, the emulsion retains the microspheres formed from the biodegradable polymer encapsulating the oxidized cellulose microspheres. The emulsion also includes free unencapsulated oxidized cellulose microspheres that are suspended in the emulsion. The size of the doubly-encased or multi-encased microspheres may be from about 0.001 μm to about 2 mm, in embodiments the size of the microspheres may be from about 0.01 μm to about 1 mm, in further embodiments the size of the microspheres may be from about 0.1 μm to about 500 μm. Size of the microspheres may be tailored by modulating the duration and the speed of stirring, temperature and/or pressure, altering the ratio of continuous to discontinuous phases, the shear rate created during stirring, and the molecular weight and concentrations of biodegradable polymers, emulsifiers, and surfactants, and other variables within purview of a person skilled in the art.

The primary encapsulation by the oxidized cellulose protects the bioactive agent from organic solvents and/or other conditions used in any subsequent rounds of encapsulation. Oxidized cellulosed may be used to encapsulate both hydrophilic and hydrophobic bioactive agents. While hydrophobic bioactive agents can also be encapsulated using emulsion methods including other biodegradable polymers, encapsulation of hydrophilic bioactive agents is particularly facilitated by dissolved oxidized cellulose.

Soluble oxidized cellulose, by virtue of being dissolved in a polar solvent as described above, allows for formation of microspheres including hydrophilic and/or hydrophobic bioactive agents encapsulated in the oxidized cellulose whereas other biodegradable polymers are better suited to encapsulate hydrophobic bioactive agents. Using oxidized cellulose for the first round of microencapsulation is beneficial since it does not dissolve in most polar or non-polar solvents, with the exception of solvents listed above with respect to dissolution of oxidized cellulose, thus eliminating the risk of microsphere dissolution during the second round of encapsulation. This allows for microencapsulation of both hydrophobic and hydrophilic bioactive agents, which can then be encapsulated into another microsphere.

In embodiments, the first layer of any microspheres may be formed using a biodegradable polymer other than oxidized cellulose using above-described encapsulation methods, which can then be further encapsulated in oxidized cellulose microspheres. Primary encapsulation of bioactive agents using biodegradable polymers may be carried out using emulsion-based solvent evaporation methods including, but not limited to, single-emulsion methods such as oil-in-water (o/w) and water-in-oil (w/o), double-emulsion methods such as water-in-oil-in-water (w/o/w) and solid-in-oil-in-water (s/o/w), and non-emulsion based methods, such as fluidized-bed, spray-drying, and casting/grinding methods.

Where a bioactive agent is first encapsulated in a biodegradable polymer, the bioactive agent may be dissolved in a solution to form a discontinuous phase. Suitable solvents for dissolving bioactive agents could be aqueous and/or organic and include water, saline, methylene chloride, chloroform, and alcohols, examples of which include methanol, ethanol, combinations thereof, and the like. Biodegradable polymer may also be dissolved to form a discontinuous phase using the solvents described above. Homogenization may be used for discontinuous phases if particle size reduction in the loading of the microsphere is desired. Homogenization may be carried by any suitable methods within the purview of one skilled in the art including, but not limited to, stirring, grinding, thermal energy, ultrasound energy, combinations thereof, and the like.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres.

After the solvent is evaporated, the emulsion retains the microspheres formed from the biodegradable polymer encapsulating the bioactive agent. The emulsion also includes free unencapsulated portion of the bioactive agent that is suspended in the emulsion. The size of the microspheres may be from about 0.001 μm to about 2 mm, in embodiments the size of the microspheres may be from about 0.01 μm to about 1 mm, in further embodiments the size of the microspheres may be from about 0.1 μm to about 500 μm. The size of the microspheres may be tailored by modulating the duration and the speed of stirring, temperature and/or pressure, altering the ratio of continuous to discontinuous phases, the shear rate created during stirring, and the molecular weight and concentrations of biodegradable polymers, emulsifiers, and surfactants, and other variables within purview of a person skilled in the art.

The microspheres formed from the biodegradable polymers other than oxidized cellulose may then be suspended in a solution of oxidized cellulose, which is formed according to the processes described above. In forming microspheres of soluble oxidized cellulose by a solid-in-oil-in-oil solvent extraction method, the biodegradable polymer microspheres may be added to a solution of oxidized cellulose and are mixed sufficiently to ensure a uniform suspension. Oxidized cellulose may be present in the solution in an amount from about 0.01% by weight to 45% by weight of the solution, in embodiments, from about 1% by weight to about 30% by weight of the solution, in embodiments from about 5% by weight to 20% by weight of the solution. In embodiments, additional bioactive agents may be added to the oxidized cellulose solution which may be the same or different from the bioactive agents of the biodegradable polymer microspheres (e.g., hydrophilic vs hydrophobic bioactive agents).

The microspheres, the oxidized cellulose solution, and additional bioactive agents, if any, form the discontinuous phase, which is added drop-wise to a vessel including a liquid forming a continuous phase. The continuous phase liquid may be any suitable non-polar compound that is immiscible with the polar solvents used in forming the oxidized cellulose solution. Suitable continuous phase liquids include, but are not limited to, light, medium or heavy mineral oil (e.g., mixtures of alkanes having from about 40 carbons to about 60 carbons), cottonseed oil, and combinations thereof. Additional continuous phase may be added during emulsification. The discontinuous phase liquid may be present in an amount from about 2% by volume to about 40% by volume of the continuous phase liquid, in embodiments from about 5% to about 20%.

Emulsion-based solvent evaporation may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour. Stirring may also be used to remove the discontinuous phase solvent from the emulsion, retaining the doubly-encased microspheres.

Upon completing the transfer of the discontinuous phase solution into the continuous phase, a third phase liquid may be added to the emulsion to remove or extract the solvent from the discontinuous phase liquid. Suitable third phase liquids include any compound which is miscible with the continuous and may be miscible with discontinuous phase solvent. The extraction of the solvent occurs due to the solvent being immiscible in the continuous phase liquid but miscible in the third phase liquid. Suitable third phase liquids include isopropyl myristate, hexane, triglycerides and combinations thereof. The third phase liquid may be present in an amount from about 300% by volume to about 200% by volume of the continuous phase liquid, in embodiments from about 140% to about 150%.

Extraction of the solvent from the discontinuous phase facilitates formation of doubly-encased microspheres including the bioactive agent encapsulated by a biodegradable polymer, other than oxidized cellulose and then further encapsulated by the oxidized cellulose. The emulsion may be stirred from about 0.1 hour to about 24 hours, in embodiments from about 2 hours to about 5 hours, to aid in the extraction of the polar solvent from the microspheres. The microspheres may then be collected via filtration and washed (e.g., with n-heptane) to remove any trace of continuous and discontinuous phase liquids on the surface of the microspheres. The microspheres may then be collected and transferred into a glass scintillation vial under a nitrogen or argon overlay. In embodiments, the microspheres may be cross-linked with a cationic solution and then dried.

Figure 3:
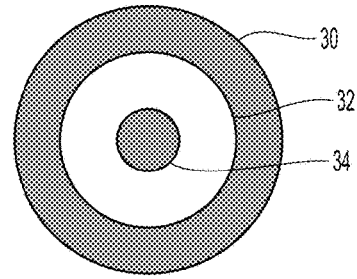
FIG. 3 is a schematic diagram of a multi-encapsulated microsphere in accordance with the present disclosure.

In further embodiments, as shown in FIG. 3, doubly-encapsulated microspheres 32, such as those encapsulating microspheres 34, may then be further encapsulated in either additional microspheres 30 formed from biodegradable polymer or the oxidized cellulose, depending on the material utilized in the second layer encapsulation. In other words, oxidized cellulose is utilized for every other (e.g., alternate) round of encapsulation (e.g., microspheres 30 and 34) with adjacent rounds (e.g., microsphere 32) being formed using biodegradable polymers other than oxidized cellulose. Thus, in embodiments where dissolved oxidized cellulose was used in the initial round of encapsulation (e.g., to form the microsphere 34), biodegradable polymers may be used for the second, (e.g., to form the microsphere 32) fourth, sixth, etc. rounds, and with oxidized cellulose being used in third (e.g., to form the microsphere 30), fifth, seventh, etc. rounds. Conversely, in embodiments where biodegradable polymers are used in the initial round of encapsulation (e.g., to form the microsphere 34), dissolved oxidized cellulose may be used for the second (e.g., to form the microsphere 32), fourth, sixth, etc. rounds, and with the biodegradable polymers being used in third (e.g., to form the microsphere 30), fifth, seventh, etc. rounds. Subsequent encapsulation using dissolved oxidized cellulose and/or biodegradable polymers may be carried out in the manner described above with respect corresponding encapsulation steps. In further embodiments, every multi-encapsulated layer may be formed from oxidized cellulose.

Figure 4:
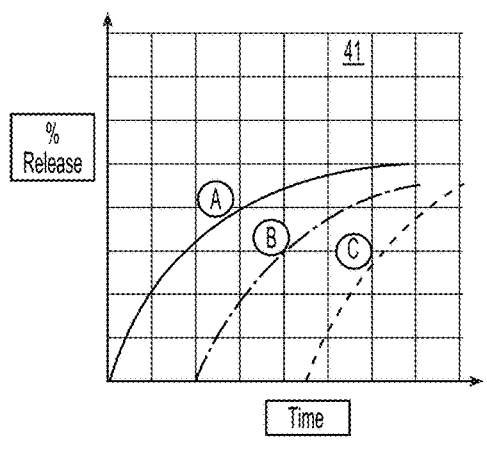
FIG. 4 is a plot of a release profile of a multi-encapsulated microsphere including a plurality of bioactive agents in accordance with the present disclosure.
Figure 5:
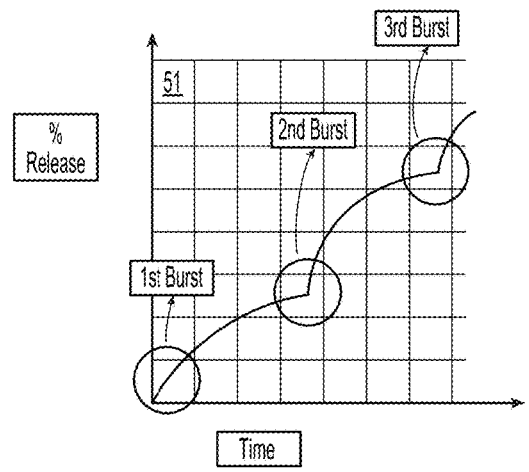
FIG. 5 is a plot of a release profile of a multi-encapsulated microsphere including a single bioactive agent in accordance with the present disclosure.

Multiple encapsulating microspheres offer several therapeutic advantages such as, for example, sequential release of multiple bioactive agents as illustrated in plots 41 and 51 of FIGS. 4 and 5. The plot 41 illustrates a release profile of a multi-encapsulated microsphere, e.g., microsphere 30, having three unique bioactive agents A, B, and C encapsulated within each of the microspheres 30, 32, 34, respectively. As the microsphere 30 degrades, the bioactive agent A is released, with the release profile decaying over time corresponding to the degradation of the microsphere 30. Thereafter, first encapsulated microsphere 32 begins to degrade, thereby releasing the bioactive agent B. Finally, the third bioactive agent C is released once the microsphere 34 commences degradation. Release profiles of each of the bioactive agents A, B, and C may be tailored by adjusting the amount of the encapsulation material (e.g., oxidized cellulose and/or biodegradable polymers). In embodiments, the release profiles may overlap such that one bioactive agent (e.g., A) is released concurrently with another bioactive agent (e.g., B). In further embodiments, the release profiles of each of the bioactive agents may be discrete (e.g., not overlapping) based on desired use and therapy requirements.

The plot 51 illustrates a release profile of a multi-encapsulated microsphere, e.g., microsphere 30, having the same bioactive agent A encapsulated within each of the microspheres 30, 32, 34. Unlike multiple release profiles of distinct bioactive agents A, B, C, encapsulating a single bioactive agent A provides a burst-like release profile, namely, increased dosages of the bioactive agent A are supplied as each of the microspheres 30, 32, 34 degrades. In addition, multiple layers provide an effective method to further slow-down in the release rate of the bioactive agent.

Multi-encapsulated microspheres provide unique advantages over conventional microspheres that encapsulate one or more bioactive agents in a single biodegradable microsphere. Encapsulating multiple bioactive agents in a single-layered microsphere formulation simply provides for simultaneous release of multiple bioactive agents, rather than for a staggered release profile as illustrated in FIG. 4. With respect to a single bioactive agent, a single-layered microsphere formulation is challenging in terms of providing burst and/or pulsatile release of bioactive agents during its degradation as illustrated in FIG. 5.

Multi-encapsulated microspheres provide for more effective bioactive agent loading. In embodiments, when a water-soluble hydrophilic bioactive agent is encapsulated in oxidized cellulose as the first layer of encapsulation using an oil-in-oil (o/o) emulsion solvent-evaporation method, the water-soluble hydrophilic bioactive agent is not lost in the oil-rich, hydrophobic surroundings and can therefore be effectively encapsulated in oxidized cellulose. During the second round of microencapsulation, e.g., with an oil in water o/w method, the water-soluble hydrophilic bioactive agent already has a protective layer, which again results in lower bioactive agent loss to the aqueous media, resulting in higher bioactive agent loading, following double encapsulation. The advantage of more effective bioactive agent loading is useful for encapsulating highly hydrophilic bioactive agent molecules. This is challenging to achieve with more conventional methods that employ single-layered encapsulation or those that employ polymers other than oxidized cellulose.

Multi-encapsulated microspheres further provide for additional protection of fragile, i.e. more vulnerable to environmental conditions, bioactive agents (e.g. biologics or protein therapeutics). Multi-encapsulation offers a significant advantage in controlling their release while keeping them active and protected from denaturation. This is possible for example when a first layer of encapsulation is put in place with oxidized cellulose, thus providing a protective barrier against any harsh conditions in the second (or subsequent) rounds of microencapsulation. This advantage opens up the possibility of effective encapsulation and controlled release of some very fragile biological therapeutics (e.g. protein therapeutics).

With respect to FIG. 2, multi-encapsulation also offers the ability for simultaneous release of multiple bioactive agents. Bioactive agents A, B, and C may be encapsulated individually in the microspheres 22, which are then encapsulated in the microsphere 20. This allows the bioactive agents A, B, and C to release simultaneously, while at the same time ensuring that these molecules do not interact with each other prior to release. Further, an outer encapsulation may be free of any bioactive agents and may act as a buffer, preventing release of bioactive agents until the outer encapsulation has biodegraded. Thus, multi-layered encapsulation using oxidized cellulose can facilitate more control over the timing release of the therapeutic payload.

Microspheres (e.g., single or multi-encapsulated microspheres) according to the present disclosure may also incorporate one or more visualization agents in presence or absence of the bioactive agents. Visualization agents may be encapsulated into single or multi-encapsulated microspheres using the methods and techniques described above with respect to bioactive agents. Suitable visualization agents may be selected from among any of the various non-toxic colored dyes suitable for use in tissue, such as FD&C Blue #1, FD&C Blue #2, FD&C Blue #3, D&C Green #6, methylene blue, indocyanine green, combinations thereof, and the like. In embodiments, additional visualization agents may be used, agents which are green or yellow fluorescent under visible light (e.g., fluorescein or eosin), x-ray contrast agents (e.g., iodinated compounds), ultrasonic contrast agents, MRI contrast agents (e.g., gadolinium containing compounds), CAT or CT scan contract agents (e.g., barium, barium sulphate, iodine, diatrizoic acid, available as GASTROGRAFIN®, etc.), radionucleotides (e.g., isotopes of technetium, iodine, indium, fluorine), combinations thereof, and the like. In further embodiments, the visualization agents may be magnetic materials suitable for tagging various compounds (e.g., cancer proteins) during assays. Suitable magnetic materials are described in further detail below.

With reference to FIG. 2, the microsphere 20 includes a shell encapsulating one or more smaller microspheres 22 therein. The microsphere 20 may include a first visualization agent while the microsphere 22 may include a second visualization agent, respectively, incorporated thereinto. The first and second visualization agents may be the same or different. In embodiments, the first and second visualization agents are different such that as the microspheres 20 are degraded after implantation, the first visualization agent is initially dispersed through the tissue in which the microsphere 20 is introduced, followed by the release of the second visualization agent due to the degradation of the microspheres 22. Sequential release of the first and second visualization agents occurs due to the degradation of the microsphere 20 prior to the degradation of the microsphere 22.

In addition to the first and second visualization agents, the microsphere 20 and the microspheres 22 may include first and second bioactive agents. The combination of the first and second visualization and first and second bioactive agents allows the healthcare professional to visualize/monitor progression, such as, track release rate, release sequence absorption, and other properties of the first and second bioactive agents. Further, this also allows for the monitoring of patient progress and the effectiveness of the bioactive agents.

Figure 6:
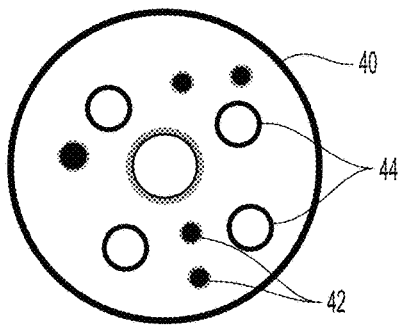
FIG. 6 is a schematic diagram of a multi-encapsulated microsphere including two types of microspheres in accordance with the present disclosure.

With reference to FIG. 6, another embodiment a multi-encapsulating microsphere 40 is shown. The microsphere 40 includes a shell encapsulating one or more smaller first microspheres 42 and one or more smaller second microspheres 44. The first and second microspheres 42 include first and second visualization agents and first and second bioactive agents, respectively. The first and second microspheres 42 and 44 may be formed separately prior to encapsulation within the microsphere 40. In embodiments, the microsphere 40 may include third visualization agent and third bioactive agent. Since the first and second microspheres 42 and 44 are encapsulated in the microsphere 40, the microspheres 42 and 44 begin to degrade concurrently. This allows for evaluation of the progress of the release of the first and second bioactive agents, by measuring the ratio of the first visualization agent to the second visualization agent. In embodiments, the microspheres 42 may include a first visualization agent and a first bioactive agent, while the microspheres 44 may include a second visualization agent and a second bioactive agent. Thus, the release of the first visualization agent corresponds to the release of the first bioactive agent and the release of the second visualization agent corresponds to the release of the second bioactive agent. In embodiments, the microspheres 42 and 44 may be prepared from the same or different materials to tailor absorption rate of the first and second visualization and/or bioactive agents.

In other embodiments, with reference to FIG. 3, a doubly-encapsulating microsphere 30 includes a microsphere 32, which further encapsulates microsphere 34 as described in more detail above. In one embodiment, the microsphere 30 and the microsphere 34 may include first and second bioactive agents, respectively. The microsphere 32 includes a first visualization agent. In this configuration, the first visualization may be used as a demarcation marker to indicate when the first bioactive agent of microsphere 30 has been released completely or mostly, prior to the release of the second bioactive agent from microsphere 34. Sequential release of the first and second bioactive agents occurs due to the degradation of the microsphere 30 prior to the degradation of the microsphere 32, followed by the degradation of the microsphere 34.

Figure 7:
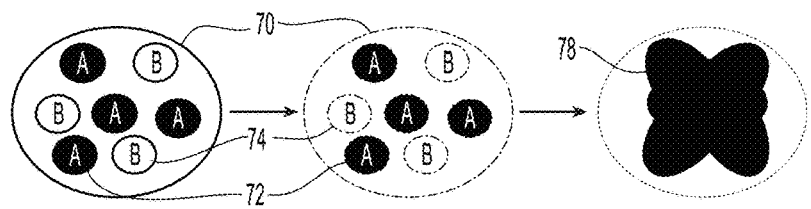
FIG. 7 is a schematic process diagram of multi-encapsulated microsphere including encapsulated first and second precursors in accordance with the present disclosure.

Microspheres (e.g., single or multi-encapsulated microspheres) according to the present disclosure may also incorporate one or more precursors (e.g., hydrogel or adhesive precursors) for forming compositions (e.g., hydrogels or adhesives) in situ. The hydrogel precursors may be in the presence or absence of the bioactive agents as described above. Hydrogel precursors may be encapsulated into single or multi-encapsulated microspheres using the methods and techniques described above with respect to bioactive agents. With reference to FIG. 7, a multi-encapsulating microsphere 70 is shown, having one or more first microspheres 72 including a first hydrogel precursor and one or more second microspheres 74 including a second hydrogel precursor. After implantation, the microsphere 70 prevents immediate polymerization or reaction of the first and second hydrogel precursors. After degradation of the microsphere 70, the microspheres 72 and 74 degrade, thereby releasing the first and second hydrogel precursors, which then react to form a hydrogel 78. In embodiments, the microsphere 70 may also include one or more initiators. Encapsulation of the first and second precursors allows for formation of a gel that is needed after a predetermined period of time, rather than immediately after introduction in vivo. The timing of the polymerization and/or activation may be controlled by adjusting the loading of the first and second precursors and/or the thickness of the microspheres, as well as other formulation characteristics.

Figure 8:
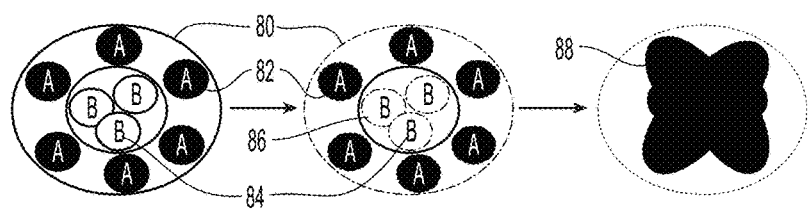
FIG. 8 is a schematic process diagram of multi-encapsulated microsphere including encapsulated first precursors and double-encapsulated second precursors in accordance with the present disclosure.

With reference to FIG. 8, a first multi-encapsulating microsphere 80 is shown, having one or more first microspheres 82 including a first hydrogel precursor and a second multi-encapsulating microsphere 86 including a third microsphere 84 having a second hydrogel precursor. After implantation, the microsphere 80 prevents immediate polymerization of the first and second hydrogel precursors. After degradation of the microsphere 80, the first microspheres 82 degrade, thereby releasing the first hydrogel precursors. The second multi-encapsulating microsphere 86 degrades concurrently with the first microspheres 82, delaying the release of the second hydrogel precursor contained within the second microspheres 84. In embodiments, the microspheres 80 and/or 86 may also include one or more initiators. This configuration delays the release of the second precursor, which also delays cross-linking of the precursors to form a hydrogel 88, which occurs only after the microspheres 84 have also degraded.

The above-described hydrogels may be formed from crosslinking the first and second precursors. The precursor may be a monomer or a macromer. As used herein the terms "hydrogel precursor(s)", "first hydrogel precursor", and "second hydrogel precursor" may be used to refer to components that may be combined to form a hydrogel, either with or without the use of an initiator. Thus, these precursors may, in embodiments, include combinations of reactive precursors and initiated precursors. As used herein the terms "reactive precursor(s)", "first reactive hydrogel precursor(s)", and "second reactive hydrogel precursor(s)" include precursors that may crosslink upon exposure to each other to form a hydrogel. As used herein the term "initiated precursor(s)", "first initiated hydrogel precursor(s)" and "second initiated hydrogel precursor(s)" may be used to describe first and second precursors that crosslink upon exposure to an external source, sometimes referred to herein as an "initiator". Initiators include, for example, ions, UV light, redox-reaction components, combinations thereof, as well as other initiators within the purview of those skilled in the art.

The first and second precursors, whether reactive precursors or initiated precursors, may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"), poly(vinyl pyrrolidinone) ("PVP"), poly (amino acids), poly (saccharides), such as dextran, chitosan, alginates, carboxymethylcellulose, oxidized cellulose, hydroxyethylcellulose and/or hydroxymethylcellulose, hyaluronic acid, and proteins such as albumin, collagen, casein, and gelatin. In embodiments, combinations of the foregoing polymeric materials may be utilized to form a core. The polyethers, and more particularly poly(oxyalkylenes) or poly(ethylene glycol) or polyethylene glycol ("PEG"), may be utilized in some embodiments.

When the core is small in molecular nature, any of a variety of hydrophilic functionalities may be used to make the first and second precursors water soluble. In embodiments, functional groups like hydroxyl, amine, sulfonate and carboxylate, may contribute to the water-solubility of a precursor. For example, the N-hydroxysuccinimide ("NHS") ester of subaric acid is insoluble in water, but by adding a sulfonate group to the succinimide ring, the NHS ester of subaric acid may be made water soluble, without affecting its ability to be used as a reactive group due to its reactivity towards amine groups.

In embodiments, a hydrogel may be formed from reactive precursors through covalent, ionic, or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ or as a consequence of a prevalent condition in the physiological environment, including temperature, pH, ionic strength, combinations thereof, and the like. Chemical (covalent) crosslinking may be accomplished by any of a number of mechanisms including, but not limited to, free radical polymerization, condensation polymerization, anionic or cationic polymerization, step growth polymerization, electrophile-nucleophile reactions, combinations thereof, and the like.

In embodiments, the reactive precursor portion of the hydrogel may be formed from a single type of reactive precursor or multiple types of reactive precursors. In other embodiments, where the hydrogel is formed from multiple types of reactive precursors, for example two reactive precursors, the reactive precursors may be referred to as a first and second reactive precursor. Where more than one reactive precursor is utilized, in embodiments, at least one of the first and second precursors may be a crosslinker, and at least one other reactive hydrogel precursor may be a macromolecule, and may be referred to herein as a "functional polymer".

In some embodiments, reactive precursors may include biocompatible multi-precursor systems that spontaneously crosslink when the precursors are mixed, but wherein the two or more precursors are individually stable for the duration of the deposition process. When the reactive precursors are mixed in an environment that permits reaction (e.g., as relating to pH or solvent), the functional groups react with each other to form covalent bonds. Reactive precursors become crosslinked when at least some of the reactive precursors can react with more than one other precursor. For instance, a precursor with two functional groups of a first type may be reacted with a crosslinking precursor that has at least three functional groups of a second type capable of reacting with the first type of functional groups.

Such reactive components include, for example, first reactive precursors possessing electrophilic groups and second reactive precursors possessing nucleophilic groups. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first reactive precursor may react with a second set of nucleophilic functional groups on a second reactive precursor. In embodiments, such systems include a first reactive precursor including di- or multifunctional alkylene oxide containing moieties, and a second reactive precursor including macromers that are di- or multifunctional amines.

In embodiments the first and second precursors may be multifunctional, meaning that they may include two or more electrophilic or nucleophilic functional groups, such that, for example, an electrophilic functional group on the first reactive hydrogel precursor may react with a nucleophilic functional group on the second reactive hydrogel precursor to form a covalent bond. At least one of the first or second precursors includes more than two functional groups, so that, as a result of electrophilic-nucleophilic reactions, the precursors combine to form crosslinked polymeric products.

In embodiments, each of the first and second precursors include only one category of functional groups, either only nucleophilic groups or only electrophilic functional groups, so long as both nucleophilic and electrophilic reactive precursors are used in the crosslinking reaction. Thus, for example, if the first reactive hydrogel precursor has electrophilic functional groups such as N-hydroxysuccinimides, the second reactive hydrogel precursor may have nucleophilic functional groups such as amines. On the other hand, if the first reactive hydrogel precursor has electrophilic functional groups such as sulfosuccinimides, then the second reactive hydrogel precursor may have nucleophilic functional groups such as amines or thiols.

In embodiments, a multifunctional electrophilic polymer such as a multi-arm PEG functionalized with multiple NHS groups may be used as a first reactive hydrogel precursor and a multifunctional nucleophilic polymer such as trilysine may be used as a second reactive hydrogel precursor. The multi-arm PEG functionalized with multiple NHS groups may, for example, have four, six or eight arms and a molecular weight of from about 5,000 to about 25,000. Other examples of suitable first and second precursors are described in U.S. Pat. Nos. 6,152,943, 6,165,201, 6,179,862, 6,514,534, 6,566,406, 6,605,294, 6,673,093, 6,703,047, 6,818,018, 7,009,034, and 7,347,850, the entire disclosures of each of which are incorporated by reference herein.

Synthetic materials that are readily sterilized and avoid the dangers of disease transmission that may accompany the use of natural materials may thus be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat.

Nos. 6,656,200, 5,874,500, 5,543,441, 5,514,379, 5,410, 016, 5,162,430, 5,324,775, 5,752,974, and 5,550,187.

The reaction conditions for forming crosslinked polymeric hydrogels from first and second precursors may depend on the nature of the reactive precursor used as well as the surrounding environment. The first and second precursors may be stable and/or non-reactive at a given pH as they are encased within oxidized cellulose and/or another biodegradable polymer, but become reactive upon exposure the pH of the tissue pH. In embodiments, reactions may be conducted in buffered aqueous solutions at a pH of about 5 to about 12. Buffers include, for example, sodium borate buffer (pH 10) and triethanol amine buffer (pH 7). In some embodiments, organic solvents such as ethanol or isopropanol may be added to improve the reaction speed of the first and second precursors.

In embodiments, the multi-encapsulated microspheres may incorporate any other in situ polymerizable monomers suitable for forming biocompatible tissue implants, hydrogels and/or adhesives, such as α-cyanoacrylate monomers, 1,1-disubstituted ethylene monomers, combinations thereof, and the like.

Microspheres (e.g., single or multi-encapsulated microspheres) according to the present disclosure may also incorporate one or more magnetic materials allowing for guidance of the encapsulated microspheres through a patient's body. Magnetic materials may be encapsulated into single or multi-encapsulated microspheres using the methods and techniques described above with respect to bioactive agents. Multi-encapsulated microspheres may include magnetic materials encapsulated therein along with bioactive agents, visualization agents, cross-linking precursors, radioactive materials, and combinations thereof, as discussed in more detail below with respect to FIGS. 2, 3, 6, and 9. Multi-encapsulated microspheres permit sequestration of magnetic materials from other substances (e.g., bioactive agents, visualization agents, etc.) contained in the microspheres, thereby allowing for magnetic guidance of the microspheres to the tissue site of interest as described in further detail below.

Multi-encapsulated microspheres may be guided to a treatment site by injecting or otherwise delivering the microspheres into the patient (e.g., intravenously, orally, etc.). After delivery of the microspheres, the treatment site is subjected to one or more magnetic fields, which may be generated by any suitable permanent or temporary magnets (e.g., electromagnets). The magnetic fields retain the microspheres circulating through the patient within the treatment site, i.e., the area to which magnetic field is applied. The microspheres thereafter begin to biodegrade, delivering the materials encapsulated therein to the treatment site. Magnetic guidance allows for the concentration of bioactive agents at a predetermined target site, and away from other sites of the patient within healthy tissue.

Magnetic guidance provides for delivery of microspheres to specific locations in the body which are hard to reach using conventional delivery mechanisms (e.g., catheters). Magnetic guidance is possible with more than one layer of encapsulation containing a magnetic payload, thus allowing for more than one occasion of magnetic guidance as the layers erode and/or diffuse. The use of oxidized cellulose also lowers the possibility of rusting of the magnetic payload (e.g., iron containing payload) since the process of encapsulation in oxidized cellulose is an oil-in-oil process, i.e., a non-aqueous process. Magnetic Resonance Imaging (MRI) may also be facilitated with the magnetic materials. Complementary properties of more than one MRI agent could be combined in the same formulation because of the multiple layers of encapsulation.

With reference to FIG. 2, the multi-encapsulating microsphere 20 encapsulates a plurality of microspheres 22 therein. The microspheres 22 include one or more bioactive agents, visualization agents, and/or cross-linking precursors described above. The multi-encapsulating microsphere 20 further includes one or more magnetic materials.

With reference to FIG. 3, a doubly-encapsulating microsphere 30 includes a microsphere 32, which further encapsulates microsphere 34 as described in more detail above. In one embodiment, the microsphere 30 may include a first bioactive agent, visualization agent, and/or cross-linking precursor described above. The microsphere 32 includes a second bioactive agent, visualization agent, and/or cross-linking precursor. The microsphere 34 includes one or more magnetic materials. Encapsulation of the magnetic materials in the furthest encapsulated microsphere 34, allows for the magnetic materials to remain at the treatment site while doubly-encapsulating microsphere 30 degrades thereby releasing the first bioactive agent, visualization agent, and/or cross-linking precursor followed by the degradation of the single-encapsulating microsphere 34 thereby releasing the second bioactive agent, visualization agent, and/or cross-linking precursor.

With reference to FIG. 6, multi-encapsulating microsphere 40 is shown. The microsphere 40 includes one or more first microspheres 42 and one or more second microspheres 44. The first microspheres 42 may possess one or more bioactive agents, visualization agents, and/or cross-linking precursors described above.and the second microspheres 44 include one or more magnetic materials. Microspheres 42 and 44 may be encapsulated in the same layer or in multiple layers, which may be the same or different.

In embodiments, the microsphere 44 may also include magnetic materials, which allows for multiple opportunities of magnetic guidance. In particular, the microspheres 40 may be guided to a first treatment site, where the microsphere 40 degrades, thereby releasing the microspheres 42 and 44. The microspheres 42 remain in place, thereby releasing payload, while the microspheres 44, which include magnetic materials may be guided to a second treatment site. The microspheres 44 may optionally include a second bioactive agent, visualization agent, and/or cross-linking precursor described above. Once at the second treatment site, the microspheres 44 degrade thereby releasing its own payload.

Figure 9:
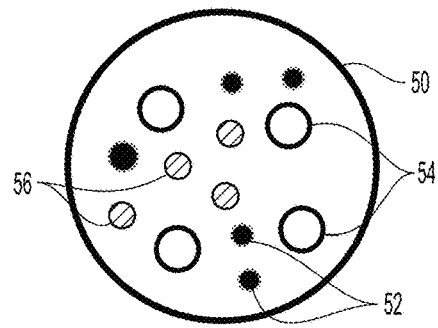
FIG. 9 is a schematic diagram of a multi-encapsulated microsphere including three types of microspheres in accordance with the present disclosure.

With reference to FIG. 9, another embodiment a multi-encapsulating microsphere 50 is shown. The microsphere 50 includes one or more first microspheres 52, one or more second microspheres 54, and one or more third microspheres 56. The first microspheres 52 may include one or more bioactive agents, the second microspheres 54 may include one or more magnetic materials, and the third microspheres 56 may include a visualization agent, or any other suitable material. The first microsphere 52, second microsphere 54, and third microsphere 56 may be formed separately prior to encapsulation within the microsphere 50. Microspheres 52, 54, 56 may be encapsulated in the same layer or in multiple layers, which may be the same or different.

Where utilized, suitable magnetic materials may be in particle form having a size from about 10 angstroms (Å) to about 1000 Å, in embodiments from about 25 Å to about 500 Å. Suitable magnetic materials may be temporary magnetic materials or permanent magnetic materials, ceramic, crystalline, or flexible magnetic materials (e.g., a polymeric substance such as thermoplastics or rubber) combined with magnetic ferrite (e.g., heat-treated mixtures of oxides of iron and one or more other metals having complex crystals with magnetic properties). Suitable magnetic materials include, but are not limited to, ferrite, strontium ferrous oxide, neodymium (NdFeB, optionally including dysprosium), samarium, cobalt, aluminum, nickel, copper, iron, titanium, and combinations thereof. In embodiments, the microspheres 22 may include magnetotactic bacteria having magnetosomes allowing the bacteria to orient within a magnetic field. In further embodiments, the magnetic material may be an alloy of a radioactive material such as yttrium-90, which is a β-emitter, making it suitable for radiation therapy treatment of various cancers as described in further detail below.

Microspheres (e.g., single or multi-encapsulated microspheres) according to the present disclosure may also incorporate one or more radioactive materials allowing the microspheres to be used in interventional oncology (e.g., radiotherapy). Radioactive materials may be encapsulated into single or multi-encapsulated microspheres using the methods and techniques described above with respect to bioactive agents. Suitable radioactive materials include, but are not limited to, yttrium (e.g., $^{90}$Y), iodine (e.g., $^{131}$I), holmium (e.g., $^{166}$Ho), combinations thereof, and the like. Microspheres containing radioactive materials may be formed by encapsulating the materials as described above. In embodiments, radioactive materials may be encapsulated in oxidized cellulose to form singly-encapsulated microspheres. In embodiments, the oxidized cellulose microspheres including radioactive materials may be further encapsulated in successive oxidized cellulose microspheres.

Once microspheres are formed, they are subjected to neutron bombardment prior to implantation within the patient to convert stable isotopes of the materials into radioactive materials suitable for radiotherapy (e.g., converting inert $^{89}$Y into $^{90}$Y). The microspheres may be guided to the treatment site using any suitable methods (e.g., magnetic guidance as described above if magnetic materials are present). The microspheres may then deliver radiation therapy to the treatment site.

Neutron bombardment and/or other treatments may heat the microspheres up to 200° C., which causes degradation of many biodegradable polymers used to create microspheres, such as polylactide. Accordingly, conventional microspheres for delivering radioactive metals have been formed from non-biodegradable materials, such as glass. The present disclosure provides for single or multi-encapsulated microspheres formed from oxidized cellulose, which is a polymer capable of withstanding temperatures up to 200° C. Unlike glass microspheres, the microspheres of the present disclosure provide for delivery of the radioactive materials using biodegradable microspheres that degrade over time. Glass microspheres including radioactive materials are disclosed in S. Ho et al., "Clinical Evaluation Of The Partition Model For Estimating Radiation Doses From Yttrium-90 Microspheres In The Treatment Of Hepatic Cancer Evaluation Of The Partition Model For Estimating Radiation Doses From Yttrium-90 Micro Spheres In The Treatment Of Hepatic Cancer," European Journal of Nuclear Medicine, Vol. 24, No. 3, (March 1997), pp. 293-298.

Microspheres made with oxidized cellulose are lower in density than glass microspheres, which is an advantage for interventional oncology applications because high density microspheres result in intravascular settling. With respect to conventional encapsulation materials, multiple encapsulation of radioactive materials using oxidized cellulose as described herein prevents seepage and leakage of radioactive materials from the microspheres.

Microspheres (e.g., single or multi-encapsulated microspheres) according to the present disclosure may also incorporate one or more endothermic or exothermic agents. Endothermic or exothermic agents may be encapsulated into single or multi-encapsulated microspheres using the methods and techniques described above with respect to bioactive agents. Endothermic and/or exothermic agents may be used in treatments where exothermic and endothermic reactions (e.g., oncology) are desired, especially in an in situ setting, where the timing and anatomical location of such heat-producing or heat-absorbing reactions can be controlled and manipulated to heat and/or cool tissue, respectively. Multi-encapsulated microspheres allow for control over timing and anatomical location of endothermic and/or exothermic reactions. In other words, the use of the multi-encapsulated oxidized cellulose formulations allows control over the use of heat-produce or heat-removing reactions, as the reactants are compartmentalized. The actual production or removal of heat occurs only upon a breakdown of the encapsulating polymer, thus bringing the reactive components into contact as described in further detail below.

Exothermic agents include a first exothermic reactant and a second exothermic reactant. When the first and second reactants react heat is generated by the reaction into the surrounding tissue. Suitable first and second exothermic reactants include, but are not limited to, acids, salts, water, calcium oxide, and combinations thereof.

Endothermic agents include a first endothermic reactant and a second endothermic reactant. When the first and second reactants react heat is withdrawn by the reaction from the surrounding tissue. Suitable first and second endothermic reactants include, but are not limited to, ethanoic acid, sodium carbonate, calcium carbonate, and combinations thereof.

Endothermic or exothermic reactants may be combined to produce an endothermic reaction, an exothermic reaction, or both, respectively. Suitable medical conditions for treatment with these endothermic and/or exothermic reactions include, for example, cancers (e.g., tumors), inflammation, infections, combinations, thereof, and the like.

In embodiments, tumors may be treated by application of heat, which destroys cancer cells. There are two modes of heat application for cancer treatment: hyperthermia and thermoablation. Hyperthermia involves heating of certain organs or tissues to temperatures from about 41° C. to about 48° C. Thermoablation generally involves heating tissues to temperatures from about 48° C. to about 56° C. Thermoablation is characterized by acute necrosis, coagulation, and/or carbonization of the tumor tissue due to the relatively higher temperatures involved. Heat is conventionally delivered by electrosurgical energy, resistive heating, microwave energy, heated fluid, combinations thereof, and the like. To compensate for the heat supplied to the tissue (e.g., limit heat application to the tumor) and prevent damage to surrounding healthy tissue, heat sinks (e.g., circulated coolant) may be supplied to the surrounding tissue and/or the device (e.g., catheter) being used during ablation.

In embodiments, the present disclosure provides for in situ delivery of exothermic and/or endothermic reactants/agents via oxidized cellulose microspheres (e.g., multi-encapsulated formulations) within and outside the tumor, respectively. In embodiments, either one or both of the exothermic and endothermic agents may be delivered while heating and/or cooling is supplied or removed by other suitable methods (e.g., energy ablation, coolant circulation, etc.).

With reference to FIG. 6, a multi-encapsulating microsphere 40 is shown, having one or more first microspheres 42 including a first endothermic or exothermic reactant and one or more second microspheres 44 including a second endothermic or exothermic reactant. After implantation, the microspheres 40, 42, and 44 prevent immediate reaction of the first and second endothermic or exothermic reactants. After degradation of the microsphere 40, the microspheres 42 and 44 subsequently degrade, thereby releasing the first and second endothermic or exothermic reactants, which then react in exothermic or endothermic fashion to heat or cool tissue as described above. In embodiments, the microsphere 40 may also include one or more initiators.

Figure 10:
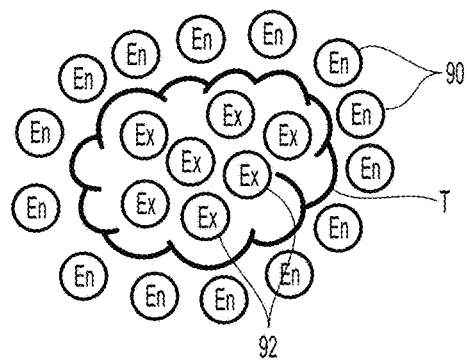
FIG. 10 is a schematic diagram depicting treatment of a tumor with multi-encapsulated microspheres including endothermic and exothermic reactants in accordance with the present disclosure.

With reference to FIG. 10, the microspheres 40 possessing microspheres 42 and 44 are implanted within and/or around the tissue region (e.g., tumor T). In embodiments, exothermic microspheres 92, for example, microspheres 40 possessing microspheres 42 and 44 including first and second exothermic reactants, respectively, are implanted within the tumor boundary of the tumor T. Endothermic microspheres 90, namely, microspheres 40 possessing microspheres 42 and 44 including first and second endothermic reactants, respectively, are implanted on the periphery of the tumor T with cooling of the surrounding tissue. This allows for enhanced heating within the tumor boundary and active cooling outside the tumor boundary.

In embodiments, in situ exothermic and endothermic reactions may be timed along with initiation of thermal ablation in the tumor, such that the exothermic reaction within the tumor enhances the effect of the thermal ablation, while the endothermic reaction outside the tumor protects the healthy tissue. In further embodiments, heating may be accomplished using conventional hyperthermia or ablation devices, with microspheres 40, 42, and 44 being used to deliver endothermic reactants around the tissue to cool tissue. In further embodiments, cooling may be accomplished using conventional cooling techniques, with microspheres 40 being used to deliver exothermic reactants into the tissue to heat tissue.

Microspheres (e.g., single or multi-encapsulated microspheres) according to the present disclosure may also incorporate one or more magnetic materials allowing for guidance of the encapsulated microspheres containing endothermic and/or exothermic reactants through a patient's body. Multi-encapsulated microspheres may be guided to a treatment site by injecting or otherwise delivering the microspheres into the patient (e.g., intravenously, orally, etc.). After delivery of the microspheres, the treatment site is subjected to one or more magnetic fields, which may be generated by any suitable permanent or temporary magnets (e.g., electromagnets). The magnetic fields retain the microspheres circulating through the patient within the treatment site, i.e., the area to which magnetic field is applied. The microspheres thereafter begin to biodegrade, delivering the materials encapsulated therein to the treatment site. Magnetic guidance allows for the concentration of endothermic or exothermic agents at a predetermined target site, and away from other sites of the patient (e.g., reticular endothelial system).

In other embodiments, oxidized or modified cellulose microspheres according to the present disclosure may be used in embolization procedures, including those used in interventional oncology. Oxidized cellulose's hemostatic properties make it useful in embolization applications, since the oxidized cellulose does not occlude the vasculature prior to contacting blood therein. In particular, oxidized cellulose provides a superior mechanism for embolization than conventional embolic agents, such as polyvinyl alcohol, which works primarily through mechanical action combined with inflammation and granulation of surrounding tissue.

Embolization involves selective, e.g., either partial or full, occlusion of blood vessels to prevent blood flow to an organ, tumor, or any other desired segment of tissue. Vessel embolization may be used in a variety of medical procedures including, but not limited to, controlling bleeding caused by trauma, prevention of profuse blood loss during dissection of blood vessels, obliteration of an organ or a portion thereof, blocking of blood flow into abnormal blood vessels, and the like. Embolization may be used to treat a variety of conditions by stopping or controlling blood flow including, but not limited to, hymoptysis, arteriovenous malformations, cerebral aneurysms, gastrointertinal bleeding, epistaxis, hemorrhages, fibroids, lesions, and/or tumors. As used herein the term "embolization microsphere" refers to any particle formed from oxidized cellulose used to artificially block any biological lumen including but not limited to, blood vessel, fallopian tubes, bile ducts, tear ducts, lymph ducts, vas deferens.

During use, the embolization microspheres may be implanted within the blood vessels using an implantation device, such as a catheter or syringe, to access the blood vessels. Insertion of the implantation device may be guided using any suitable imaging techniques, such as digital subtraction angiography, fluoroscopy, and the like. Once the implantation device is at the treatment site, the embolization microspheres are injected into the blood vessel to partially or fully occlude the blood vessel thereby stopping or decreasing the blood flow.

Figure 11:
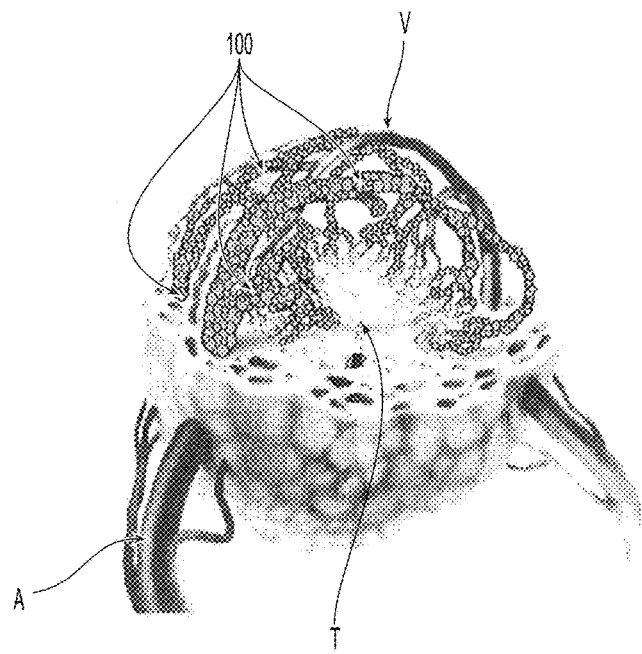
FIG. 11 is a diagram of treatment of a tumor with embolization microspheres in accordance with the present disclosure.

As noted above, in embodiments microspheres of the present disclosure may be used to disrupt blood flow to organs or tumors. With reference to FIG. 11, a tumor mass "T" is shown having one or more arterial blood vessels "A" and venous blood vessels "V." During embolization, a plurality of embolization microspheres 100 are implanted into the arterial blood vessel "A" using the implantation device (not shown). The embolization microspheres may be suspended in an aqueous or a lipid-based media to aid in storage and implantation. After embolization microspheres are implanted, they are set in place within the blood vessels and swell by absorbing surrounding fluids. Swelled microspheres occlude the blood flow within the blood vessels. Over time, the embolization microspheres hydrolyze and ultimately breakdown into glucose and glucuronic acid, which are then metabolized within the body.

The embolization microspheres may be formed as single or multi-encapsulated microspheres as described with respect to FIGS. 2, 3, 6, and 9. The embolization microspheres may include one or more optional bioactive agents useful in the embolization procedures, including, but not limited to hemostatic agents, radioactive materials, chemotherapeutics, and combinations thereof.

In embodiments, the embolization microspheres may include radio-protective materials to provide for protection from local radiation-based treatments as well as systemic sources of radiation. Suitable radio-protective material include, but are not limited to, Yttrium-90, Iodine-125, Iridium-192, Ruthenium-106, Cobalt-60, Palladium-103, Caesium-137, and combinations thereof. In further embodiments, embolization microspheres may be multi-encapsulated microspheres as described with respect to FIGS. 3, 6, and 9 and may include first encapsulated microspheres (e.g., microspheres 32, 42, 52) having a radio-protective material and second encapsulated microspheres (e.g., microspheres 34, 44, 54) having the radioactive materials. The first microspheres may degrade at a faster degradation rate to disperse the radio-protective material throughout the implantation site prior to radioactive material being dispersed from the second microspheres, which limits exposure of healthy tissue to radiation. In embodiments, microspheres containing the radio-protective materials may be implanted around the tumor, similar to the microspheres 90 of FIG. 10, with the microspheres containing the radioactive material, such as the microspheres 92 of FIG. 10, being implanted within the tumor T.

Embolization microspheres may be formed according to any of the above-described oil-in-oil emulsion solvent extraction processes, in which the solvent of the oxidized cellulose solution, NMP, is extracted by separation of two or more oils that are immiscible or insoluble with the solvent, e.g., mineral and cottonseed oils. Suitable oils include, but are not limited to, petroleum-based oils, such as light, medium or heavy mineral oils (e.g., mixtures of alkanes having from about 40 carbons to about 60 carbons), plant-based oils, such as cottonseed oil, silicone-based oils, and combinations thereof. In embodiments, two or more oils may be a heavy oil and a light oil, that compete for extraction of the solvent. In embodiments, the heavy oil and the light oil may be present at a ratio of from about 1:10 to about 10:1, in embodiments from about 1:3 to about 3:1.

Microspheres may be formed of any suitable size. In embodiments, microspheres may have a diameter from about 0.001 micrometers (μm) to about 3,000 μm, in embodiments from about 0.1 μm to about 1,000 μm, in further embodiments from about 10 μm to about 500 μm. The size, rate of swellability, and rate of degradation of the embolization microspheres may be controlled by adjusting the ratio and viscosity of the oils being used in the solvent extraction process and the rate of stirring. Emulsion-based solvent extraction may be accomplished by stirring the suspension or emulsion at a rate from about 25 rpm to about 60,000 rpm, in embodiments, from about 100 rpm to about 15,000 rpm, in further embodiments from about 250 rpm to about 5,000 rpm. The emulsion may be stirred for a period of time from about 5 seconds to about 4 hours, in embodiments, from about 15 seconds to about 1 hour.

As noted above, in embodiments the oxidized cellulose microspheres according to the present disclosure may be used as part of a liquid embolic composition. The liquid embolic composition may include a liquid delivery vehicle, which may be a solution of a water-insoluble, biocompatible polymer dissolved in an organic solvent. Suitable polymers include ethylene vinyl alcohol, polyvinyl formal, polyvinyl alcohol-vinyl formal, polyethylene vinyl formal, and combinations thereof. Suitable solvents include any organic class 2 solvent as classified by the International Conference on Harmonization that has been approved for subcutaneous injection, such as NMP, dimethyl sulfoxide, and combinations thereof. The embolization microspheres may be any suitable type described above, e.g., multi-encapsulated. In embodiments, the liquid delivery vehicle and/or the oxidized cellulose microspheres may include one or more optional visualization and/or bioactive agents useful in the embolization procedures, including, but not limited to, hemostatic agents, radioactive materials, chemotherapeutics, and combinations thereof.

In embodiments, the liquid embolic composition may be provided as part of a kit. The kit may include a plurality of vials or other suitable containers for storing the liquid delivery vehicle, the embolization microspheres, and one or more optional visualization and/or bioactive agents (in addition to the ones included in the delivery vehicle and/or the microspheres). The liquid embolic composition may be mixed prior to delivery by combining the contents of each of the vials pursuant to accompanying instructions providing directions for formulating the liquid embolic composition.

Figure 12:
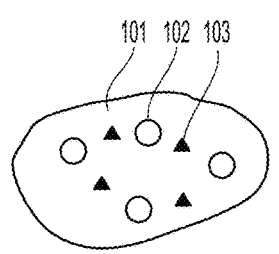
FIG. 12 is a schematic diagram of a liquid embolic composition having a visualization agent and oxidized cellulose microspheres in accordance with the present disclosure.
Figure 13:
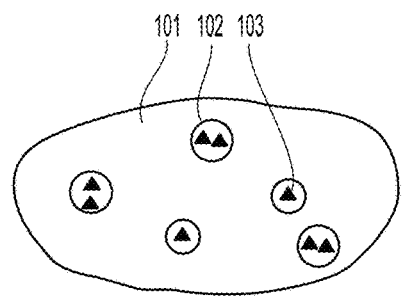
FIG. 13 is a schematic diagram of a liquid embolic composition having oxidized cellulose microspheres with a visualization agent in accordance with the present disclosure.
Figure 14:
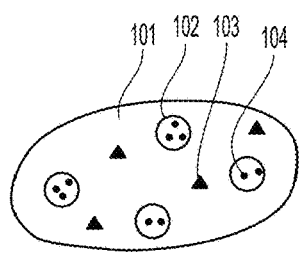
FIG. 14 is a schematic diagram of a liquid embolic composition having a visualization agent and oxidized cellulose microspheres with a bioactive agent in accordance with the present disclosure.
Figure 15:
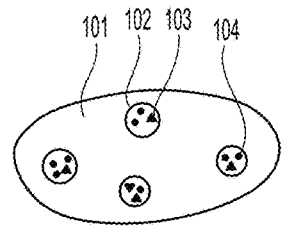
FIG. 15 is a schematic diagram of a liquid embolic composition having oxidized cellulose microspheres with a visualization agent and a bioactive agent in accordance with the present disclosure.
Figure 16:
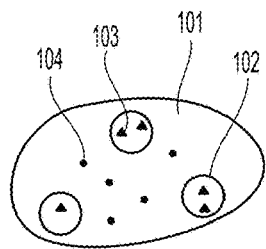
FIG. 16 is a schematic diagram of a liquid embolic composition having a bioactive agent and oxidized cellulose microspheres with a visualization agent in accordance with the present disclosure.
Figure 17:
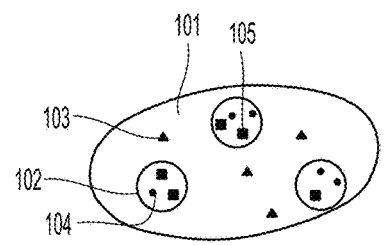
FIG. 17 is a schematic diagram of a liquid embolic composition having a visualization agent and oxidized cellulose microspheres with a plurality of bioactive agents in accordance with the present disclosure.

The liquid embolic composition may include any suitable combination of a liquid delivery vehicle 101, embolization microspheres 102, and one or more optional visualization 103 and/or bioactive agents 104 and 105 as shown in FIGS. 12-17. The liquid embolic composition may include the visualization agent 103 within the liquid delivery vehicle 101 along with the microspheres 102 as shown in FIG. 12. In embodiments, the visualization agent 103 may be included in the microspheres 102 as shown in FIG. 13. In embodiments, the microspheres 102 may include the bioactive agent 104 and the liquid delivery vehicle 101 may include the visualization 103 agent as shown in FIG. 14. In further embodiments, the microspheres 102 may include both the visualization agent 102 and the bioactive agent 103 (e.g., multi-encapsulated microspheres) as shown in FIG. 15. With reference to FIG. 16, the liquid delivery vehicle 101 may include the bioactive agent 104 and the microspheres 102 may include the visualization agent 103. In other embodiments, the liquid delivery vehicle 101 may include the visualization agent 103 and the microspheres 102 may include a plurality of bioactive agents 104 and 105 (e.g., multi-encapsulated microspheres) as shown in FIG. 17.

The present disclosure also provides for an embolization slurry including oxidized cellulose. The term "slurry" as used herein refers to a fluid mixture including a mobile (e.g., liquid) phase and a solid phase. The solid phase may have solids present in an amount from about 0.01% to about 60% by weight and/or volume of the slurry, in embodiments from about 0.1% to about 25% by weight and/or volume of the slurry, in further embodiments from about 1% to about 15% by weight and/or volume of the slurry. The solid phase may be formed from any suitable oxidized cellulose material, including fibers, microspheres, particulates, fragments, dissolved oxidized cellulose, oxidized cellulose suspension, oxidized cellulose emulsion, and combinations thereof.

In embodiments, the solid phase may include any suitable water soluble polymers including, but not limited to, polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"), poly(vinyl pyrrolidinone) ("PVP"), poly (amino acids), poly (saccharides) such as dextran, chitosan, alginates, carboxymethylcellulose, oxidized cellulose, hydroxyethylcellulose and/or hydroxymethylcellulose, hyaluronic acid, and proteins such as albumin, collagen, casein, and/or gelatin, and combinations thereof.

The liquid phase may include any suitable solvent that will suspend the solid or dissolved oxidized cellulose material, including, but not limited to, water, saline, serum, buffered aqueous solution(s), and combinations thereof. The liquid phase may also include one or more optional bioactive agents useful in the embolization procedures, including, but not limited to hemostatic agents, radioactive materials, chemotherapeutics, visualization agents, radio-protective agents, and combinations thereof.

In embodiments, the embolization slurry may be formed by contacting oxidized cellulose microspheres with the liquid phase (e.g., saline). The degradation rate of the oxidized cellulose within the slurry may be adjusted as described in further detail below (e.g., by adjusting the degree of oxidation of the oxidized cellulose, the amount of residual solvent in the oxidized cellulose microspheres, etc.). By controlling the size and/or distribution of the polymer fibers of the oxidized cellulose within the embolization slurry, non-targeted delivery of the embolization agent (e.g., oxidized cellulose) within the vasculature can be minimized. In embodiments, the oxidized cellulose slurry may include one or more optional visualization and/or bioactive agents useful in the embolization procedures, including, but not limited to, hemostatic agents, radioactive materials, chemotherapeutics, radio-protective agents, and combinations thereof.

During use, the embolization slurry may be implanted within the blood vessels using an implantation device, such as a catheter or syringe, to access the blood vessels. Insertion of the implantation device may be guided using any suitable imaging technique, such as digital subtraction angiography, fluoroscopy, and the like. Once the implantation device is at the treatment site, the embolization slurry is injected into the blood vessel to partially or fully occlude the blood vessel, thereby stopping or decreasing the blood flow.

The degradation rate of the embolization microspheres and the embolization slurry formed from oxidized cellulose may also be controlled by adjusting the degree of oxidation of the oxidized cellulose solution used to form the same. The degree of oxidation of oxidized cellulose of the microspheres and/or the slurry may be from about 0.2 to about 0.8, in embodiments from about 0.3 to about 0.7. The degree of oxidation may be controlled during the dissolution process of oxidized cellulose as described above.

The swellability rate may also be adjusted by crosslinking the microspheres and the slurry before or after implantation within the blood vessels. Cross-linking of the microspheres and the slurry reduces the swellability rate and the degradation rate of the microspheres and the slurry, allowing the microspheres and the slurry to be disposed within the blood vessels for longer periods of time, as well as limiting the swellable size of the microspheres. Suitable cross-linking agents for cross-linking embolization microspheres and the slurry may be any of the above-discussed cross-linking agents and include, but are not limited to, a solution of multivalent cations (e.g., about 2% by weight aqueous solution of calcium chloride), chitosan (e.g., about 5% by weight solution of chitosan in acetic acid), carboxymethyl-cellulose, acrylic polymers, a Schiff-base compound, trilysine, albumin, polyethylene glycol amine, water, saline, phosphate buffered saline, and combinations thereof. The cross-linking agent may be supplied to the implantation site (e.g., blood vessel) after the embolization microspheres or the slurry have been implanted to secure the microspheres in place. In embodiments, the cross-linking agent may be mixed with the microspheres or the slurry prior to implantation, allowing the cross-linking agent to bind the oxidized cellulose following implantation. In further embodiments, the oxidized cellulose solution may include one or more bioactive agents, visualization agents, radioactive materials, and other payloads described herein allowing for visualization and treatment of tumors and other tissues.

The embolization microspheres and the slurry according to the present disclosure provide a number of advantages over conventional embolization particles, which are formed from non-biodegradable materials (e.g., non-resorbable polymers, glass, etc.). Oxidized cellulose and NMP have well-established biocompatibility. In particular, oxidized cellulose is used in a variety of implantable medical devices approved by the U.S. Food and Drug Administration. NMP is a class 2 solvent as classified by the International Conference on Harmonization and has been approved for subcutaneous injection and other in situ uses (e.g., gel formation), which makes it well-suited for forming embolization microspheres. In addition to being biodegradable, the embolization microspheres and the slurry according to the present disclosure may have a tailored degradation, dissolution, and/or swellability rate. This allows for greater control in occluding blood vessels and prevents damage to surrounding tissue as the microspheres and the slurry fully degrade and once again permit blood flow through the vessel in which they were introduced.

The rate of degradation may be adjusted by modifying the degree of oxidation of the oxidized cellulose and the amount of the solvent present in the oxidized cellulose solution. Adjustment of the degree of oxidation affects the rate of biodegradation of the polymer back bone, eventually resulting in the dissolution of the microspheres and the slurry. Adjustments to the degree of oxidation affect medium to long-term degradation profile of the microspheres and the slurry (e.g., from about one day to several weeks). Adjustment of the amount of solvent affects the residual solvent remaining in the microspheres, which can be leveraged to control the rate of dissolution of these microspheres over short-term (e.g. from about 30 seconds to about 12 hours). The oxidized cellulose microspheres and the slurry according to the present disclosure may have a degradation time from about 5 minutes to about 8 weeks, in embodiments from about 12 hours to about 2 weeks. The degree of oxidation of oxidized cellulose of the embolization microspheres and the slurry in accordance with the present disclosure may be from about 0.2 to about 1.0, in embodiments from about 0.3 to about 0.9, in further embodiments from about 0.5 to about 0.7. The solvent may be present in an amount of from about 0.1% by weight to 25% by weight of the oxidized cellulose present in the microspheres and the slurry, in embodiments from about 0.5% by weight to about 10% by weight of the oxidized cellulose.

The adjustment to the degradation profile allows for use of the solutions according to the present disclosure in temporary or transient embolization procedures, which are rapidly emerging as an attractive alternative to the more traditional permanent embolization approach for tumor treatment and other conditions. Oxidized cellulose solutions offer distinct advantages, and significantly greater control than other embolization technologies due to adjustable degradation, dissolution, and/or swellability rates since oxidized cellulose offers a wide spectrum in terms of the kinetics of degradation as described above.

The present disclosure allows a variety of drugs to be loaded into oxidized cellulose based formulations at the time of use. As oxidized cellulose has groups possessing a negative charge (e.g. carboxylic acid groups), it also has the potential for high loading of positively charged drug molecules without the need for any additional derivatization or functionalization.

In embodiments, oxidized cellulose solutions may be loaded with bioactive agents at the time of use, e.g., in the operating room. This allows for the practitioner to select any desired bioactive agent or combinations of bioactive agents incorporated into the solution, which then may be used in various procedures. In addition, the rate of degradation of the oxidized cellulose polymer may also be tailored (for example by changing the degree of oxidation of the oxidized cellulose) in order to provide a suitable release rate of bioactive agents, e.g., sustained release, bolus release, or combinations thereof. Accordingly, the choice of bioactive agents, their loading amount, as well as their release rate may be customized for each patient and/or treatment at the time of use.

Bioactive agent loading may occur from about 1 minute to about 3 hours prior to use, in embodiments from about 30 minutes to about 1 hour prior to use. Oxidized cellulose microspheres and/or slurry may be preloaded with additional bioactive agents, visualization agents, cross-linking precursors, magnetic materials, radioactive materials, radio-protective materials, and combination thereof.

As noted above, an oxidized cellulose slurry in accordance with the present disclosure may include oxidized cellulose fibers as well as particulates. Because oxidized cellulose may be converted into particulate form, it offers the unique advantage of being used in a manner where both the polymer slurry form and the particulate form may be used together, leveraging the advantages of both these physical forms of the oxidized cellulose polymers.

In embodiments, the oxidized cellulose may be modified to form derivatized oxidized cellulose that is particularly suited for specific compounds, e.g., bioactive agents. This facilitates bioactive agent loading at the time of treatment, while at the same time offering the prospect of tunable sustained-release kinetics for the release of the bioactive agent. In embodiments, oxidized cellulose may be subjected to hydrophobic derivatization to allow the oxidized cellulose to chelate hydrophobic bioactive agents, e.g., paclitaxel. Hydrophobic derivatization may also include adding hydrophobic groups to the cellulose polymer backbone. Suitable hydrophobic groups which may be added include, but are not limited to, alkanes, phenols, and combinations thereof. In further embodiments, oxidized cellulose may be complexed with chelation enhancers to enhance ionic interactions with certain bioactive agents, for example, those which are metal-based (e.g. the cancer drugs cisplatin, carboplatin and/or oxaliplatin, which are platinum based). Suitable chelation enhancers include, but are not limited to, tripolyphosphates, sulfonates, and combinations thereof. Also included are macromolecular chelating agents, such as those targeting platinum.

In yet further embodiments, oxidized cellulose may be modified to provide for affinity-based derivatization, such that the bioactive agent (e.g., antibody, receptor, etc.) is attached to the oxidized cellulose polymer backbone, thus providing for affinity-based interaction. In embodiments, serum proteins exhibiting strong affinity to anticancer metal drugs may be immobilized on oxidized cellulose polymers and provide controlled release of the anticancer metal drugs. Suitable anticancer metal drugs include, but are not limited to, organometallic complexes of platinum, ruthenium, osmium, iridium, and combinations thereof.

In additional embodiments, oxidized cellulose may be derivatized to include stimuli-responsive functional groups, such as those that respond to changes in pH, light, and/or other parameters. Suitable pH sensitive functional groups include, but are not limited to, carboxylic acids, primary, secondary or tertiary amines, their salts, and combinations thereof. Suitable light sensitive functional groups include, but are not limited to, azobenzene, pyrene, nitrobenzene, and combinations thereof.

The present disclosure also provides for a liquid embolization solution including oxidized cellulose. The embolization solution according to the present disclosure may be used in embolization procedures, including those used in interventional oncology in a similar manner as described above with respect to oxidized cellulose microspheres and slurry. The embolization solution provides for effective embolization of a vessel while allowing for subsequent recanalization of the vessel based on biodegradable properties of the oxidized cellulose as described in further detail below.

The embolization solution may include oxidized cellulose dissolved according to the methods described above. Oxidized cellulose may be present in the solution in an amount from about 0.01% by weight to about 45% by weight of the solution, in embodiments, from about 1% by weight to about 30% by weight of the solution, in embodiments from about 5% by weight to 25% by weight of the solution, in embodiments from about 10% by weight to about 20% by weight of the solution. Suitable solvents include any organic class 2 solvent as classified by the International Conference on Harmonization that has been approved for subcutaneous injection, such as NMP, dimethyl sulfoxide, and combinations thereof. Since NMP is miscible with a wide range of solvents, both aqueous and organic, NMP offers significant flexibility in the choice of the final solvent system.

In embodiments, the oxidized cellulose solution may include one or more optional visualization and/or bioactive agents useful in the embolization procedures, including, but not limited to, bioactive agents, visualization agents, radioactive materials, hemostatic agents, chemotherapeutics, radio-protective agents, and other payloads described above allowing for visualization and treatment of tumors and other tissues.

The oxidized cellulose embolization solution according to the present disclosure displays thixotropic properties, which contribute to its ability to achieve effective embolization. As used herein the term "thixotropic" denotes decreasing viscosity of a composition in response to physical strain and increasing viscosity when the composition is left undisturbed. In particular, oxidized cellulose solution is a non-Newtonian fluid, and as a result has variable viscosity as a function of shear rate and/or time.

In other words, thixotropy is the change in viscosity due to subjecting a sample to shear forces. It is generally considered to be the shear thinning effect as viscosity falls within continuous shearing at a specific stress point, and is usually an indicator of breakup of structures within the fluid over time. Thixotropy also describes rebuilding of the system, e.g., the solution, within a predetermined time period as a disrupted system is restored after shearing.

Thixotropic properties of the soluble oxidized cellulose also allow for a wider variety of therapeutic agents to be loaded into the embolization solution according to the present disclosure compared to conventional embolic agents, e.g., PVA particles, which primarily rely on electrostatic interactions to encapsulate therapeutic agents.

During use, the embolization solution may be implanted within the blood vessels using an implantation device, such as a catheter or syringe, to access the blood vessels. Insertion of the implantation device may be guided using any suitable imaging techniques, such as digital subtraction angiography, fluoroscopy, and the like. Once the implantation device is at the treatment site, the embolization solution is injected into the blood vessel to partially or fully occlude the blood vessel, thereby stopping or decreasing the blood flow. Oxidized cellulose also has the ability to undergo significant swelling upon hydration, which contributes to its ability to achieve effective embolization.

Recanalization time, which denotes the duration of the embolism, may also be customized based on the properties of the oxidized cellulose to achieve desired embolization duration. The recanalization time may be adjusted by modifying the amount of the solvent in the solution as well as the amount and density of oxidized cellulose, among other variables. In embodiments, the recanalization time may be from about 1 minute to permanent status, e.g., non-degradable.

In embodiments, recanalization time may also be adjusted by modifying the degradation rate of the oxidized cellulose of the embolization solution. The degradation rate of the oxidized cellulose within the solution may be adjusted by modifying the degree of oxidation and/or molecular weight distribution of the oxidized cellulose used to form the embolization solution. The degree of oxidation of oxidized cellulose of the solution may be from about 0.2 to about 0.8, in embodiments from about 0.3 to about 0.7. The degree of oxidation may be controlled during the dissolution process of oxidized cellulose as described above.

Customizable recanalization makes it possible to pursue embolization applications for a wide spectrum of embolization treatments that require different periods of recanalization. Rapid recanalization may be from about 1 minute to about 24 hours and may be used to mitigate bleeding in the case of trauma patients, and for some interventional oncology applications including, but not limited to, trans-arterial embolization (TAE) and trans-arterial chemo embolization (TACE). Medium term recanalization may be from about 1 hours to about 7 days and may be used to perform uterine fibroid embolization (UFE) and in some interventional oncology applications, e.g., TAE and TACE. Long term recanalization may be from about 7 days to about 4 weeks and may be used to treat UFE and in some interventional oncology applications, e.g., TAE and TACE. Permanent embolization may be used in neurological interventional applications including, but not limited to, embolization treatments of brain tumors, aneurysms, and/or arterio-venous malformations (AVM).

In addition to controlling the recanalization time, the ability to recanalize embolized vessels in customizable windows of time also allows for treatment of the same vessel and/or tissue region multiple times when using drug-loaded embolic agents. In contrast, permanent embolic agents may only be used once due to the permanently formed occlusion.

Oxidized cellulose includes several properties which make it useful as an embolization agent. Oxidized cellulose has hemostatic properties, which provide a superior targeted mechanism of action with minimal inflammation and tissue granulation in comparison to existing embolic agents such as PVA, which primarily operate through mechanical action and induce inflammation and granulation of tissue.

In addition, the liquid oxidized cellulose embolization solution according to the present disclosure provides a number of advantages over other conventional embolization compositions. As noted above, oxidized cellulose may be used to provide a non-permanent, biodegradable embolization as compared with permanent embolization compositions such as cyanoacrylates or ethylene vinyl alcohol copolymers. In particular, oxidized cellulose does not suffer from the disadvantage of cyanoacrylates, which have a high risk of non-targeted embolization due to inadvertent contact with ionic fluids. Moreover, no other liquid embolic agents offer the ability to tailor the time for recanalization, as provided by the liquid oxidized cellulose embolization solution according to the present disclosure.

Moreover, oxidized cellulose is highly biocompatible, which is a significant advantage in embolic applications, especially when temporary embolization is desired. The biocompatibility of oxidized cellulose also provides better outcomes when the occlusion has been dissolved and expeditious healing of the vasculature is desired.

A liquid oxidized cellulose embolization solution according to the present disclosure also provides for improved penetration of vessels, complete filling of embolization targets, improved ability to flow through complex vascular structures, and adjustable viscosity. Viscosity of the embolization solution may also be modified by adjusting the concentration of the soluble oxidized cellulose, namely, modifying the weight/volume ratio of the oxidized cellulose in solution. In embodiments, the embolization solution may be formed just prior to injection to achieve an embolization solution having desired properties. This may include, but is not limited to, adjusting the amount of oxidized cellulose, loading various therapeutic agents described above, and adjusting the dosage of the therapeutic agents.

The liquid oxidized cellulose embolization solution according to the present disclosure is also useful in preventing non-targeted particulate embolization. Since in embodiments the embolization solution may only include soluble oxidized cellulose, non-targeted delivery of any insoluble or particulate embolic agent within the vasculature is eliminated. This provides an advantage over any polymer particulate or microsphere embolization agents, which may result in inadvertent delivery of embolization particles to non-targeted vessels.

Another advantage of the liquid oxidized cellulose embolization solution is its ability to achieve recanalization of vessels based on hydrolysis-driven biodegradation rather than enzymatic degradation of starch-based embolic solutions, e.g., those that include chitosan-CMC compositions. A hydrolysis-driven biodegradation process is advantageous over enzymatic biodegradation processes since it provides greater control over the degradation rate as well as a lack of dependence on the presence of endogenous or exogenous enzymes.

The advantages of the liquid oxidized cellulose embolization solution according to the present disclosure are believed to be due, in part, to the distinct mechanism of phase transition for soluble oxidized cellulose, driven by its hemostatic, thixotropic and swelling properties as well as the rate of degradation of oxidized cellulose being amenable to modulation by adjustments to the degree of oxidation and the molecular weight distribution of oxidized cellulose. Thus, the liquid oxidized cellulose embolization solution provides an effective liquid and biodegradable embolic agent due to a combination of its thixotropic, hemostatic and swelling properties as described above.

In addition to embolization, the thixotropic properties of oxidized cellulose solutions according to the present disclosure make them suitable for use in a variety of medical applications. As noted above, thixotropic fluids exhibit decreasing viscosity in response to physical strain and increasing viscosity when left undisturbed. Thus, due to their thixotropic nature, the oxidized cellulose solutions are flowable, when the solutions are agitated or otherwise subjected to shear forces, and increase in viscosity when at rest, namely, when the solutions are free from any shear forces.

Solutions of fully solubilized oxidized cellulose according to the present disclosure possesses some very unique and beneficial properties due to its complete dissolution and high degree of oxidation as opposed to non-oxidized cellulose, such as the ability to undergo non-enzymatic hydrolysis driven biodegradation. Thixotropic oxidized cellulose solutions disclosed herein are non-obvious, because thixotropic properties manifest themselves when the oxidized cellulose is well oxidized and solubilized, and do not manifest itself when the oxidized cellulose is not properly solubilized or oxidized as described in further detail below with respect to Example 23 and FIGS. 40 and 41. As used herein "fully solubilized oxidized cellulose" denotes oxidized cellulose that has been dissolved according to the processes described above and in the Examples below such that the resulting solution possesses no solid particles detectable under visual observation. In embodiments, thixotropic oxidized cellulose solutions according to the present disclosure include oxidized cellulose that is fully solubilized and has a degree of oxidization from about 0.35 to about 0.95, in embodiments 0.5 to about 0.8, in further embodiments from about 0.6 to about 0.7. The dissolution processes according to the present disclosure allow for fully dissolving oxidized cellulose without adversely impacting the degree of oxidation or the molecular weight.

In embodiments, an oxidized cellulose solution may be formed in the manner described above by dissolving oxidized cellulose in a suitable solvent, such as N,N-Dimethylacetamide, N-methyl-2-pyrrolidinone (NMP), and combinations thereof. Oxidized cellulose may be present in the solution in an amount from about 0.01% by weight to 45% by weight of the solution, in embodiments from about 1% by weight to about 30% by weight of the solution, in embodiments from about 5% by weight to 20% by weight of the solution.

Figure 39:
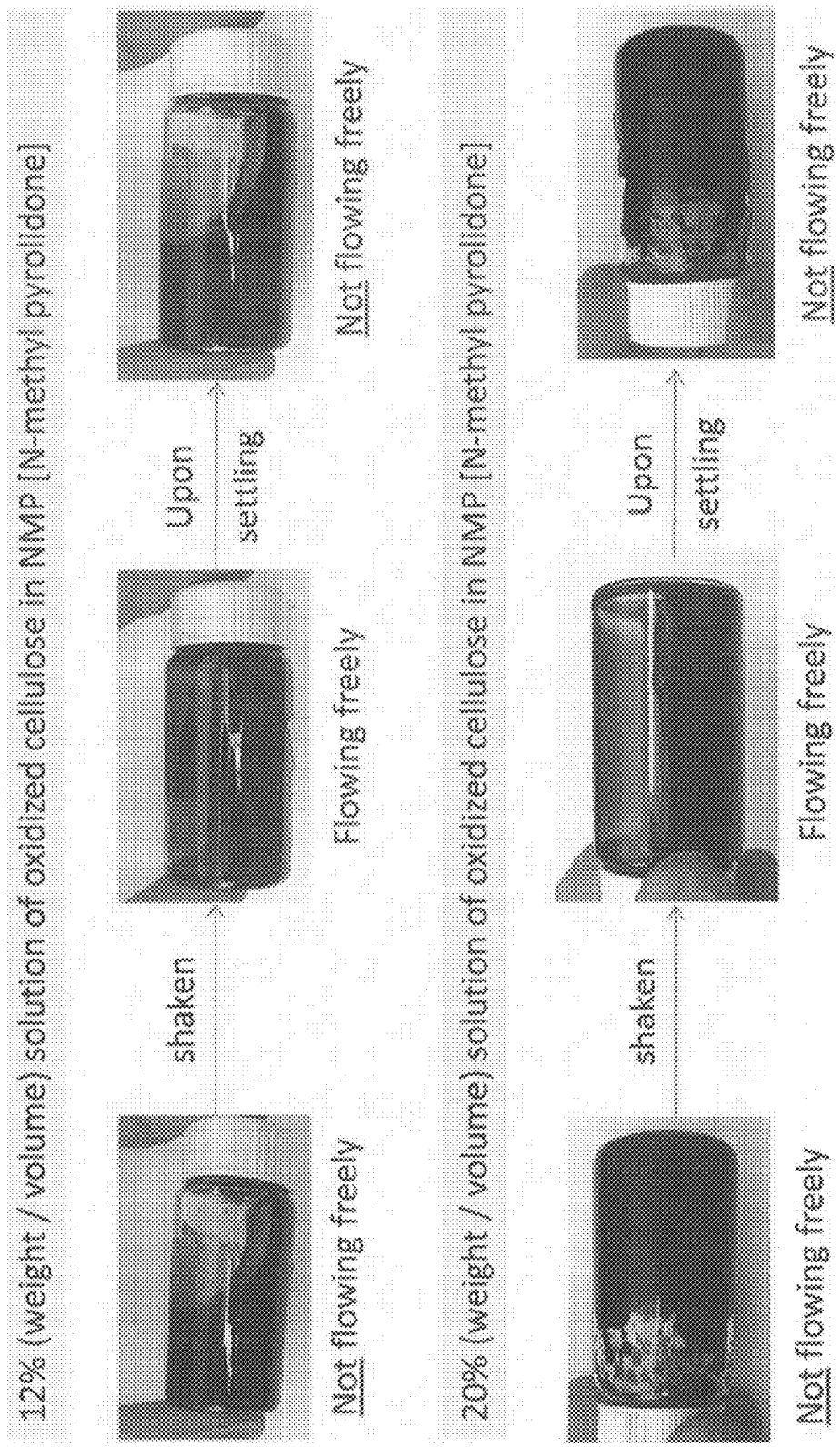
FIG. 39 are photographs of thixotropic oxidized cellulose solutions in accordance with the present disclosure.

Numerous methods may be used to apply shear forces to the present formulations. With reference to FIG. 39, vials containing a thixotropic oxidized cellulose solution may be shaken or otherwise agitated to impart flowability to the solution. Once the agitation is stopped, the oxidized cellulose solution increases in viscosity (as seen in FIG. 39).

In view of these thixotropic properties, oxidized cellulose solutions in accordance with the present disclosure are suitable for use in preparing thixotropic pharmaceutical formulations, in orthopedic applications, in providing a scaffold for tissue engineering, and as a tissue sealant.

a. Pharmaceutical Formulations

Suitable pharmaceutical applications include administration of pharmaceutical formulations formed by contacting thixotropic oxidized cellulose solutions of the present disclosure with one or more bioactive agents disclosed above. Various pharmaceutical formulations may be formed including, but not limited to, parenteral, ophthalmic, vaginal, nasopharyngeal, dental, gastroenterological, and topical formulations.

One or more bioactive agents may be added to the oxidized cellulose solution to form a thixotropic oxidized cellulose pharmaceutical formulation. The solution may be agitated prior to addition of one or more bioactive agents to mix, suspend, and/or dissolve the bioactive agent within the solution. The solution may be agitated from about 0.01 seconds to about 60 seconds for the solution to reach the flowable state, in embodiments from about 1 seconds to about 20 seconds. The solution may have a viscosity in the flowable state from about 0.001 Pascal-second (Pa*s) to about 0.15 Pa*s, in embodiments from about 0.01 Pa*s to about 0.1 Pa*s. The solution may have a viscosity in the gel state from about 0.15 Pa*s to about 1 Pa*s, in embodiments from about 0.2 Pa*s to about 0.75 Pa*s. Once agitated, the solution may equilibrate from the flowable state to the gel state from about 0.01 seconds to about 60 seconds, in embodiments from about 1 seconds to about 20 seconds.

The resulting pharmaceutical formulations may be administered topically, or using any suitable delivery device, such as a syringe, a catheter, an endoscope, or the like. In embodiments, the oxidized cellulose solution may be placed within a delivery device capable of imparting shear forces to the solution. For example, the delivery device may be a mixing syringe, such as disclosed in U.S. Pat. No. 6,706,020, the entire disclosure of which is incorporated by reference herein. The mixing syringe may include a chamber that can be filled with an oxidized cellulose solution in accordance with the present disclosure. In further embodiments, the delivery device may be agitated using an agitation device, such as disclosed in U.S. Pat. No. 6,575,930, the entire disclosure of which is also incorporated by reference herein.

Prior to administration, the present pharmaceutical formulations may be agitated to achieve a desired flowable state, such that the formulation may be administered using the selected delivery device. Insertion of the delivery device to the treatment site may be guided using any suitable imaging technique, such as digital subtraction angiography, fluoroscopy, and the like. Once the delivery device is at the treatment site, the formulation is delivered to the target tissue.

The thixotropic properties of the formulation allow it to form into a gel after delivery to the target tissue, thereby enabling parenteral administration of the formulation. Once in the gel state, the dispersion rate of the bioactive agent from the formulation is at a slower rate than conventional delivery solutions, partially due to the change in viscosity of the formulation according to the present disclosure.

In ophthalmological applications, pharmaceutical formulations according to the present disclosure allow for administration in flowable form, which then produces a viscoelastic gel within the eye. This allows for injection of the formulation in one portion of the eye while the formulation gels in a different part of the eye, allowing for targeted therapy and increasing the duration of release of the bioactive agent.

In gastroenterological applications, the present pharmaceutical formulations may be delivered orally or anally by using any suitable delivery device. The formulations may be delivered to any part of the gastrointestinal tract, e.g., mouth, esophagus, stomach, small and large intestines, colon, anus, etc.

For vaginal delivery, pharmaceutical formulations according to the present disclosure overcome the challenge of limited contact time due to the protective mechanisms of the vagina (e.g., high pH). Thixotropic properties of the formulations according to the present disclosure allow for it to flow into the cervical cavity, and yet remain stationary in the cervix by virtue of gelling after delivery. Additionally, eventual removal of the formulation is facilitated by the reversible behavior of the formulation, e.g., dissolution.

In nasopharyngeal applications, pharmaceutical formulations according to the present disclosure lower the clearance rate and enhance bioavailability of bioactive agents administered through the nasal passage or mouth, e.g., for throat and tonsil therapies. The present pharmaceutical formulations may also be utilized in dental therapies, such as in the treatment of periodontal diseases (e.g., periodontitis and gingivitis). Treatment of such diseases involves application of the formulation in a space between teeth roots and the gums which, due to the thixotropic properties of the formulation, allows it to remain in situ longer.

The pharmaceutical formulations according to the present disclosure may also be used in topical applications, such as ointments, sunscreens, creams, lotions, and the like. Conventional topical applications, which are non-Newtonian fluids and are not thixotropic, fail to form a protective film over the skin. The thixotropic properties of the present formulations allow for uniform distribution of the formulation at the site of administration.

b. Orthopedic Treatments

Thixotropic oxidized cellulose formulations according to present disclosure also may be used in orthopedic applications. In embodiments, the present thixotropic oxidized cellulose formulations may be used as a replacement or supplement for synovial fluid for the purpose of joint lubrication of native and artificial joints.

In embodiments, the formulations and methods of the present disclosure may be used to treat synovial joints in the spine (e.g., facet joints), hip, knee, ankle, finger, toe, elbow, shoulder, wrist, and other joints. These joints may all be treated by injecting the formulation into the joint space to supplement/augment the synovial fluid that lubricates the joint. In embodiments, fluid may be drained from a joint, prior to delivering a thixotropic oxidized cellulose formulation, which may then be delivered to lubricate the joint.

The formulations may be delivered to the joints using guided imaging techniques described above, either as part of stand-alone therapy or during other orthopedic procedures and surgeries. In embodiments, the formulations may include radiocontrast materials to enhance imaging of the injected formulation, and thus, aid in placement of the formulation within the joints. The formulation may be implanted alone or within a matrix, into the joint, where the formulation may be used to produce new cartilage tissue and repair any defect therein.

The formulation according to the present disclosure may be formed in the similar manner as the pharmaceutical formulations as described above. The formulations for use in orthopedic applications may also include any of the suitable bioactive agents described above as well as synovial tissue, synovial cells and/or matrices containing synovial or cambium tissue or cells for use in repairing cartilage and other tissue defects. The formulations for use in orthopedic applications may also include a proliferation agent, transforming factor or other active agents to promote healing.

c. Tissue Engineering

In embodiments, thixotropic oxidized cellulose formulations according to the present disclosure may also be used to provide tissue engineering scaffolds for tissue ingrowth. The formulation may be delivered in the manner described above with respect to pharmaceutical formulations to form a desired pattern and/or shape for the scaffold at a tissue site.

The term "scaffold" as used herein refers to a structure used to enhance or promote the growth of cells and/or the formation of tissue. A scaffold may be a two or three dimensional porous structure that provides a template for cell growth. The scaffold may be infused with, coated with, or otherwise include cells, growth factors, or other bioactive agents to promote cell growth.

The term "tissue site" as used herein refers to a portion of tissue in need of treatment, which may have a wound or defect located on or within any tissue, including, but not limited to, arterial, nerve, and lymph systems, bone tissue, adipose tissue, muscle tissue, neural tissue, dermal tissue, vascular tissue, connective tissue, cartilage, tendons, or ligaments. The term "tissue site" may also refer to portions of any tissue that are not necessarily wounded or defective, but are instead portions in which it is desired to add or promote the growth of additional tissue.

The formulations according to the present disclosure may be percutaneously or parenterally delivered through a delivery device to the tissue site. Initially, the formulation is agitated to reduce the viscosity as described above for pharmaceutical formulations, prior to delivery. This allows for the formulation to fill a void adjacent the tissue site to create a scaffold having a desired shape and/or size while it is flowable.

In embodiments, the formulations for forming a tissue scaffold may be injected into tissue to form one or more traces or lines of the formulation using devices described above with respect to pharmaceutical formulations. A plurality of cross lines may also be formed that intersect previously formed lines or traces, such that a mesh-type scaffold is formed once the formulation becomes more viscous. The formulation may be delivered to the tissue site in a flowable state while retaining its desired material characteristics for a tissue engineering scaffold, namely its thixotropic, hemostatic and swelling properties. However, once the formulation gels, a desired tissue scaffold is formed having a desired shape, pattern, and porosity.

d. Tissue Sealing

Thixotropic oxidized cellulose formulations according to the present disclosure may also be used as a tissue sealant, for example, to treat urinary incontinence or prevent leakage of fluids from other organs. In embodiments, the thixotropic oxidized cellulose sealant may be injected into organs or other tissue having a fistula that needs to be sealed. This approach may also be used in contraception applications to occlude lumens of organs and/or vessels that transport reproductive cells (e.g., ureter or fallopian tubes).

In further embodiments, sealants may also be used to attach tissue implants to tissue. In embodiments, sealants according to the present disclosure may be applied to the target site along with the tissue implants, such as tissue grafts, shunts, slings, meshes, plugs, film, and the like. Tissue implants may include anchor members to aid in placement and securing of the implants at the tissue site. This may assist the sealant attaching the tissue implants at the tissue site.

Tissue implants may be guided and delivered to the tissue site in any suitable manner. A tissue sealant according to the present disclosure may be applied to the tissue site prior to the tissue implant being inserted. In embodiments, the tissue sealant may be applied to the tissue implant prior to attachment of the implant to the tissue site. In further embodiments, the tissue sealant may be applied to the tissue implant after the implant has been placed at the tissue site.

It should be appreciated that the above-described embodiments of the oxidized cellulose multi-encapsulated microspheres, embolization compositions, and formulations, are merely illustrative and various additional combinations of microspheres, solutions, formulations, bioactive agents, visualization agents, cross-linking precursors, magnetic materials, radioactive materials, radio-protective materials and the like may be used in combination and/or interchangeably therewith.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C.

EXAMPLES

Comparative Example 1

This Example describes incomplete dissolution of oxidized cellulose having a degree of oxidation of 0.6 in a solution including 8% by weight lithium chloride (LiCl) and N-methyl-2-N,N-Dimethylacetamide (DMAc).

About 1.6 grams (g) of LiCl was first dissolved in about 20 milliliters (mL) DMAc to form an 8% LiCl in DMAc solution. About 20 milliliters (mL) of the 8% LiCl in DMAc solution was added to a reactor vessel, and was heated to about 160° C. under argon. About 149 milligrams (mg) of oxidized cellulose having a degree of oxidation of 0.6 was added to the reactor vessel. The mixture was heated for about 1.17 hours, cooled to ambient temperature, and discharged from the reactor vessel. The sample did not fully dissolve, and was observed to discolor significantly, indicating that further oxidation of the oxidized cellulose had occurred.

Comparative Example 2

This Example describes incomplete dissolution of oxidized cellulose having a degree of oxidation of 0.6 in 8% by weight of LiCl in DMAc solution.

About 20 mL of the 8% LiCl in DMAc solution produced above in Comparative Example 1 and about 90 mg of oxidized cellulose having a degree of oxidation of 0.6 were added to a reactor vessel. The mixture was heated to about 150° C. under argon for about 5.3 hours, cooled to ambient temperature, and discharged from the reactor vessel. The sample did not fully dissolve, and was observed to discolor significantly, indicating further oxidation of the oxidized cellulose occurred.

Comparative Example 3

This Example describes pretreatment of oxidized cellulose having a degree of oxidation of 0.6 in water.

About 22 mg of oxidized cellulose having a degree of oxidation of 0.6 was placed in a reactor vessel and about 0.66 grams of deionized water was added thereto. The mixture was stirred for a period of time from about 2 minutes to about 3 minutes. The water was then removed in a vacuum, and about 20 mL of the 8% LiCl in DMAc solution from Comparative Example 1 was added to a reactor vessel. The mixture was heated to about 155° C. for about 4.6 hours. It was then cooled to ambient temperature, and discharged from the reactor vessel. The sample did not fully dissolve. Thus, pretreatment of the oxidized cellulose in water had no discernable effect on dissolution.

Comparative Example 4

This Example describes dissolution of cellulose in a solution including 1% by weight of LiCl in N-methyl-2-pyrrolidinone (NMP) under inert atmosphere.

About 20 mL of the NMP and approximately 80 mg of non-modified cellulose were added to a reactor vessel. The mixture was heated to about 150° C. under argon for about 6 hours and then cooled to about 110° C. after which approximately 0.2 g of LiCl was added to the reactor vessel. The reactor vessel was maintained at about 110° C. for an additional hour before being cooled to about 80° C. The reactor vessel was maintained at about 80° C. for about 14.5 hours after which it was observed that the sample had not dissolved and that pieces of non-modified cellulose were observed in the reactor vessel indicating that 1% LiCl NMP solution did not completely dissolve cellulose.

Example 1

This Example describes dissolution of oxidized cellulose having a degree of oxidation of 0.6 in a solution including 1% by weight of LiCl in N-methyl-2-pyrrolidinone (NMP).

A 100 mL three-neck round-bottom flask was used as a reactor vessel and was fitted with a gas inlet, a mechanical stirrer, and a gas outlet, which was then connected to a flow rate monitor. The flask was purged with argon for about 5 minutes at a rate of approximately 0.4 liter per minute (L/min), which was measured as approximately 5 bubbles per second by the flow rate monitor.

About 20 mL of anhydrous NMP was pipetted into the flask, which was then again purged with argon. Argon flow was adjusted to a rate of approximately 0.2 L/min or from about 2 bubbles per second to about 3 bubbles per second, as observed on the flow rate monitor.

A helium line was attached to the flask and the argon flow was stopped. The helium line was inserted into the reactor and submerged below the liquid level, and the helium flow was set at approximately 0.2 L/min to sparge the NMP. After about 45 minutes of sparging, the helium line was removed and the argon flow was reinitiated at a rate of about 0.2 L/min.

About 80 mg of oxidized cellulose having a degree of oxidation of 0.6 was cut into approximately 0.5 cm×0.5 cm square pieces. Argon flow was temporarily increased to about 0.4 L/min and the oxidized cellulose was added to the flask, after which the argon flow was restored to about 0.2 L/min.

The mixture was stirred at about 200 revolutions per minute (rpm). The flask was heated from about 130° C. to about 135° C. using a temperature-controlled heating mantle. The temperature was maintained for about 2 hours under argon as the mixture was stirred. Thereafter, the mixture was cooled to a temperature from about 100° C. to about 110° C.

A scintillation vial was purged with argon in preparation for addition of LiCl. About 0.2 grams of anhydrous LiCl was weighed in the vial. Stirring was temporarily suspended and argon flow was increased to about 0.4 L/min while the LiCl was added to the reactor vessel. After addition of the LiCl, the argon flow was restored to about 0.2 L/min. Stirring was resumed at about 450 rpm for about 5 minutes and then reduced to about 200 rpm.

Temperature was maintained from about 100° C. to about 110° C. The mixture was visually inspected approximately 5 minutes after addition of the LiCl and about every 15 minutes thereafter to determine whether oxidized cellulose was dissolved. The oxidized cellulose was observed to have undergone complete dissolution. Heating was terminated and the solution was cooled to ambient temperature and stirred at about 200 rpm. The solution was then transferred into a scintillation vial under argon and sealed. The solution was stored at ambient conditions.

Example 2

This Example describes dissolution of oxidized cellulose having a degree of oxidation of 0.6 in a solution including 1% by weight of LiCl in NMP under ambient atmosphere.

The same process was followed as set forth in Example 1 above, except the dissolution was carried out under ambient atmosphere. Oxidized cellulose was observed to have undergone complete dissolution.

Example 3

This Example describes dissolution of oxidized cellulose having a degree of oxidation of 0.6 in a solution including 1% by weight of LiCl in NMP under ambient atmosphere without helium sparging.

The same process was followed as set forth in Example 1 above, except the dissolution was carried out under ambient atmosphere and without helium sparging. Oxidized cellulose was observed to have undergone complete dissolution.

Molecular weight was determined for the dissolved oxidized cellulose of Examples 1-3 as summarized in Table 1 below.

Table 1

TABLE 1

| Example | Mn (g/mol) |
|---------|------------|
| 1 | $2.7 \times 10^5$ |
| 2 | $1.4 \times 10^5$ |
| 3 | $1.8 \times 10^5$ |

As illustrated in Table 1, dissolved oxidized cellulose of Example 1 had the highest molecular weight, whereas the dissolved oxidized cellulose of Examples 2 and 3 had a much lower molecular weight. Without being bound by any particular theory, it is believed that conducting dissolution under ambient atmosphere degrades the oxidized cellulose, resulting in lower molecular weight.

Example 4

This Example describes the dissolution of non-modified cellulose in 8% by weight on LiCl in NMP solution and analysis of the dissolved oxidized cellulose of Example 1, the non-modified cellulose of this Example, and a pullalan standard sample using gel permeation chromatography (GPC).

The same process was followed as set forth in Example 1 above, except about 80 mg of non-modified cellulose was dissolved, the mixture of the non-modified cellulose and the solvent was heated from about 145° C. to about 155° C., and about 1.6 grams of anhydrous LiCl was added to the mixture to achieve 8% by weight LiCl in NMP solution since 1% LiCl solution was ineffective as illustrated in Comparative Example 4. Further, after addition of LiCl, the temperature was maintained from about 100° C. to about 110° C. for at least one hour. The non-modified cellulose was observed to have undergone complete dissolution.

Samples of the dissolved oxidized cellulose of Example 1, the non-modified cellulose of this Example, and the pullalan standard sample were then analyzed using GPC. A mobile phase of 1% by weight of LiCl in NMP Solution for GPC was prepared. About 1.5 liters (L) of NMP was added to a 2 L volumetric flask, which was then loosely capped with a glass stopper. NMP was stirred. About 20 grams of LiCl was added to the NMP and was stirred for about 60 minutes until it was dissolved. About 0.5 L of NMP was added to the 2 liter mark and stirring was stopped. Additional NMP was added to the mark and the solution was mixed by hand-inverting. A 1 micron polytetrafluoroethylene (PTFE) filter membrane was placed in a filtration apparatus and a vacuum was applied, which enabled the LiCl in NMP solution to flow through the membrane, thereby filtering the solution. The mobile phase solution was stored at ambient conditions.

Samples of the dissolved oxidized cellulose of Example 1, the non-modified cellulose of Example 4, and a pullalan standard sample were separately filtered through a 1 micron PTFE filter membrane into 3 separate high-performance liquid chromatography (HPLC) vials. In addition, a combined sample was also prepared by combining about 500 microliters (µL) of the dissolved oxidized cellulose of Example 1 and about 500 µL of the pullalan standard sample (at a concentration of about 2 mg/mL) in a single HPLC vial.

All of the samples were subjected to GPC analysis performed using a gel permeation chromatography system with two 300 millimeter (mm)×7.5 mm columns of Polymer Laboratories' PLGEL™ in a series configuration. A DAWN® HELEOS™ II multi-angle laser light scattering system from (Wyatt Technology of Santa Barbara, Calif.) was used for absolute molecular weight determination. A refractive index model number OPTI LAB® rEX in conjunction with the light scattering detector supplied by Wyatt Technology was also used during molecular weight analysis.

Figure 18:
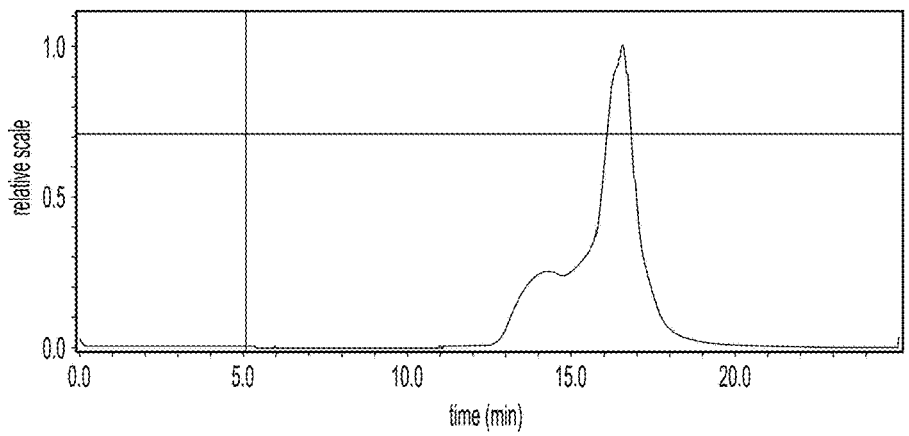
FIG. 18 is a graph of a chromatogram of oxidized cellulose dissolved in accordance with the present disclosure.
Figure 19:
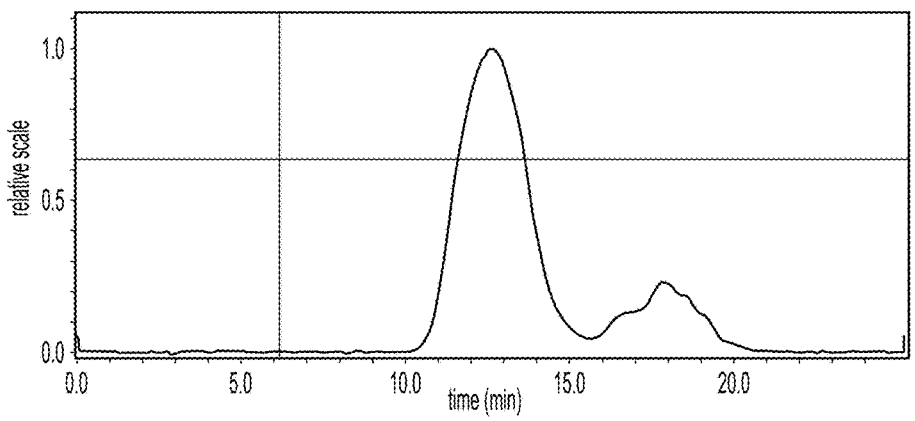
FIG. 19 is a graph of a chromatogram of non-modified cellulose dissolved in accordance with the present disclosure.

GPC was performed at a flow rate of about 1 mL per minute, at a temperature of about 50° C., with an injection volume of about 100 µL. GPC chromatograms of the oxidized cellulose of Example 1 and the non-modified cellulose of Example 4 are shown in FIGS. 18 and 19, respectively.

Example 5

This Example describes dissolution of oxidized cellulose having a degree of oxidation of 0.39 in 8% by weight of LiCl in DMAc solution.

About 20 mL of DMAc was added to a reactor vessel under argon, followed by sparging thereof for approximately 10 minutes with helium. About 19 mg of oxidized cellulose having a degree of oxidation of 0.39 was added to the reactor vessel, which was initially heated to about 144° C. After addition of the oxidized cellulose, the temperature was increased to about 152° C. for approximately 3.2 hours. The reactor vessel was then cooled to about 95° C. and about 1.6 grams of LiCl was added to the mixture to form an 8% LiCl in DMAc solution. The mixture was then heated to about 95° C. for about 45 minutes, then cooled to ambient temperature. The solution was stirred at ambient temperature for approximately 64 hours, and discharged from the reactor vessel. The oxidized cellulose was observed to have undergone complete dissolution.

Example 6

This Example describes dissolution of oxidized cellulose having a degree of oxidation of 0.39 in a solution including 8.8% by weight of LiCl in NMP.

About 20 mL of NMP was added to the reactor vessel under argon followed by sparging thereof for approximately 1 hour with helium. About 10.2 mg of oxidized cellulose having a degree of oxidation of about 0.39 was added to the reactor vessel, which was initially heated to a temperature from about 148° C. to about 154° C. for approximately 2.5 hours. The reactor vessel was then cooled to about 103° C. and about 1.77 grams of LiCl was added to the mixture to form an 8.8% LiCl in NMP solution. The mixture was then heated to a temperature from about 103° C. to about 105° C. for about 1 hour, then cooled to ambient temperature. The solution was stirred at ambient temperature for approximately 24 hours, and discharged from the reactor vessel. The oxidized cellulose was observed to have undergone complete dissolution.

Example 7

This Example describes dissolution of oxidized cellulose having a degree of oxidation of 0.39 in a solution including 1% by weight of LiCl in NMP.

About 20 mL of NMP was added to the reactor vessel under argon followed by sparging thereof for approximately 1 hour with helium. About 11 mg of oxidized cellulose having a degree of oxidation of about 0.39 was added to the reactor vessel, which was initially heated to a temperature from about 143° C. to about 148° C. for approximately 2 hours. The reactor vessel was then cooled to about 100° C. and about 0.20 grams of LiCl was added to the mixture to form a 1% LiCl in NMP solution. The mixture was then heated to about 93° C. for about 8 minutes, then cooled to ambient temperature. The solution was stirred at ambient temperature for approximately 24 hours, and discharged from the reactor vessel. The oxidized cellulose was observed to have undergone complete dissolution.

Example 8

This Example describes formation of oxidized cellulose microspheres from an oxidized cellulose solution including 1% by weight of LiCl in N-methyl-2-pyrrolidinone (NMP).

A 600 mL glass beaker was set on a ring stand. A constant-torque mixer was fitted with a medium-shear impeller, which was inserted into the beaker. Approximately 200 mL of heavy white mineral oil was added to the beaker with the mixer set to rotate at approximately 1,500 rpm. About 1.7 grams of oxidized cellulose solution (about 15% by weight/volume of oxidized cellulose in NMP) was added drop-wise to the vortex of the stirring mineral oil for about 15 minutes until all of the solution was added to the oil to form an emulsion including a plurality of oxidized cellulose microspheres.

About 150 mL of isopropyl myristate was added to the emulsion and the mixer speed reduced to approximately 900 rpm and maintained for about about 45 minutes. Thereafter, another 150 mL of isopropyl myristate was added to the emulsion such that isopropyl myristate was present at a ratio to the oil of about 3:2 and rotations were reduced to approximately 600 rpm.

Figure 20A:
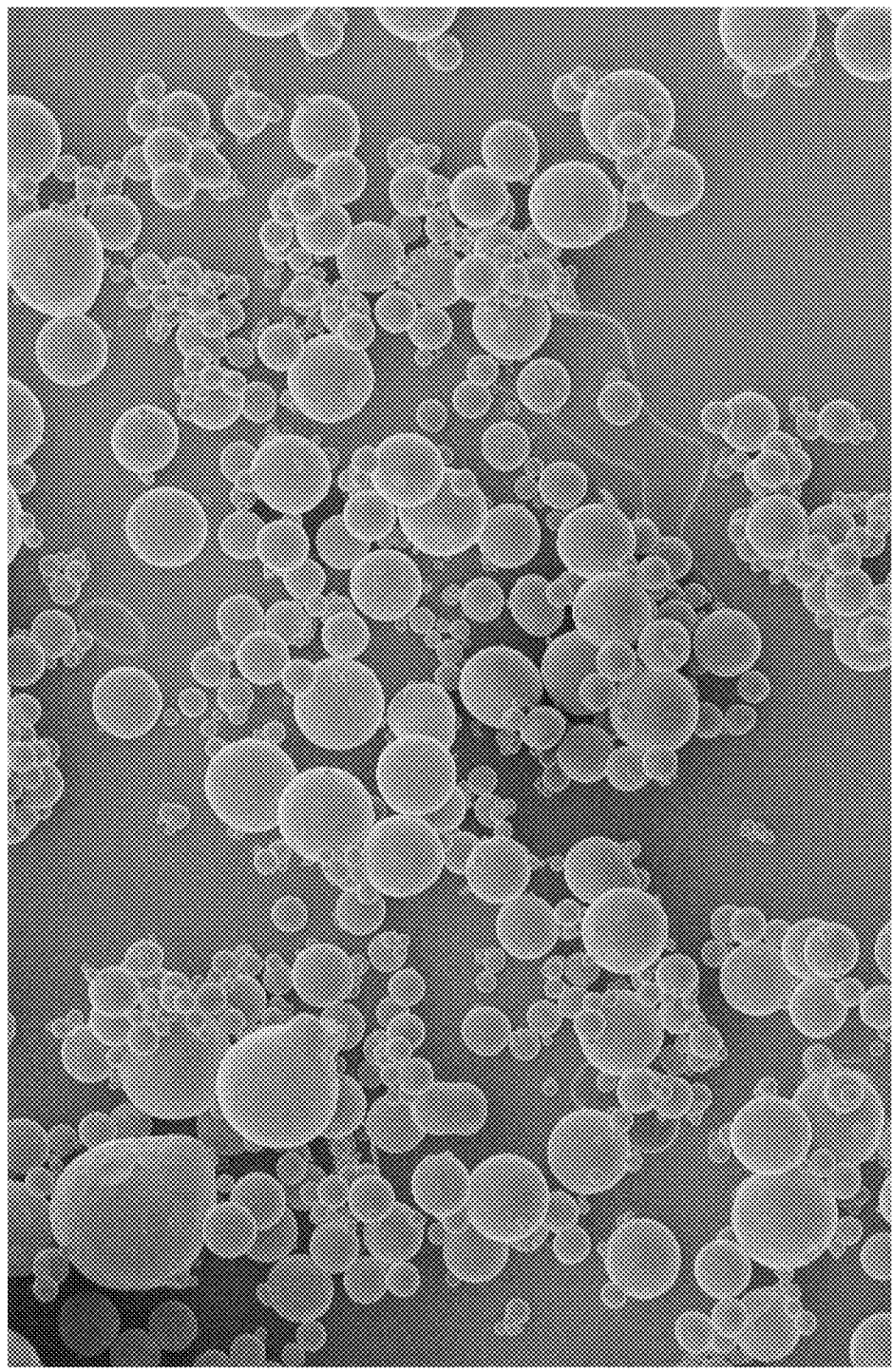
FIGS. 20A-B are scanning electron microscope images of oxidized cellulose microspheres in accordance with the present disclosure.
Figure 20B:
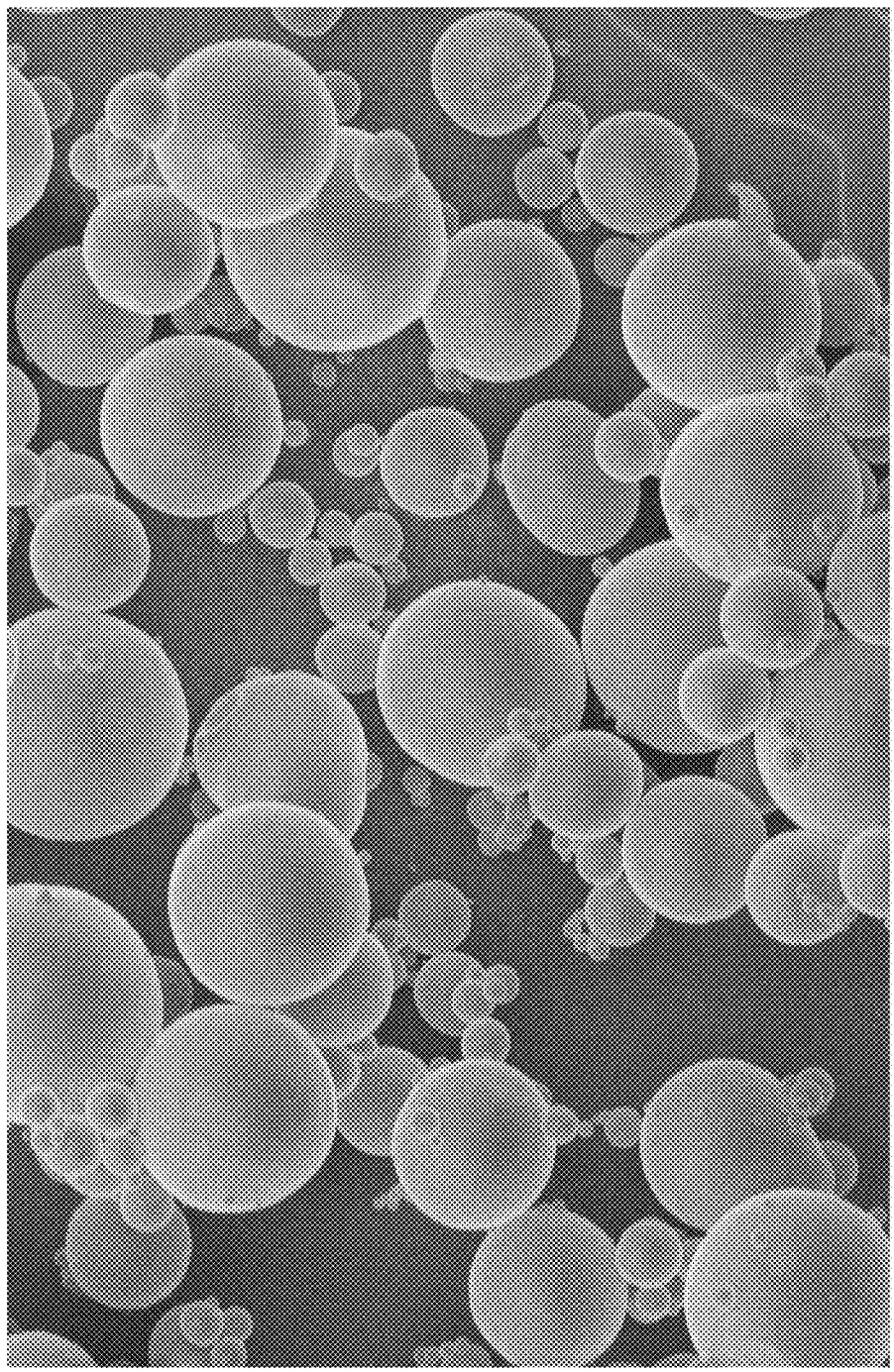

The emulsion was stirred from about 2 hours to about 3 hours to extract the NMP from the oxidized cellulose microspheres. After NMP was extracted, microspheres were collected by filtration. The microspheres were then washed with a sufficient volume of n-heptane to remove any trace of processing oils on the surface of the microspheres. The microspheres were dried for about 24 hours. Collected microspheres shown in FIGS. 20A-B were imaged using a Zeiss Leo 435, scanning electron microscope (SEM) at about 100× and 250×, respectively. The SEM images show microspheres having a spherical shape and a smooth outer surface.

Example 9

This Example describes formation of 18% by weight (theoretical loading) vitamin B-12 loaded oxidized cellulose microparticles, from a 15% by weight/volume oxidized cellulose solution including 1% by weight of LiCl in N-methyl-2-pyrrolidinone (NMP).

A discontinuous phase was prepared from the oxidized cellulose solution of Example 1. About 3 grams of the oxidized cellulose solution (about 15% by weight/volume of oxidized cellulose in NMP) was combined with approximately 100 milligrams of cyanocobalmin (vitamin B-12).

A 1 liter glass beaker was set on a ring stand. A constant-torque mixer was fitted with a medium-shear impeller, which was inserted into the beaker. Approximately 300 mL of heavy white mineral oil was added to the beaker with the mixer set to rotate at approximately 550 rpm. The solution of cyanocobalmin and oxidized cellulose was then added drop-wise to the vortex of the stirring mineral oil for about 15 minutes until all of the solution was added to the oil to form an emulsion.

About 300 mL of cottonseed oil was added to the emulsion. The emulsion was stirred at approximately 900 rpm for about 60 minutes. Thereafter, another 300 mL of cottonseed oil was added to the emulsion. The emulsion was again stirred at approximately 900 rpm for about 60 minutes. About 100 mL of n-heptane was added to the emulsion.

The emulsion was stirred for about 60 minutes to extract the NMP from the oxidized cellulose microparticles. After NMP was extracted, microparticles were collected by filtration. The microparticles were then washed with a sufficient volume of n-heptane to remove any trace of processing oils on the surface of the microparticles. The microparticles were dried for about 24 hours.

Figure 21A:
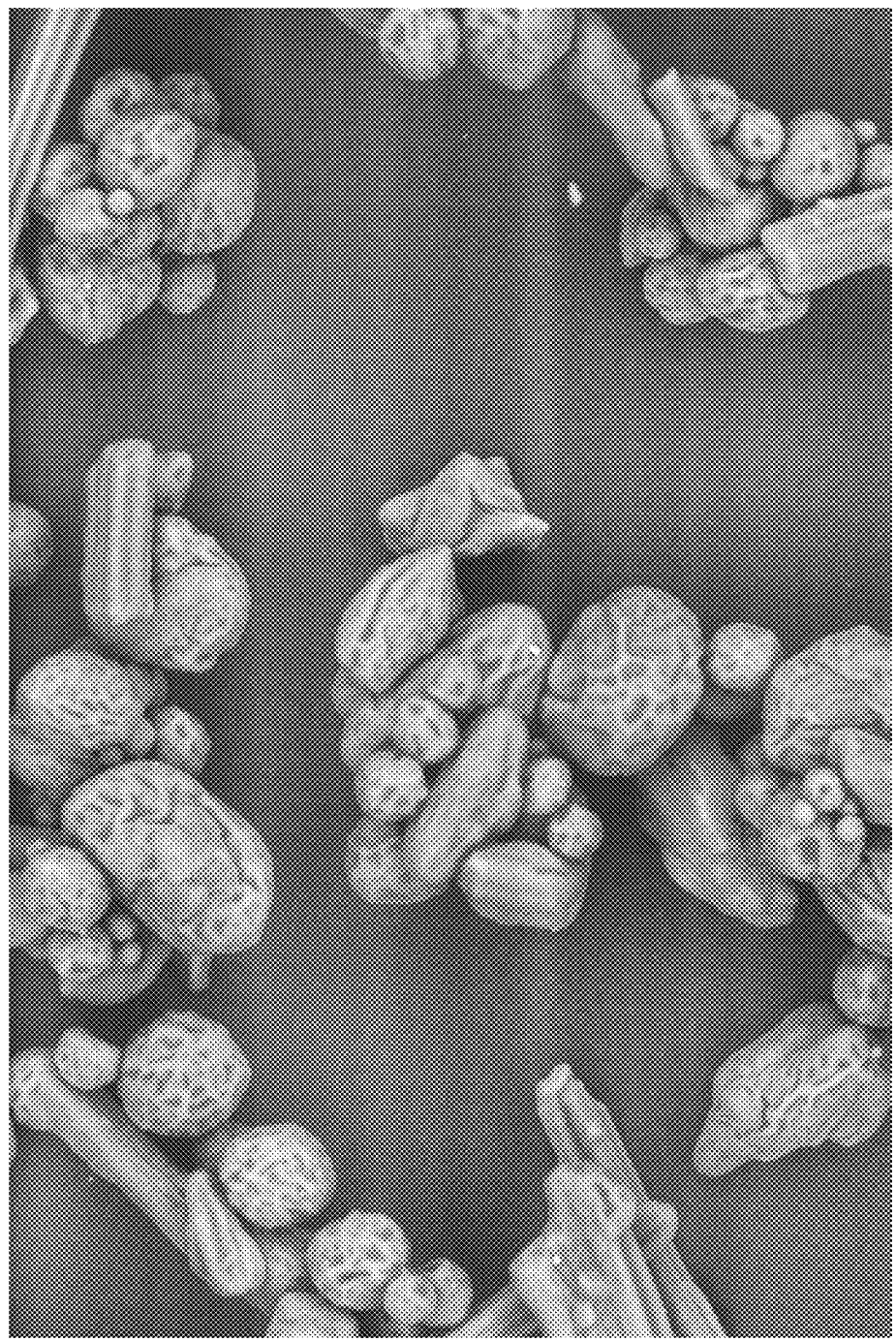
FIGS. 21A-B are scanning electron microscope image of oxidized cellulose microparticles including 18% loaded vitamin B-12 in accordance with the present disclosure.
Figure 21B:
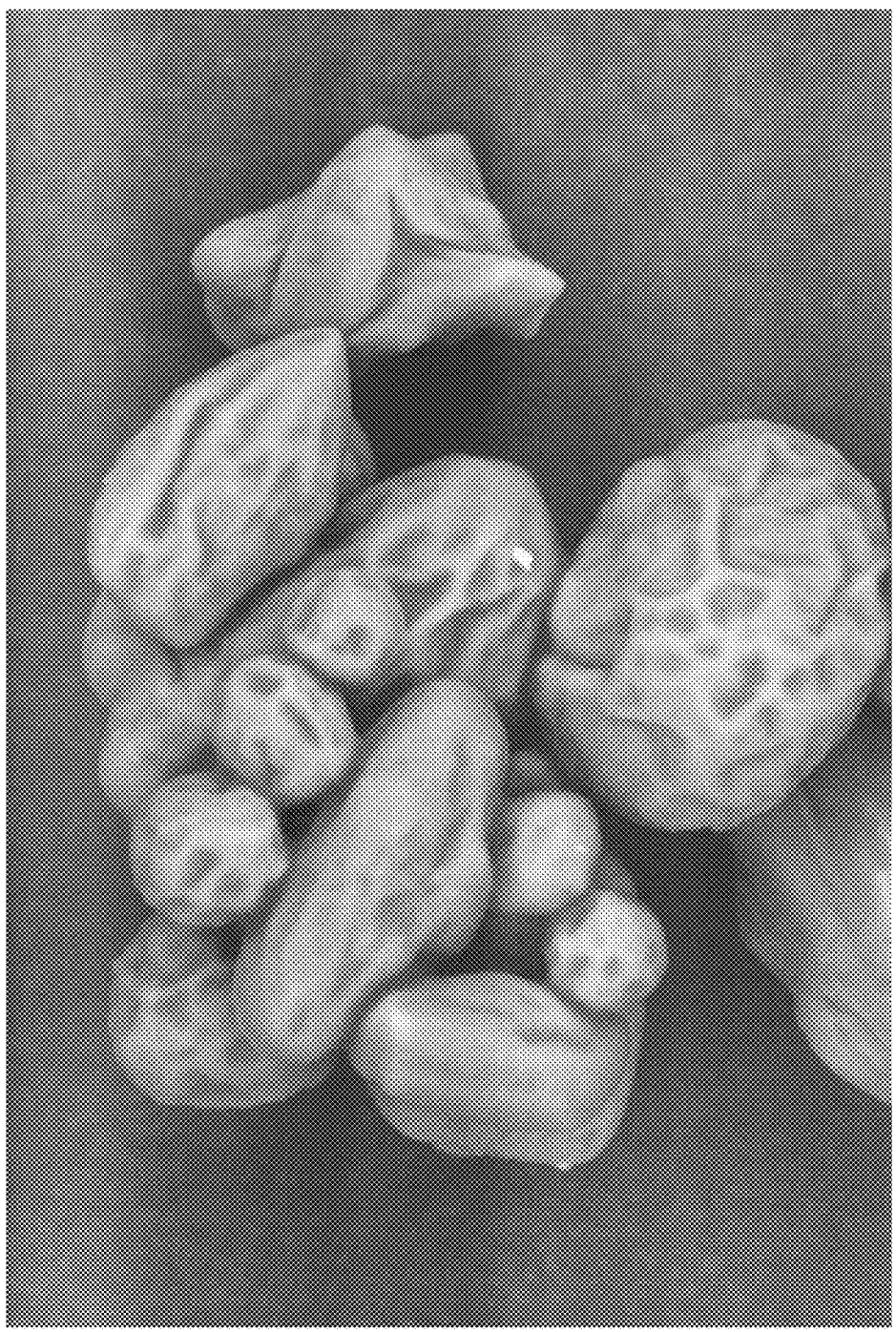

Collected microparticles were imaged using a Zeiss Leo 435 SEM, which are shown in FIGS. 21A-B at about 500×, and 1100×, respectively. The SEM images show microparticles having a textured surface with some microparticles having an elongated, rod-like shape and others having a sphere-like shape. Without being bound by any particular theory, it is believed that smooth, spherecal structure of the microparticles is caused by hydrophilic nature of B-12.

Example 10

This Example describes formation of 40% by weight (theoretical loading) bupivacaine free base loaded oxidized cellulose microparticles, from a 15% by weight/volume oxidized cellulose solution including 1% by weight of LiCl in N-methyl-2-pyrrolidinone (NMP).

The same process was followed as set forth in Example 9 above, except about 253.5 milligrams of bupivacaine free base was added to the oxidized cellulose solution.

Figure 22A:
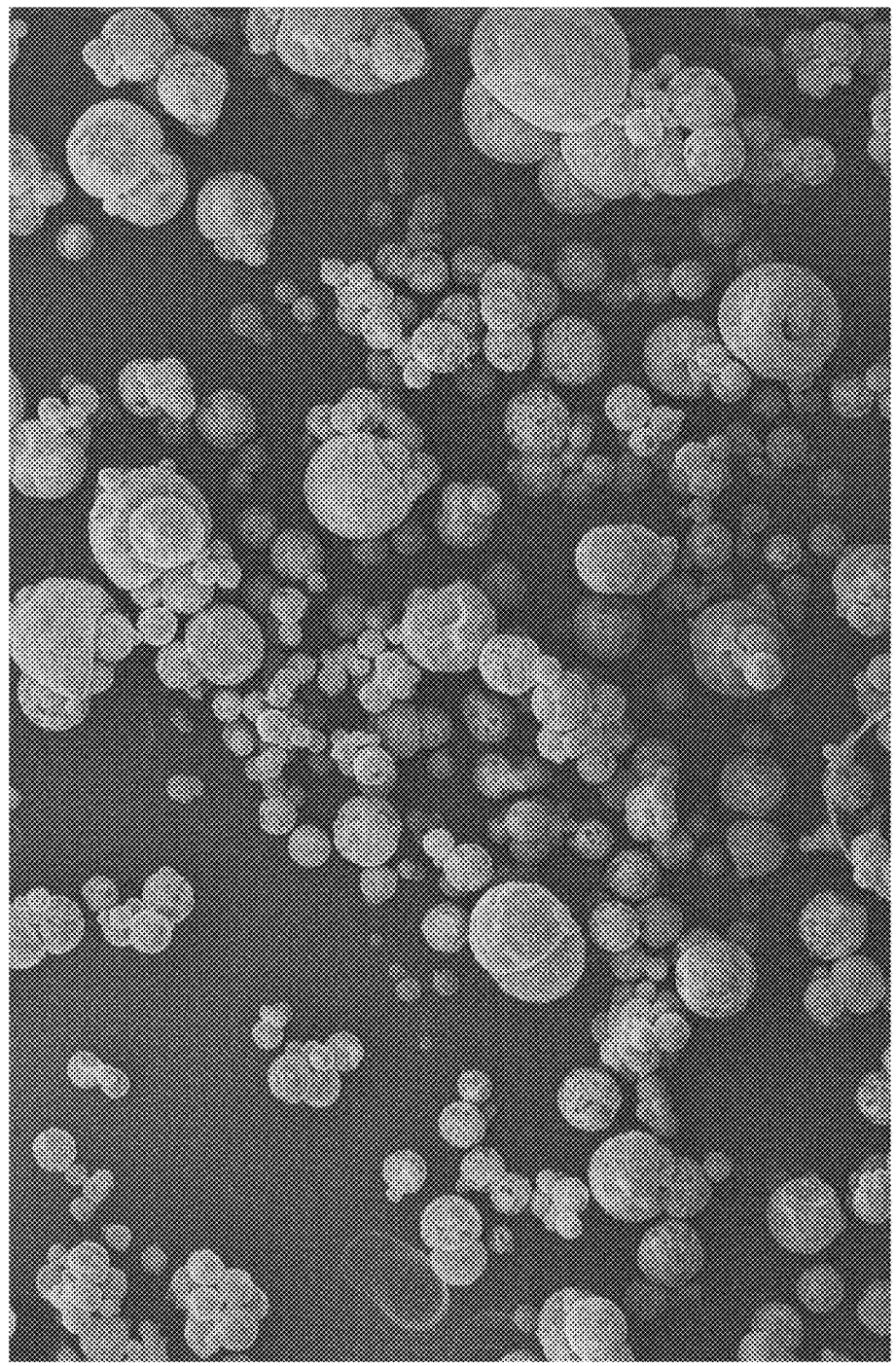
FIGS. 22A-B are scanning electron microscope images of oxidized cellulose microparticles including bupivacaine free base in accordance with the present disclosure.
Figure 22B:
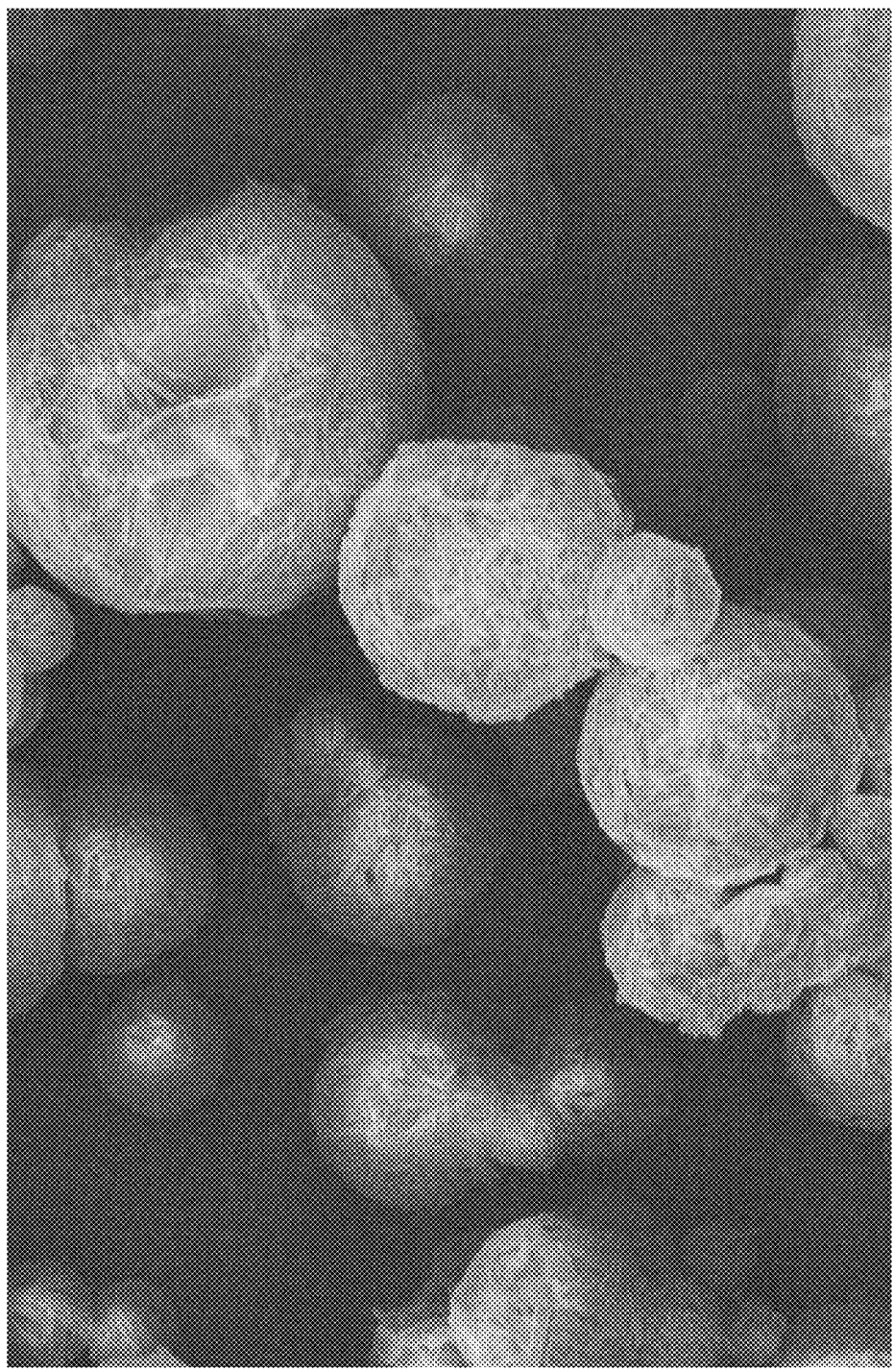

Collected microparticles were imaged using a Zeiss Leo 435 SEM, which are shown in FIGS. 22A-B at about 50× and 250×, respectively. The SEM images show microparticles having a spherical shape and a textured surface. Without being bound by any particular theory, it is believed that the rougher surface is caused by the wrapping of the crystals of bupivacaine free base, which is hydrophobic, within the oxidized cellulose microparticles.

Example 11

This Example describes formation of 40% by weight (theoretical loading) bupivacaine HCl loaded oxidized cellulose microparticles, from a 15% by weight/volume oxidized cellulose solution including 1% by weight of LiCl in N-methyl-2-pyrrolidinone (NMP).

The same process was followed as set forth in Example 9 above, except about 250.2 milligrams of bupivacaine HCl was added to the oxidized cellulose solution.

Figure 23A:
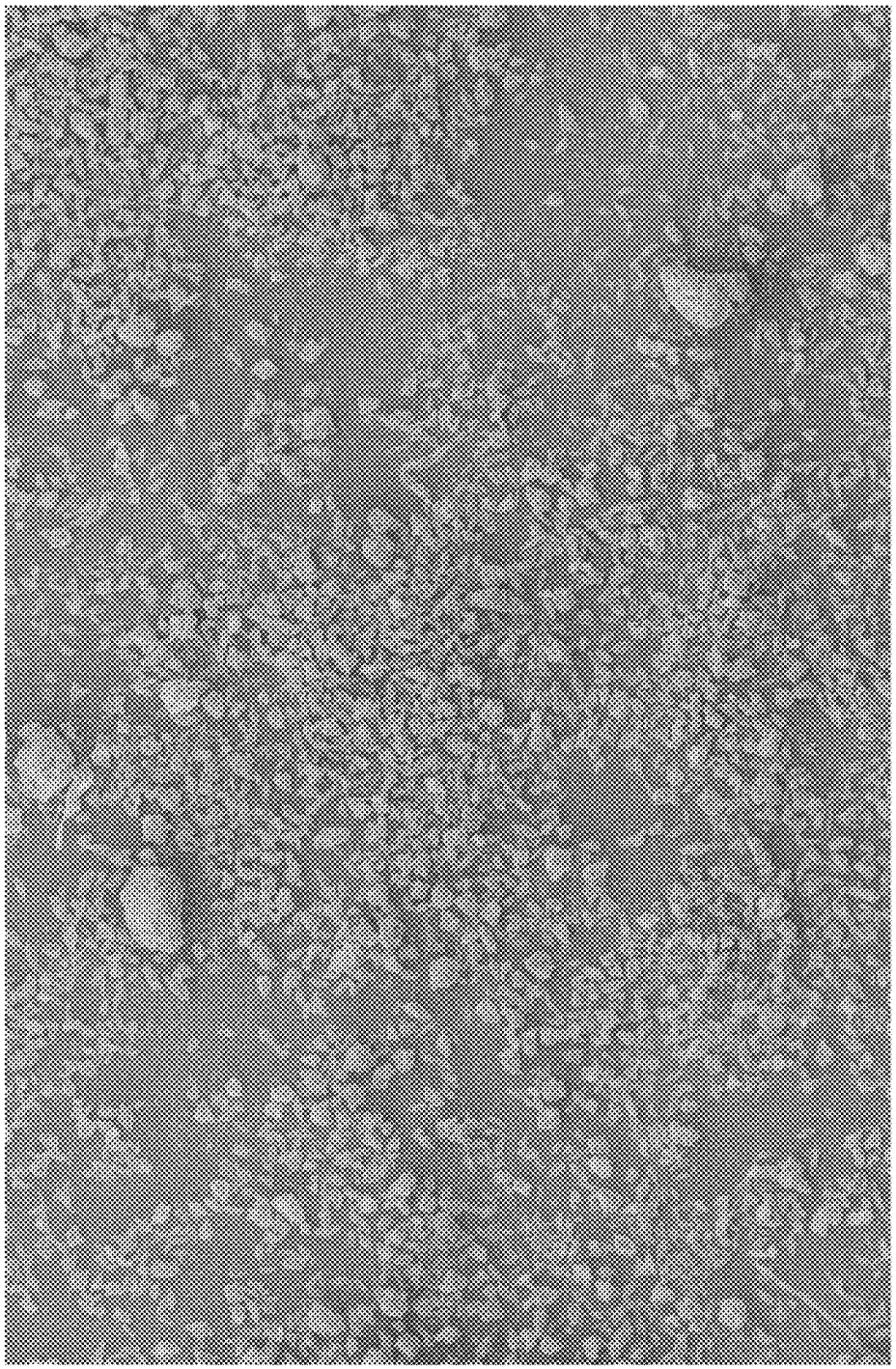
FIGS. 23A-B are scanning electron microscope images of oxidized cellulose microspheres including bupivacaine hydrochloride form in accordance with the present disclosure.
Figure 23B:
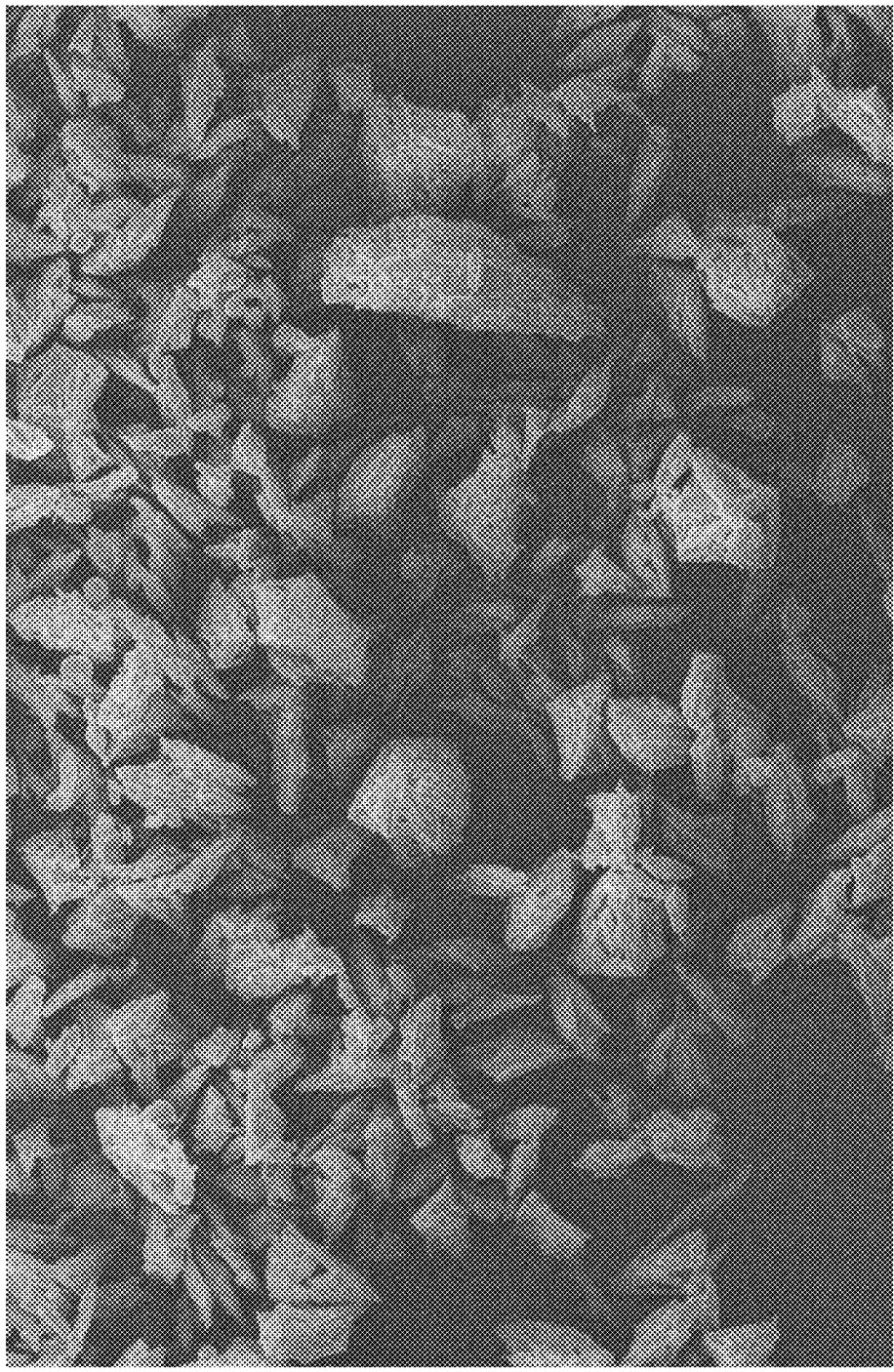

Collected microparticles were imaged using a Zeiss Leo 435 SEM, which are shown in FIGS. 23A-B at about 50× and 250×, respectively. The SEM images show microsparticles having an irregular, crystalline shape and a textured surface. Without being bound by any particular theory, it is believed that structure of the microparticles is caused by the needle-like crystalline nature of bupivacaine HCl, which hydrophilic.

Example 12

This Example describes formation of 30% (theoretical and actual measurement) by weight vitamin B-12 loaded oxidized cellulose microspheres, from a 15% by weight/volume oxidized cellulose solution including 1% by weight of LiCl in N-methyl-2-pyrrolidinone (NMP).

The same process was followed as set forth in Example 9 above, except about 200 milligrams of cyanocobalmin (vitamin B-12) was added to the oxidized cellulose solution.

Figure 25A:
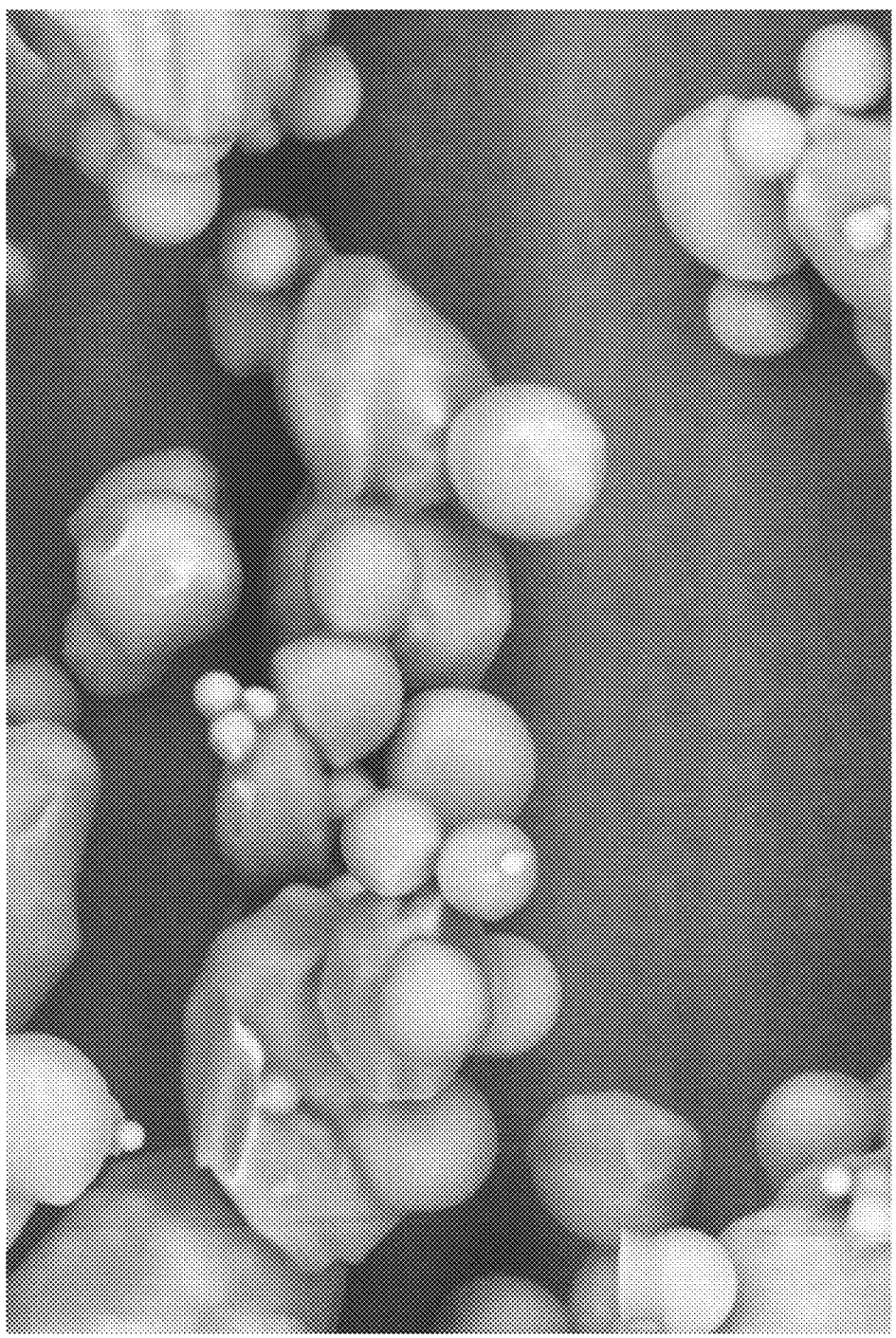
FIGS. 25A-B are scanning electron microscope images of oxidized cellulose microparticles including 30% loaded vitamin B-12 in accordance with the present disclosure.
Figure 25B:
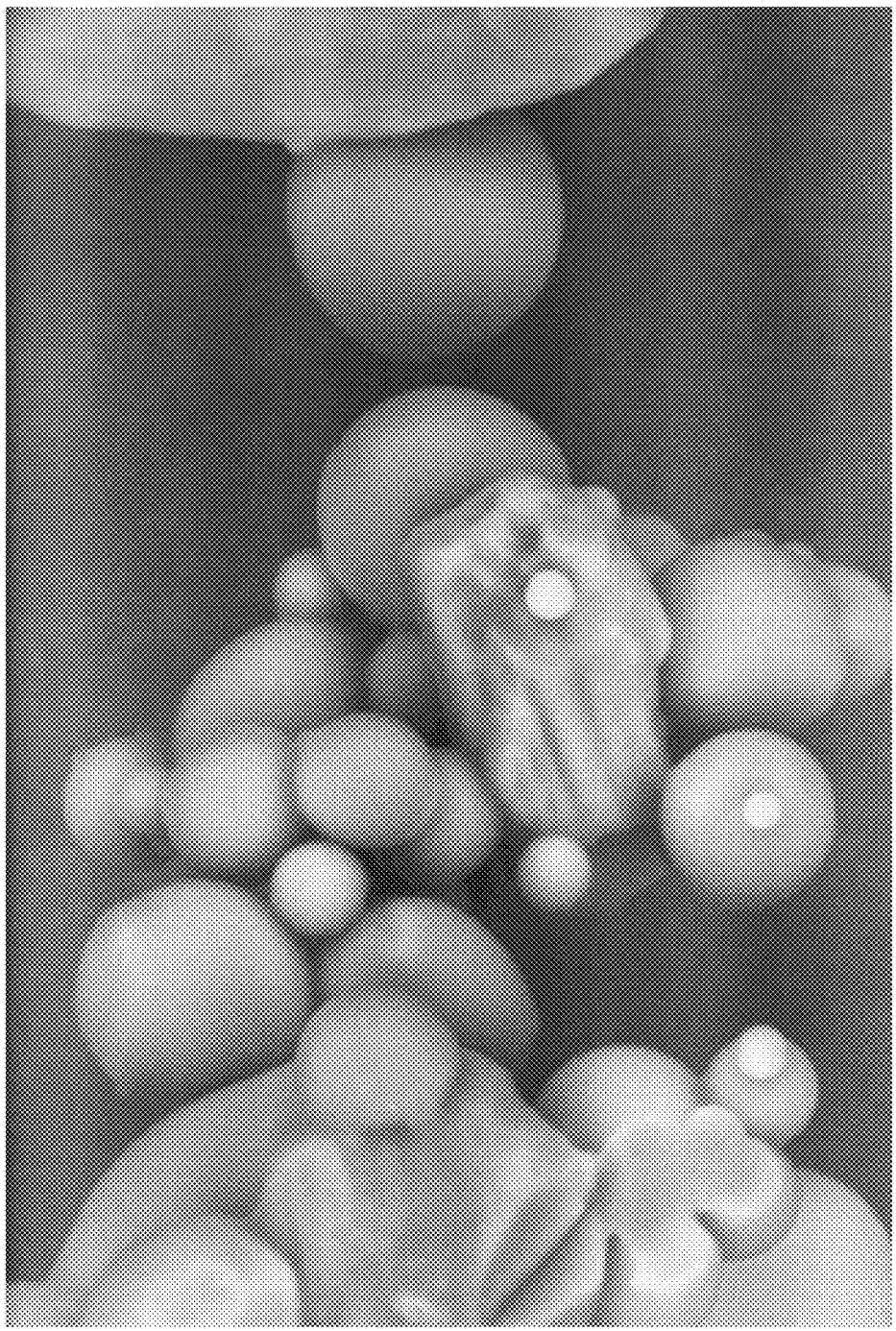

Collected microparticles were imaged using a Zeiss Leo 435 SEM, which are shown in FIGS. 25A-B at about 1,000× and 1,700×, respectively. The SEM images show microspheres having a substantially spherical shape and a smooth outer surface.

Figure 24:
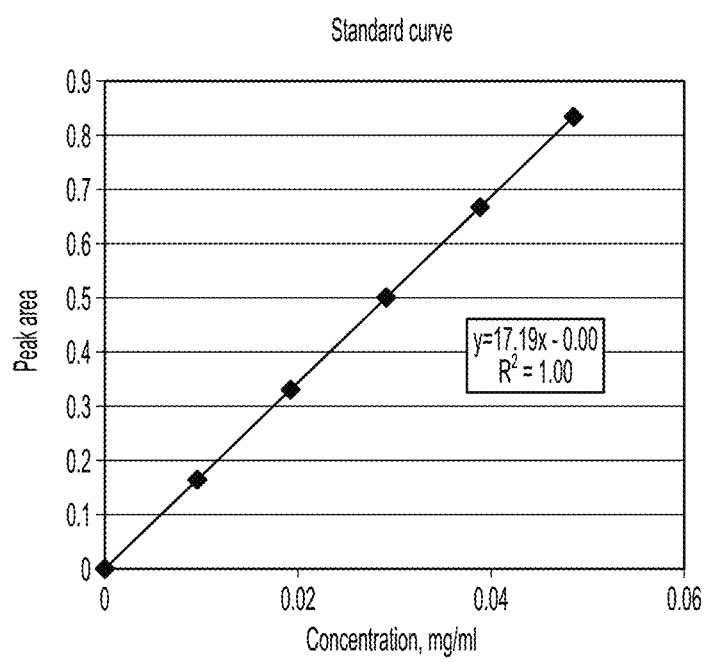
FIG. 24 is an ultraviolet-visible spectroscopy standard calibration curve for vitamin B-12.

Actual loading of the 30% B-12 loaded microspheres was determined using a SpectraMax M2, a UV-Vis spectrophotometer. Approximately 1 mg of B-12 was dissolved in about 10 mL of water and scanned from about 200 nm to about 800 nm in order to determine maximum absorbance. Maximum absorbance was measured at approximately 358 nm. A stock solution was made with about 10 mg B-12 in 200 mL of water. From this stock solution, serial dilutions were made and a five (5) point standard calibration curve was constructed as shown in FIG. 24. About 2.55 mg of the 30% B-12 loaded microspheres was dissolved in 10 mL water, then further diluted to achieve a ratio of microspheres to water of about 1:2. The diluted solution was analyzed and measured at an absorbance concentration of approximately 0.679 as shown in Table 2 below. Actual loading of vitamin B-12 was measured to be about 31%.

TABLE 2

| | Absorbance | Conc, mg/mL | Total amt., mg | % API | Sample Weights, mg |
|---|---|---|---|---|---|
| Vitamin B12 oxidized cellulose microspheres | 0.679 | 0.04 | 0.79 | 31.0 | 2.55 |

Example 13

This Example describes formation of 25% by weight (theoretical loading) vitamin B-12 loaded oxidized cellulose microspheres from a 15% by weight/volume oxidized cellulose solution including 1% by weight of LiCl in N-methyl-2-pyrrolidinone (NMP).

The same process was followed as set forth in Example 9 above, except about 150 milligrams of vitamin B-12 was added to the oxidized cellulose solution.

Figure 26A:
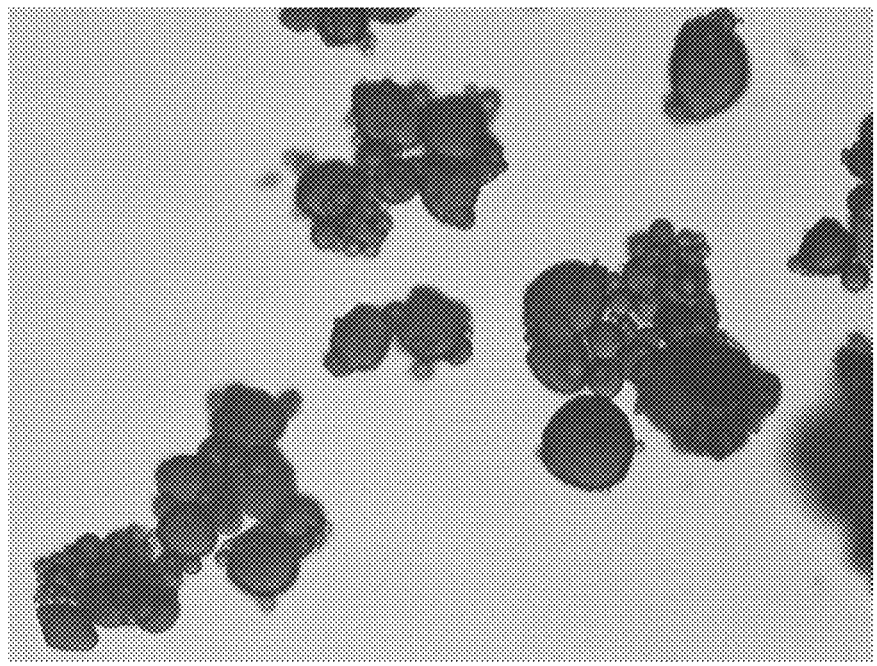
FIGS. 26A-B are scanning electron microscope images of oxidized cellulose microparticles including 25% loaded vitamin B-12 in accordance with the present disclosure.
Figure 26B:
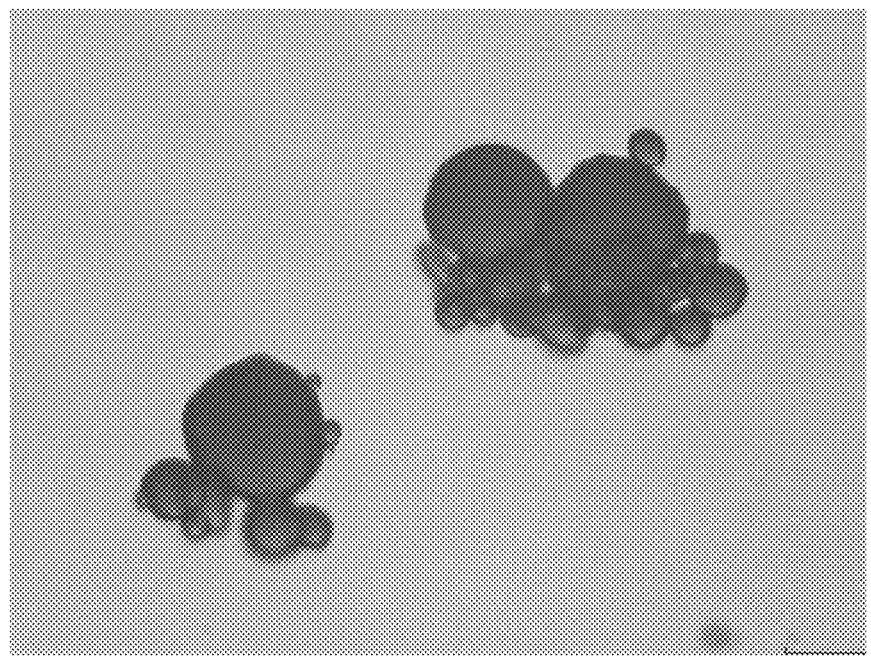

Collected microparticles were imaged using Keyence VHX-600, a light microscope, which are shown in FIGS. 26A-B at about 600× and 1,000×, respectively. The images show microspheres having a substantially spherical shape.

Example 14

This Example describes formation of poly-D,L,-lactide (PDLLA) microspheres encapsulating cis-diamminedichloroplatinum(II) (CDDP) loaded oxidized cellulose microspheres.

A 1 liter glass beaker was set on a ring stand. A constant-torque mixer was fitted with a medium-shear impeller, which was inserted into the beaker. Approximately 200 mL of heavy white mineral oil was added to the beaker with the mixer set to rotate at approximately 1,800 rpm.

About 300 milligrams of CDDP was added to about 3 grams of the oxidized cellulose solution having a concentration of about 15 mg/mL, which formed a gel. The gel was vortexed for about 30 seconds until a uniform consistency was achieved and no particles of CDDP were visible.

The gel of CDDP and oxidized cellulose was then added drop-wise to the vortex of the stirring cottonseed and mineral oils for about 15 minutes at about 1,800 rpm, until all of the solution was added to the oil to form an emulsion.

About 200 mL of cottonseed oil were added to the emulsion and the mixing speed was reduced to about 700 rpm after approximately 1 minute. After about 30 minutes, approximately 200 mL of cottonseed oil was added along with about 50 mL of n-heptane and the emulsion was mixed for approximately 2.5 hours to extract the NMP from the oxidized cellulose microspheres. After the NMP was extracted, microspheres were collected under vacuum by filtration through Whatman No. 4 filter paper. The microspheres were then washed with a sufficient volume of n-heptane to remove any trace of processing oils on the surface of the microspheres.

Figure 27:
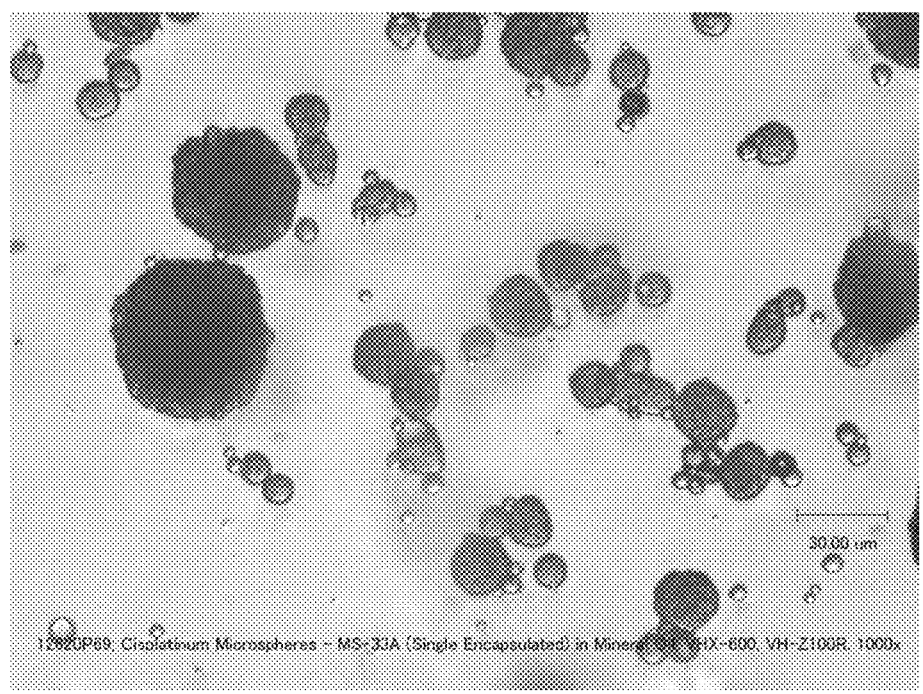
FIG. 27 is a light microscope image of cis-diamminedichloroplatinum(II) loaded oxidized cellulose microspheres in accordance with the present disclosure.

Collected microspheres were imaged using Keyence VHX-600, a light microscope, which are shown in FIG. 27 at about 1,000×. The light images show microspheres having a substantially spherical shape and a smooth surface. The microspheres were of yellow color showing CDDP encapsulation.

A 4 liter glass beaker was set on a ring stand and the mixer was fitted with a high-shear radial impeller above a medium-shear bottom impeller. About 2,500 mL of 1% polyvinyl alcohol (PVA) in water was added to the beaker and the mixing speed was set to about 1,800 rpm. A solution having a concentration of about 200 mg/mL of PDLLA was prepared by dissolving about 1 gram of PDLLA in about 5 mL of dichloromethane. The CDDP/oxidized cellulose microspheres were then added to the PDLLA solution and vortexed to ensure a uniform distribution of the microspheres in the PDLLA solution thereby forming a suspension.

The suspension was then added to the PVA solution. Mixing was maintained at about 1,810 rpm for about 5 minutes after which, the speed was reduced to about 1,150 rpm for about 60 minutes. About 500 mL of distilled water was then added to the emulsion to extract dichloromethane from the multi-encapsulated microspheres, namely, PDLLA microspheres encapsulating the CDDP/oxidized cellulose microsphere. The multi-encapsulated microspheres were harvested after about 2.5 hours of mixing. The microspheres were washed with distilled water to remove all traces of the PVA. They were then collected off each sieve by filtration. The collected microspheres were then air-dried for about 24 hours.

Figure 28:
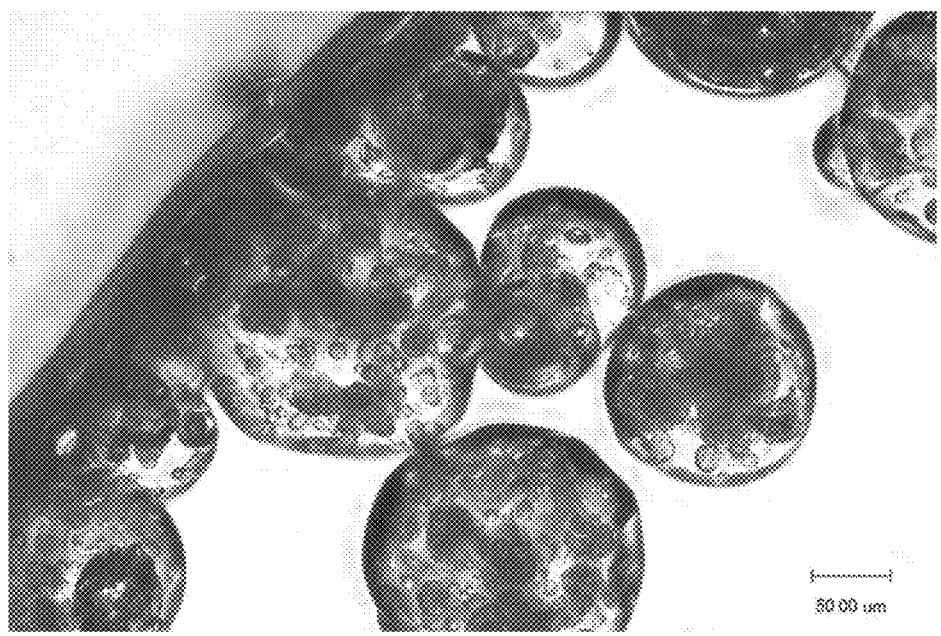
FIG. 28 is a light microscope image of poly-D,L,-lactide microspheres encapsulating cis-diamminedichloroplatinum (II) loaded oxidized cellulose microspheres of FIG. 27 in accordance with the present disclosure.
Figure 29:
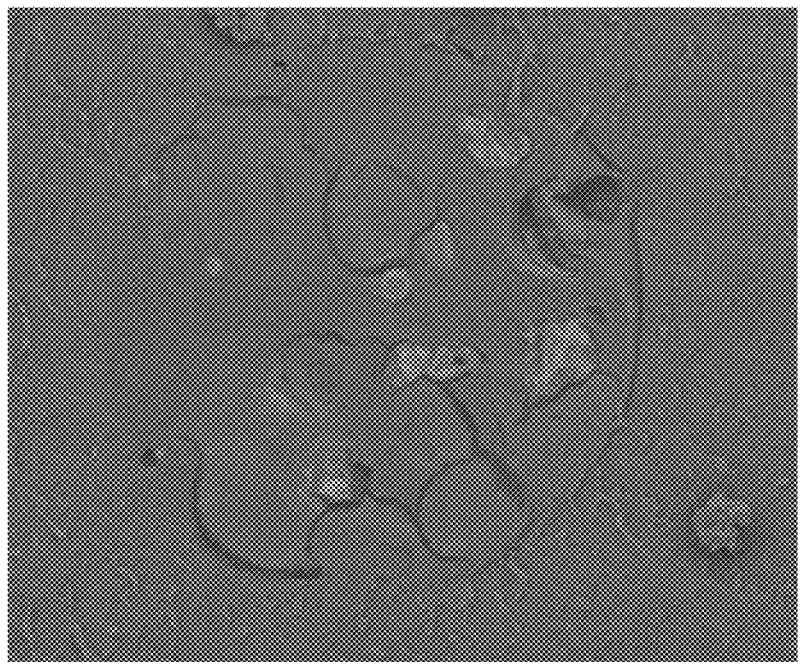
FIG. 29 is a scanning electron microscope image of a cross-section of the microsphere of FIG. 19 in accordance with the present disclosure.

Collected microspheres were imaged using Keyence VHX-600, a light microscope, which are shown in FIG. 28 at about 1,000×. Microspheres were also embedded in epoxy and a cross-sectional slice of thereof was obtained, which was then imaged using a FEI Quanta 600 FEG SEM, which is shown in FIG. 29 at about 1,475×. The images of FIGS. 28 and 29 show larger PDLLA microspheres encapsulating a plurality of oxidized cellulose microspheres, which were observed to be gold in color (FIG. 28), which in turn, encapsulate CDDP, which were observed to be red in color (FIG. 29).

CDDP, a water-soluble compound, was successfully encapsulated in microspheres formed from solubilized oxidized cellulose using an oil-in-oil (o/o), solvent extraction method. These microspheres were then encapsulated in polylactide microspheres, using a solid-in-oil-in-water modified emulsion, solvent extraction (MESE) method. The "microsphere(s)-in-a-microsphere" particles were freeflowing and easily handled, no fragility was observed. Since CDDP encapsulation was conducted without water, sodium chloride was not required, which is used when aqueous systems are employed in encapsulating CDDP to prevent transforming the cis form of CDDP into trans, which is has diminishing bioactive effect.

Example 15

This Example describes formation of 8.2% by weight ferrous gluconate loaded oxidized cellulose microspheres from a 15% by weight/volume oxidized cellulose solution including 1% by weight of LiCl in N-methyl-2-pyrrolidinone (NMP).

The same process was followed as set forth in Example 9 above, except about 100 milligrams of ferrous gluconate was added to the oxidized cellulose solution.

Figure 30:
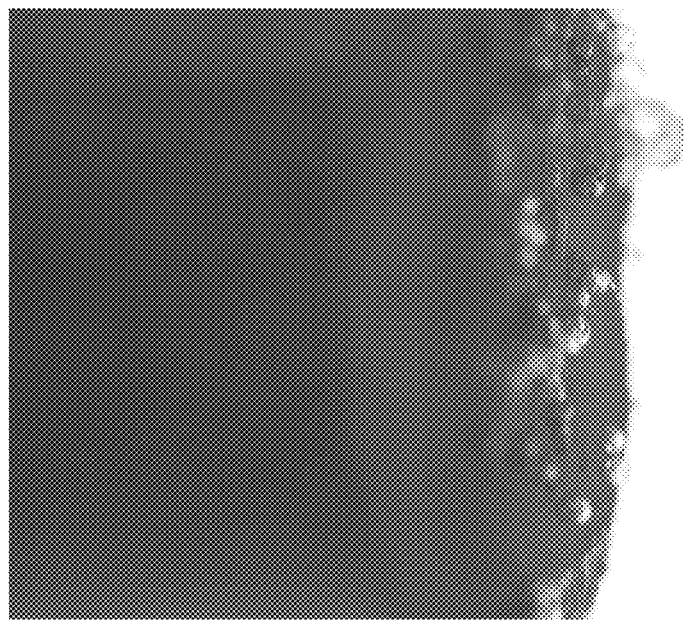
FIG. 30 is a scanning electron microscope image of a cross-section of a microsphere including a magnetic material in accordance with the present disclosure.

Collected microparticles were collected on a glass slide and imaged using an Olympus SZX16, a light microscope, which are shown in FIG. 30 at about 40×. The images show microspheres having a substantially spherical shape and measuring about 100 µm in diameter.

Example 16

This Example describes formation of iodine contrast agent loaded oxidized cellulose microspheres from a 13% by weight/volume oxidized cellulose solution including 1% by weight of LiCl in N-methyl-2-pyrrolidinone (NMP).

Approximately 3 grams of about 13% (w/v) oxidized solution in NMP was added into a glass scintillation vial into which about 1 gram of iohexol (including about 300 mg of iodine) contrast solution was also added. The vial was capped and vortexed for about 30 seconds.

The resulting solution was added drop-wise to a 2 liter glass beaker containing about 400 mL of heavy mineral oil and about 800 mL cottonseed oil and mixed. Subsequently, about 15 mL of isopropyl myristate was added to the beaker along with an additional 200 mL of cottonseed oil to further extract the NMP solvent from the oxidized cellulose microspheres.

About 100 mL of n-heptane was then added after about 2.5 hours, followed by sieving for size fractionation at about 300 µm, 200 µm, 105 µm, and 25 µm and the microspheres were harvested in each size range, then washed with n-heptane to remove any residual oil.

The microspheres were then transferred to a clean glass vessel containing about 25 mL of dichloromethane and swirled gently to further extract NMP and then were allowed to settle, at which time the dichloromethane was decanted and the microspheres were dried under a stream of nitrogen.

The microspheres were collected on Whatman No. 4 filter paper under vacuum and air dried overnight before being bottled under an argon overlay.

For purposes of stability, the carboxylic acid groups on the microspheres were cross-linked with aziridine and an overcoat of triglyceride was added. Subsequently, the microspheres were bottled in 10 mL Wheaton vials under an argon overlay.

Example 17

This Example describes embolization of a blood vessel using the oxidized cellulose including iodine contrast agent.

Figure 31:
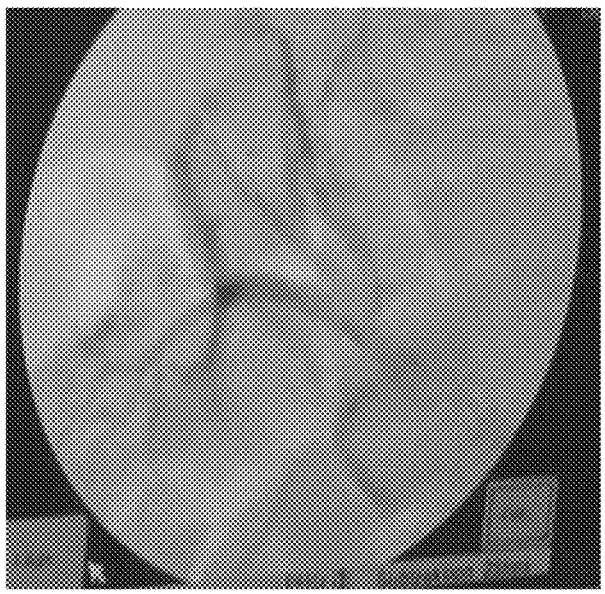
FIG. 31 is an angiogram of a blood vessel prior to embolization in accordance with the present disclosure.
Figure 32:
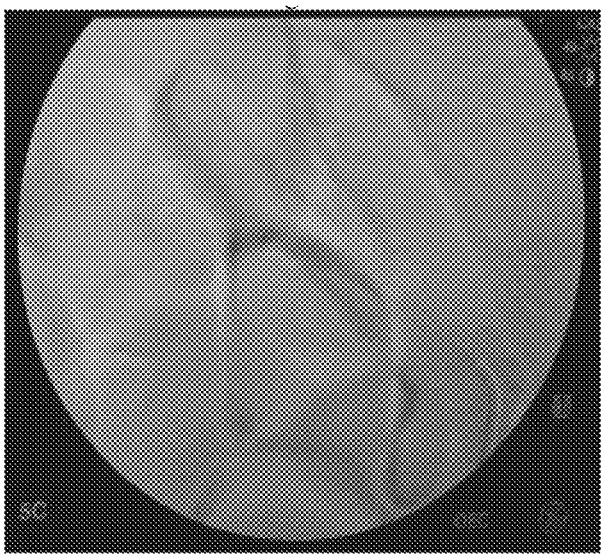
FIG. 32 is an angiogram of the blood vessel of FIG. 31 with oxidized cellulose microspheres containing iodine in accordance with the present disclosure.

Oxidized cellulose microspheres of Example 16 were implanted into a blood vessel as shown in the angiograms of FIGS. 31 and 32. FIG. 31 shows the blood vessel prior to implantation of the microspheres thereinto and FIG. 32 shows occlusion of the blood vessel following implantation.

Example 18

This Example describes formation of an oxidized cellulose slurry from a 15% by weight/volume oxidized cellulose solution including 1% by weight of LiCl in N-methyl-2-pyrrolidinone (NMP).

Approximately 2 grams of about 15% (w/v) oxidized solution in NMP was added into a 2 liter glass beaker containing about 200 mL of heavy mineral oil and about 400 mL cottonseed oil and mixed. Subsequently, about 5 mL of isopropyl myristate was added to the beaker along with an additional 150 mL of cottonseed oil to further extract the NMP solvent from the oxidized cellulose microspheres.

About 50 mL of n-heptane was then added after about 2.5 hours, followed by sieving for size fractionation at about 300 µm, 200 µm, 105 µm, and 25 µm, and the microspheres were harvested in each size range, then washed with n-heptane to remove any residual oil.

The microspheres were then transferred to a clean glass vessel containing about 25 mL of dichloromethane and swirled gently to further extract NMP and then were allowed to settle, at which time the dichloromethane was decanted and the microspheres were dried under a stream of nitrogen.

The microspheres were collected on Whatman No. 4 filter paper under vacuum, and air dried overnight before being bottled under an argon overlay.

For purposes of stability, the carboxylic acid groups on the microspheres were cross-linked with aziridine and an overcoat of triglyceride was added. Subsequently, the microspheres were bottled in 10 mL Wheaton vials under an argon overlay.

About 0.4 grams of oxidized cellulose microspheres and about 1.0 mL of an iodixanol solution having a concentration of iodine of about 270 mg/mL (available as VISIPAQUE® from GE Healthcare of Little Chalfont, United Kingdom) were then added to about 1.0 mL of a saline solution, which after about 10 minutes resulted in a polymer slurry.

Example 19

This Example describes embolization of a blood vessel in a porcine animal model using the oxidized cellulose slurry of Example 18.

Figure 33:
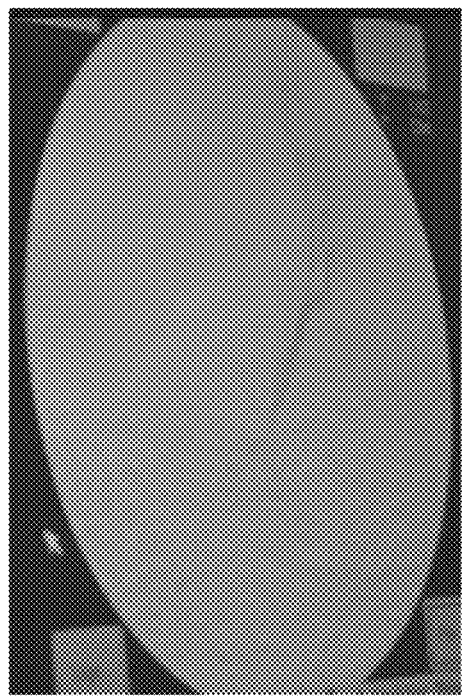
FIG. 33 is an angiogram of a blood vessel prior to embolization in accordance with the present disclosure.
Figure 34:
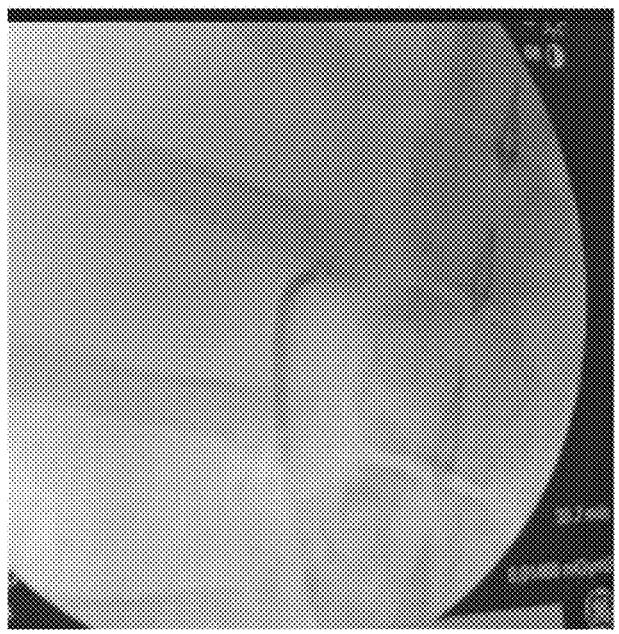
FIG. 34 is an angiogram of the blood vessel of FIG. 33 with oxidized cellulose embolization slurry containing iodine in accordance with the present disclosure.

The oxidized cellulose slurry of Example 18 was implanted into a blood vessel as shown in the angiograms of FIGS. 33 and 34. FIG. 33 shows the blood vessel prior to implantation of the microspheres therein and FIG. 34 shows occlusion of the blood vessel following implantation.

Example 20

This Example describes analysis of degree of oxidation of the oxidized cellulose of Example 1.

Degree of oxidation of dissolved oxidized cellulose was analyzed using conductimetric and pH metric titration and compared with the degree of oxidation of undissolved oxidized cellulose.

Multiple samples from about 90 mg to about 700 mg of undissolved oxidized cellulose and from about 560 mg to about 4.4 grams of about 16% by weight/volume of the oxidized cellulose solution of Example 1 were prepared. Each of the samples was dissolved in about 15 mL of a sodium hydroxide (NaOH) solution having a molarity (M)

from about 0.05 M to about 0.5 M. The resulting solutions were titrated with a hydrogen chloride (HCl) solution from about 0.05 M to about 0.5 M on a TIM 845 titration apparatus (from Radiometer Analytical SAS, Villeurganne Cedex, France) and conductimetric and pH-metric curves were obtained. A blank titration was done in the same conditions to determine the NaOH concentration.

Figure 35:
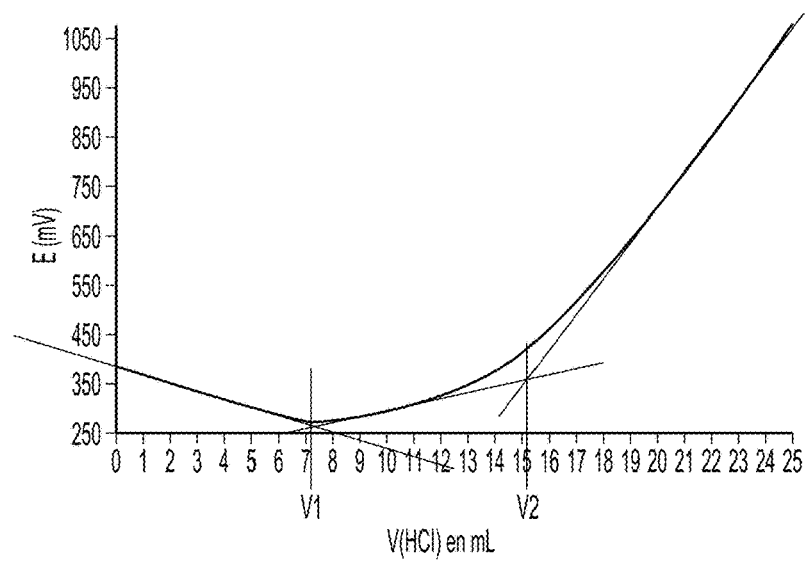
FIG. 35 is a plot of a conductometric titration curve of oxidized cellulose in accordance with the present disclosure.
Figure 36:
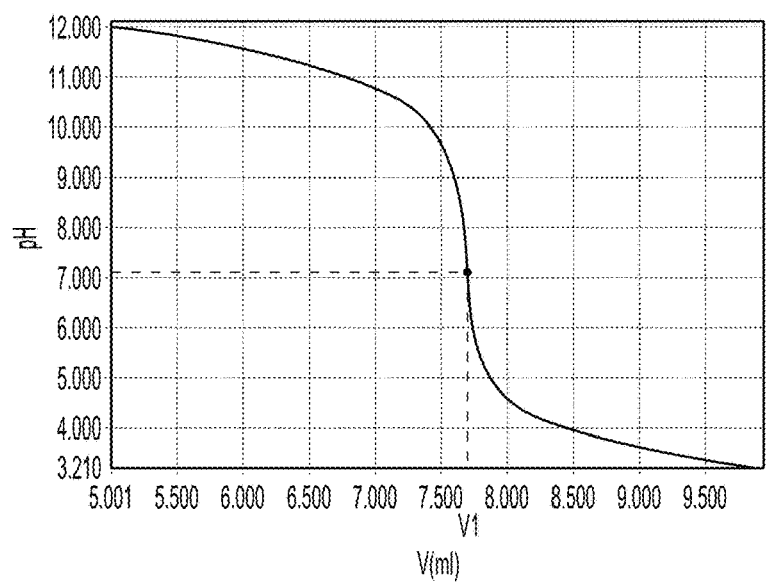
FIG. 36 is a plot of a pH-metric titration curve of oxidized cellulose in accordance with the present disclosure.

The conductometric titration curves showed the presence of strong alkali, corresponding to the excess of NaOH and a weak alkali corresponding to the carboxyl content, as shown in the illustrative conductometric curve of FIG. 35. The characteristic pH-metric curve is shown in the FIG. 36, in which the equivalence point corresponds to the residual NaOH in the samples.

The degree of oxidation for each sample was calculated using the following formulas (I) and (II):

$$DO = \frac{162 \times n(COOH)}{w - (14 \times n(COOH))} \quad (I)$$

$$n(COOH) = (V2 - V1) \times C(HCl) \quad (II)$$

in which V2 is the volume of HCl in liters obtained by the blank titration or from the conductometric curve as indicated in FIG. 35; V1 is the amount HCl in liters as shown in FIG. 35, or the equivalence point from the pH-metric titration of FIG. 36; C is HCl concentration in moles per liter (Mol/L) and w is the weight of the oven-dried sample of undissolved oxidized cellulose in grams.

The degree of oxidation of non-dissolved oxidized cellulose and for dissolved oxidized cellulose of Example 1 samples are summarized in Table 3 below:

TABLE 3

|  | Undissolved Oxidized Cellulose | Dissolved Oxidized Cellulose |
| --- | --- | --- |
|  | 0.6 | 0.53 |
|  | 0.56 | 0.52 |
|  | 0.57 | 0.52 |
|  | 0.6 |  |
|  | 0.56 |  |
|  | 0.59 |  |
|  | 0.6 |  |
|  | 0.6 |  |
|  | 0.62 |  |
|  | 0.59 |  |
|  | 0.61 |  |
|  | 0.57 |  |
| mean | 0.59 | 0.52 |
| std dev | 0.020 | 0.006 |

Example 21

This Example describes embolization of a blood vessel in a porcine animal model using a liquid oxidized cellulose embolization solution.

Figure 37:
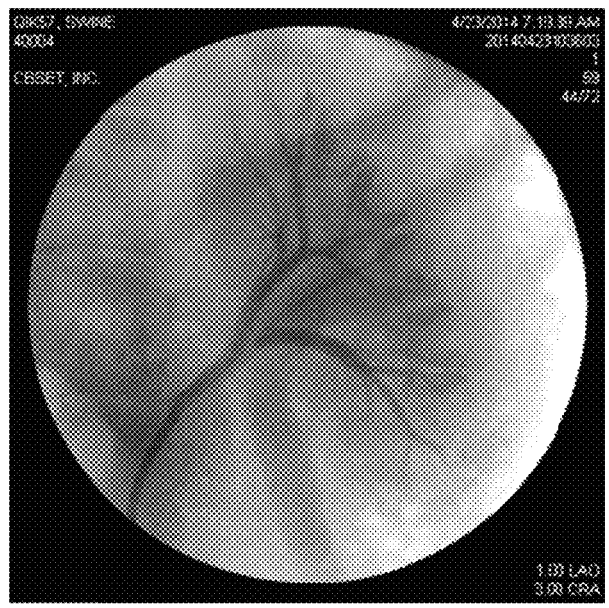
FIG. 37 is an angiogram of a blood vessel prior to embolization in accordance with the present disclosure.
Figure 38:
FIG. 38 is an angiogram of the blood vessel of FIG. 33 with oxidized cellulose embolization slurry containing iodine in accordance with the present disclosure.

The oxidized cellulose solution of Example 1 was implanted into a blood vessel of a porcine kidney as shown in the angiograms of FIGS. 37 and 38. FIG. 37 shows the blood vessel prior to implantation of the microspheres using a microcatheter and FIG. 38 shows occlusion of the blood vessel following introduction of the oxidized cellulose embolization solution.

Example 22

This Example describes the thixotropic behavior of approximately 12% and 20% by weight/volume of the oxidized cellulose solutions of Example 1.

About 12% by weight/volume of the oxidized cellulose in NMP solution and approximately 20% by weight/volume of the oxidized cellulose in NMP solution were prepared using the process of Example 1. With reference to FIG. 39, photographs of a first bottle containing about 15 mL of 12% by weight/volume of the oxidized cellulose solution and a second bottle of about 15 mL of approximately 20% by weight/volume of the oxidized cellulose solution are shown. After sealing the bottles, each of the bottles was left undisturbed for about 5 seconds until the solution settled and gelled. The bottles were then shaken for approximately 5 seconds until the solutions inside became less viscous and flowable. Thereafter the bottles were left undisturbed again for about 5 seconds and the solutions returned to their more viscous, gelled states.

Example 23

This Example describes the thixotropic behavior of three oxidized cellulose solutions of Example 1.

Three different oxidized cellulose solutions were prepared using the process of Example 1. Samples 1 and 2 were well solubilized with the oxidized cellulose being completely dissolved with no observable particulates when the sample was filtered. Sample 3 was poorly solubilized, with particulate oxidized cellulose being observed when filtered. Samples 1-3 were subjected to rheological analysis using a cone-and-plate controlled stress instrument, TA Instruments AR-G2 rheometer with an approximately 4 cm 2° cone using the following steps to test thixotropic properties of Samples 1-3:

1) Frequency sweep, from about 0.1 Hz to about 100 Hz, with 5% strain, and 5 points per decade to allow for stabilization and report equilibrium conditions.

2) Steady shear at a rate of about 1 $s^{-1}$ stepwise change without ramping then tracking for about 10 minutes to test for thixotropy under low shear rate.

3) Steady shear at a rate of about 1,000 $s^{-1}$ step wise change without ramping then tracking for about 10 minutes to test for thixotropy under high shear rate.

4) Time sweep, 5% strain at about 1 Hz for about 30 minutes without shearing to examine if any structures were rebuilt.

5) Steady shear continuous ramp from about 0.01 to about 10,000 $s^{-1}$ over about 5 minutes.

6) Frequency sweep, from about 0.1 HZ to about 100 Hz, with 5% strain, and 5 points per decade to confirm that nothing has changed in the system.

Figure 40:
FIG. 40 is a plot of viscosity over time for a plurality of thixotropic oxidized cellulose solutions subjected to low shear rates illustrating thixotropic behavior thereof in accordance with the present disclosure.

Each of the Samples 1-3 were subjected to the rheological analysis summarized above. FIG. 40 shows plots of viscosity over time of Samples 1-3 (three plots per sample including average, lower and upper standard deviation bounds) illustrating their thixotropic behavior under low shear rate (step 2 of the above-summarized procedure). Sample 3 demonstrated no thixotropic behavior during the low-shear rate step, with an observable almost constant viscosity at all times as shown in FIG. 40. In contrast, Samples 1 and 2 were substantially more viscous and demonstrated a pronounced viscosity increase over time. This observation suggests that there are structures within the Samples 1 and 2 which form networks of or additional structuring to increase viscosity. Samples 1 and 2 also appeared to exhibit a viscosity overshoot upon start up, shown as an initial peak, which is consistent with an initial breakup of structures to start the material moving within the solutions.

Figure 41:
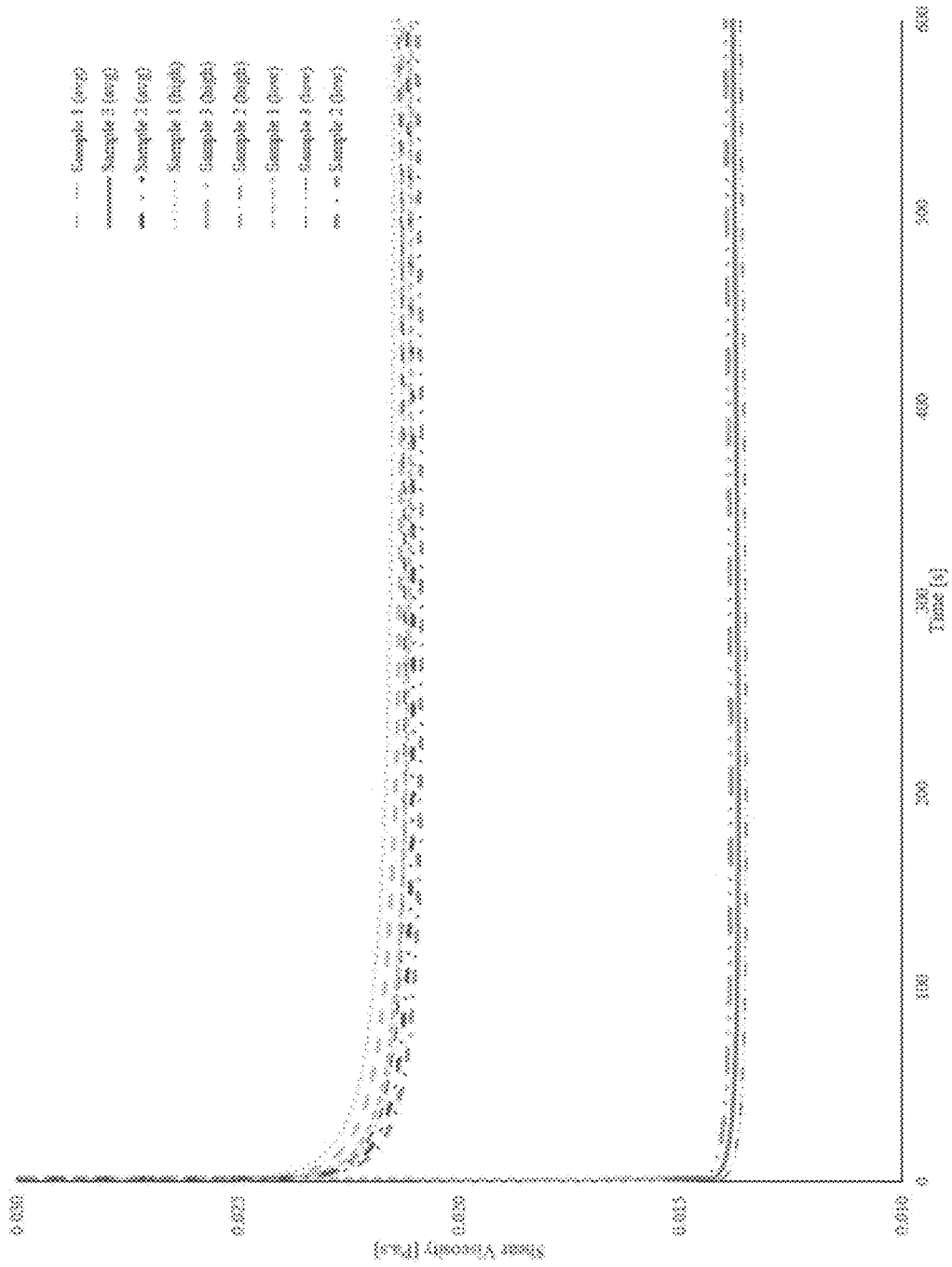
FIG. 41 is a plot of viscosity over time for a plurality of thixotropic oxidized cellulose solutions subjected to high shear rates illustrating thixotropic behavior thereof in accordance with the present disclosure.

FIG. 41 shows plots of viscosity over time of Samples 1-3 (three plots per sample including average, lower and upper standard deviation bounds) illustrating their thixotropic behavior under high shear rate (step 2 of the above-summarized procedure). All of the Samples 1-3 exhibited sharp drops in viscosity, but once again Samples 1 and 2 were more viscous than Sample 3. In addition, Sample 3 exhibited minimal thixotropic response, with only a slight drop in viscosity evident at very short times with the viscosity apparently almost constant by about 50 seconds into experiment. In contrast, Samples 1 and 2 exhibited a broad transition extending out to about 200 seconds and visibly dropping by about 10% of the final value. The steep drop visible in all plots for the first few seconds demonstrates the transition from low-shear to high-shear sections of the experiment. This suggests that Samples 1 and 2, which are better solubilized and stabilized than Sample 3, have greater inter-molecule interactions allowing for formation of structures in the solution. It is believed that these structures are responsible for the observed differences in performance of the Samples 1-3.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A method for forming an embolism, comprising:
    applying a shear force to a thixotropic oxidized cellulose solution to form a reduced viscosity thixotropic oxidized cellulose solution; and
    delivering the reduced viscosity thixotropic oxidized cellulose solution to a blood vessel,
    wherein a viscosity of the thixotropic oxidized cellulose solution increases at the blood vessel after delivery.

2. The method according to claim 1, further comprising:
    contacting the thixotropic oxidized cellulose solution with a bioactive agent.

3. The method according to claim 1, further comprising placing the thixotropic oxidized cellulose solution into a delivery device.

4. The method according to claim 3, wherein delivering the reduced viscosity thixotropic oxidized cellulose solution includes injecting the reduced viscosity thixotropic oxidized cellulose solution into the blood vessel to form a scaffold therein.

5. The method according to claim 3, wherein the thixotropic oxidized cellulose solution is placed into the delivery device selected from the group consisting of a syringe, a catheter, and an endoscope.

6. The method according to claim 3, wherein administering the reduced viscosity thixotropic oxidized cellulose solution to the blood vessel includes injecting the reduced viscosity thixotropic oxidized cellulose solution into the blood vessel.

7. The method according to claim 1, wherein the thixotropic oxidized cellulose solution includes oxidized cellulose having a degree of oxidation from about 0.5 to about 0.8 and is present from about 5% by weight to 20% by weight of the thixotropic oxidized cellulose solution.

8. A method for forming an embolism, comprising:
    forming a thixotropic oxidized cellulose solution;
    contacting the thixotropic oxidized cellulose solution with a bioactive agent to form a thixotropic formulation;
    loading the thixotropic formulation into a delivery device;
    applying a shear force to the thixotropic formulation within the delivery device to form a reduced viscosity thixotropic formulation; and
    delivering the reduced viscosity thixotropic formulation to a blood vessel from the delivery device,
    wherein a viscosity of the thixotropic formulation increases at the blood vessel after delivery.

9. The method according to claim 8, wherein delivering the reduced viscosity thixotropic formulation includes injecting the reduced viscosity thixotropic formulation into the blood vessel to form a tissue scaffold therein.

10. The method according to claim 8, wherein shear force is applied to the reduced viscosity thixotropic formulation within the delivery device selected from the group consisting of a syringe, a catheter, and an endoscope.

11. The method according to claim 8, wherein delivering the reduced viscosity thixotropic formulation to the blood vessel includes injecting the reduced viscosity thixotropic formulation into the blood vessel.

12. The method according to claim 8, administering the reduced viscosity thixotropic formulation to the blood vessel includes applying the reduced viscosity thixotropic formulation topically.

* * * * *